United States Patent
Goldberg

(10) Patent No.: US 9,775,716 B2
(45) Date of Patent: Oct. 3, 2017

(54) GLENOID ARTHROPLASTY

(71) Applicant: CATALYST ORTHOSCIENCE INC., Naples, FL (US)

(72) Inventor: Steven S. Goldberg, Naples, FL (US)

(73) Assignee: CATALYST ORTHOSCIENCE INC., Naples, FL (US)

(*) Notice: Subject to any disclaimer, the term of this patent is extended or adjusted under 35 U.S.C. 154(b) by 0 days.

(21) Appl. No.: 14/042,258

(22) Filed: Sep. 30, 2013

(65) Prior Publication Data
US 2014/0257495 A1 Sep. 11, 2014

Related U.S. Application Data

(60) Provisional application No. 61/776,398, filed on Mar. 11, 2013.

(51) Int. Cl.
| | | |
|---|---|---|
| A61F 2/40 | (2006.01) | |
| A61B 17/16 | (2006.01) | |
| A61B 17/17 | (2006.01) | |
| A61F 2/30 | (2006.01) | |

(52) U.S. Cl.
CPC ........ *A61F 2/4081* (2013.01); *A61B 17/1604* (2013.01); *A61B 17/1684* (2013.01); *A61B 17/1778* (2016.11); *A61F 2/30771* (2013.01); *A61B 17/1659* (2013.01); *A61F 2002/30156* (2013.01); *A61F 2002/30878* (2013.01); *A61F 2002/30881* (2013.01); *A61F 2002/30884* (2013.01); *A61F 2002/30892* (2013.01); *A61F 2002/30902* (2013.01); *A61F 2002/30904* (2013.01)

(58) Field of Classification Search
CPC .......... A61F 2/4081; A61F 2002/30884; A61F 2002/30878; A61F 2/30767; A61F 2/40; A61F 2/4014; A61F 2/4612; A61F 2/4059; A61F 2250/0039
See application file for complete search history.

(56) References Cited

U.S. PATENT DOCUMENTS

| | | | |
|---|---|---|---|
| 4,106,130 A | 8/1978 | Scales | |
| 4,206,517 A | 6/1980 | Pappas et al. | |
| 4,550,450 A | 11/1985 | Kinnett | |
| 4,865,605 A | 9/1989 | Dines | |
| 4,964,865 A * | 10/1990 | Burkhead et al. | ......... 623/19.11 |
| 4,986,833 A | 1/1991 | Worland | |
| 5,030,219 A | 7/1991 | Matsen, III | |
| 5,032,132 A | 7/1991 | Matsen, III | |

(Continued)

FOREIGN PATENT DOCUMENTS

| | | |
|---|---|---|
| AT | 2013209336 | 2/2014 |
| CA | 2821529 | 1/2014 |

(Continued)

*Primary Examiner* — Ann Schillinger
(74) *Attorney, Agent, or Firm* — Maywood IP Law; G. Jo Hays; David W. Meibos

(57) ABSTRACT

Arthroplasty components include an articular surface and a bone-facing surface. The bone-facing surface bears at least one anchoring element adapted for an oblique implantation trajectory. The articular surface includes a larger radius of curvature in the superior-inferior direction than in the anterior-posterior direction. An inferior chamfer may be present on the articular surface. Instruments and implantation methods are also disclosed.

20 Claims, 63 Drawing Sheets

(56) References Cited

U.S. PATENT DOCUMENTS

| | | | |
|---|---|---|---|
| 5,383,936 A | 1/1995 | Kubein Meesenburg | |
| 5,489,310 A | 2/1996 | Mikhail | |
| 5,702,447 A * | 12/1997 | Walch et al. | 623/19.11 |
| 5,723,018 A | 3/1998 | Cyprien | |
| 5,769,856 A | 6/1998 | Dong | |
| 5,800,551 A | 9/1998 | Williamson | |
| 5,814,049 A | 9/1998 | Pratt | |
| 5,919,195 A | 7/1999 | Wilson | |
| 5,928,285 A | 7/1999 | Bigliani | |
| 5,944,758 A | 8/1999 | Mansat | |
| 5,976,144 A | 11/1999 | Fishbein | |
| 6,129,732 A | 10/2000 | Lechot | |
| 6,245,074 B1 | 6/2001 | Allard | |
| 6,364,910 B1 * | 4/2002 | Shultz et al. | 623/19.13 |
| 6,379,386 B1 | 4/2002 | Resch | |
| 6,406,495 B1 | 6/2002 | Schoch | |
| 6,475,221 B1 | 11/2002 | White | |
| 6,673,115 B2 | 1/2004 | Resch | |
| 6,679,916 B1 * | 1/2004 | Frankle et al. | 623/19.12 |
| 6,783,549 B1 | 8/2004 | Stone et al. | |
| 6,875,234 B2 | 4/2005 | Lipman | |
| 6,911,047 B2 | 6/2005 | Rockwood, Jr. | |
| 7,008,430 B2 | 3/2006 | Dong | |
| 7,048,740 B2 | 5/2006 | White | |
| 7,160,328 B2 | 1/2007 | Rockwood, Jr. | |
| 7,204,854 B2 | 4/2007 | Guederian | |
| 7,217,272 B2 | 5/2007 | Salyer | |
| 7,294,149 B2 | 11/2007 | Hozack | |
| 7,329,284 B2 | 2/2008 | Maroney | |
| 7,588,572 B2 | 9/2009 | White | |
| 7,621,962 B2 | 11/2009 | Lakin | |
| 7,670,382 B2 | 3/2010 | Parrott | |
| 7,780,669 B2 | 8/2010 | Lechot | |
| 7,815,685 B2 | 10/2010 | Farrar | |
| 7,867,234 B2 | 1/2011 | Collazo | |
| 8,007,538 B2 | 8/2011 | Gunther | |
| 8,038,719 B2 | 10/2011 | Gunther | |
| 8,048,161 B2 | 11/2011 | Guederian | |
| 8,080,063 B2 * | 12/2011 | Ferrand et al. | 623/19.13 |
| 8,157,866 B2 | 4/2012 | Winslow | |
| 8,308,809 B2 | 11/2012 | Bishop | |
| 8,425,614 B2 | 4/2013 | Winslow | |
| 8,444,646 B2 | 5/2013 | Long | |
| 8,465,548 B2 | 6/2013 | Long | |
| 8,475,460 B1 | 7/2013 | Roger | |
| 8,480,674 B1 | 7/2013 | Roger | |
| 8,540,778 B2 * | 9/2013 | Rhodes | A61F 2/389 623/20.32 |
| 8,591,592 B2 | 11/2013 | Dreyfuss | |
| 8,673,015 B2 | 3/2014 | Maroney | |
| 8,764,836 B2 | 7/2014 | De Wilde | |
| 8,778,028 B2 | 7/2014 | Gunther | |
| 8,870,962 B2 | 10/2014 | Roche | |
| 8,876,907 B2 | 11/2014 | Baptista | |
| 8,974,537 B2 | 3/2015 | Dreyfuss | |
| D730,522 S | 5/2015 | Goldberg | |
| 9,119,643 B2 | 9/2015 | Winslow | |
| 9,180,016 B2 | 11/2015 | Maroney | |
| 9,233,003 B2 | 1/2016 | Roche | |
| 9,237,894 B2 | 1/2016 | Hernandez | |
| 9,283,076 B2 | 3/2016 | Sikora | |
| 9,351,844 B2 | 5/2016 | Walch | |
| D759,819 S | 6/2016 | Goldberg | |
| 9,370,428 B2 | 6/2016 | Winslow | |
| 9,433,507 B2 | 9/2016 | Reubelt | |
| 9,474,619 B2 | 10/2016 | Reubelt | |
| 9,610,166 B2 | 4/2017 | Gunther | |
| 2002/0082702 A1 | 6/2002 | Resch | |
| 2003/0187449 A1 | 10/2003 | McCleary | |
| 2003/0204263 A1 | 10/2003 | Justin et al. | |
| 2005/0049709 A1 * | 3/2005 | Tornier | 623/19.13 |
| 2005/0222572 A1 | 10/2005 | Chana | |
| 2006/0074430 A1 | 4/2006 | Deffenbaugh | |
| 2006/0094958 A1 | 5/2006 | Marquart | |
| 2006/0111787 A1 | 5/2006 | Bailie et al. | |
| 2007/0055380 A1 | 3/2007 | Berelsman | |
| 2007/0142917 A1 | 6/2007 | Roche | |
| 2007/0219637 A1 | 9/2007 | Berelsman | |
| 2007/0219638 A1 | 9/2007 | Jones | |
| 2007/0225817 A1 | 9/2007 | Reubelt | |
| 2007/0225818 A1 | 9/2007 | Reubelt | |
| 2007/0299529 A1 | 12/2007 | Rhodes | |
| 2008/0109000 A1 | 5/2008 | Maroney | |
| 2008/0147070 A1 | 6/2008 | Michel | |
| 2009/0125113 A1 | 5/2009 | Guederian | |
| 2009/0192621 A1 | 7/2009 | Winslow et al. | |
| 2009/0226068 A1 | 9/2009 | Fitz | |
| 2010/0087876 A1 | 4/2010 | Gunther | |
| 2010/0087877 A1 | 4/2010 | Gunther | |
| 2010/0161065 A1 | 6/2010 | Williams, Jr. | |
| 2010/0241235 A1 | 9/2010 | Basamania | |
| 2010/0268239 A1 | 10/2010 | Sikora | |
| 2011/0035013 A1 | 2/2011 | Winslow | |
| 2011/0106266 A1 | 5/2011 | Schwyzer | |
| 2011/0230972 A1 | 9/2011 | Katrana | |
| 2012/0130498 A1 | 5/2012 | Long | |
| 2012/0130500 A1 | 5/2012 | Maroney | |
| 2012/0209392 A1 | 8/2012 | Angibaud | |
| 2012/0310360 A1 | 12/2012 | Parrott | |
| 2013/0024000 A1 | 1/2013 | Bojarski | |
| 2013/0144393 A1 | 6/2013 | Mutchler | |
| 2013/0166033 A1 | 6/2013 | Gunther | |
| 2014/0031945 A1 | 1/2014 | Baptista | |
| 2015/0119891 A1 | 4/2015 | Goldberg | |
| 2015/0320567 A1 | 11/2015 | Terrill | |
| 2016/0089164 A1 | 3/2016 | Winslow | |
| 2016/0095607 A1 | 4/2016 | Hernandez | |
| 2016/0242921 A1 | 8/2016 | Walch | |
| 2016/0287266 A1 | 10/2016 | Sikora | |
| 2017/0014238 A1 | 1/2017 | Reubelt | |
| 2017/0042689 A1 | 2/2017 | Goldberg | |

FOREIGN PATENT DOCUMENTS

| | | |
|---|---|---|
| CN | 101442961 | 11/2012 |
| CN | 102014800 | 4/2014 |
| CN | 105377195 | 3/2016 |
| DE | 10130796 | 1/2003 |
| DE | 10134511 | 2/2003 |
| EP | 1518519 | 3/2005 |
| EP | 1159939 | 7/2005 |
| EP | 2238949 | 10/2010 |
| EP | 2446859 | 5/2012 |
| EP | 2559406 | 2/2013 |
| EP | 2689751 | 1/2014 |
| EP | 2967892 | 1/2016 |
| FR | 2825263 | 12/2002 |
| FR | 2836821 | 5/2004 |
| GB | 2308068 | 9/1999 |
| WO | WO9815241 | 4/1998 |
| WO | WO0018335 | 4/2000 |
| WO | WO0217822 | 3/2002 |
| WO | WO2006110896 | 10/2006 |
| WO | WO2007109800 | 9/2007 |
| WO | WO2009108591 | 9/2009 |
| WO | WO2012030794 A1 | 3/2012 |
| WO | WO2013020026 A1 | 2/2013 |
| WO | WO2014005644 | 1/2014 |
| WO | WO2014164265 | 10/2014 |
| WO | WO2015106136 | 7/2015 |

* cited by examiner

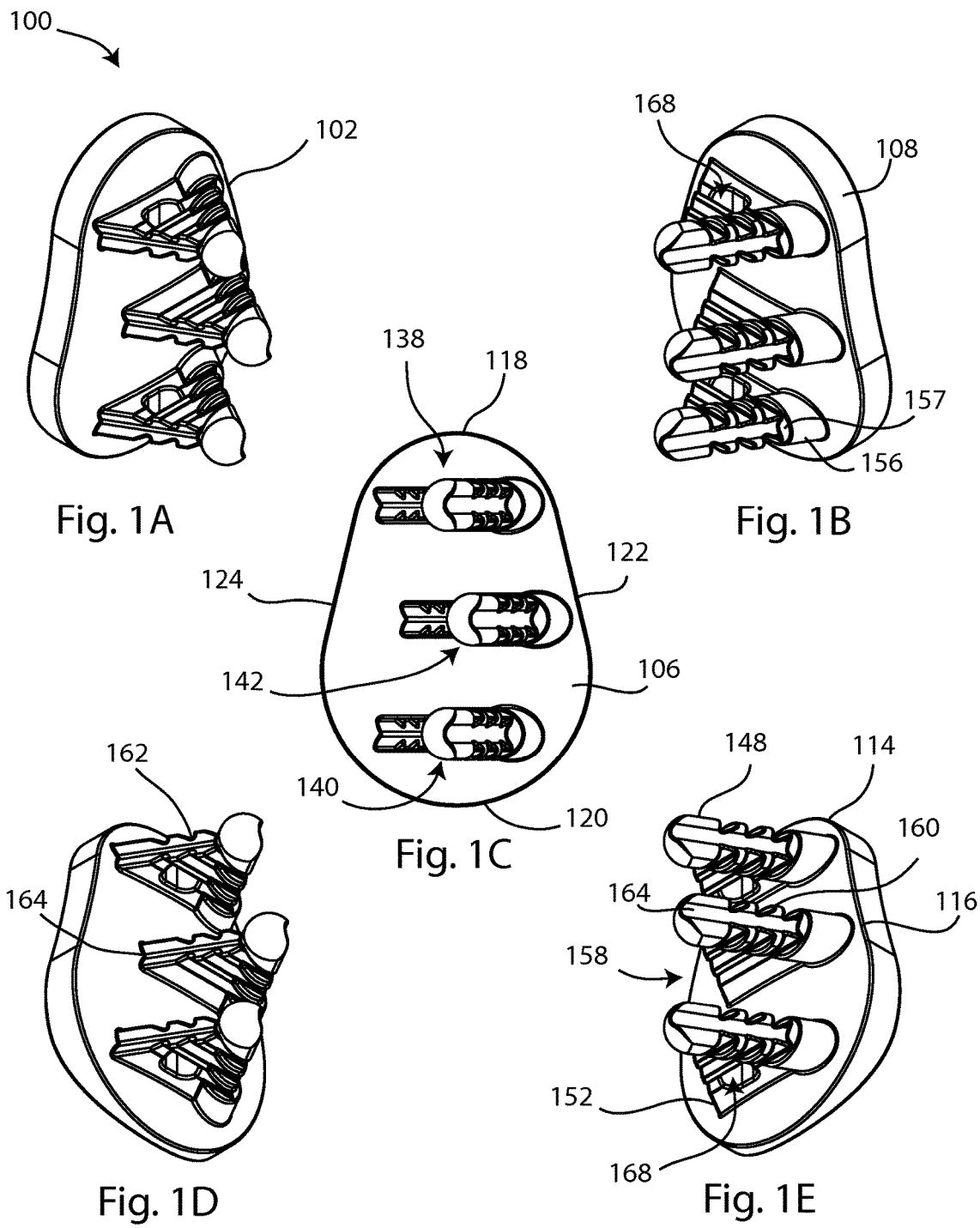

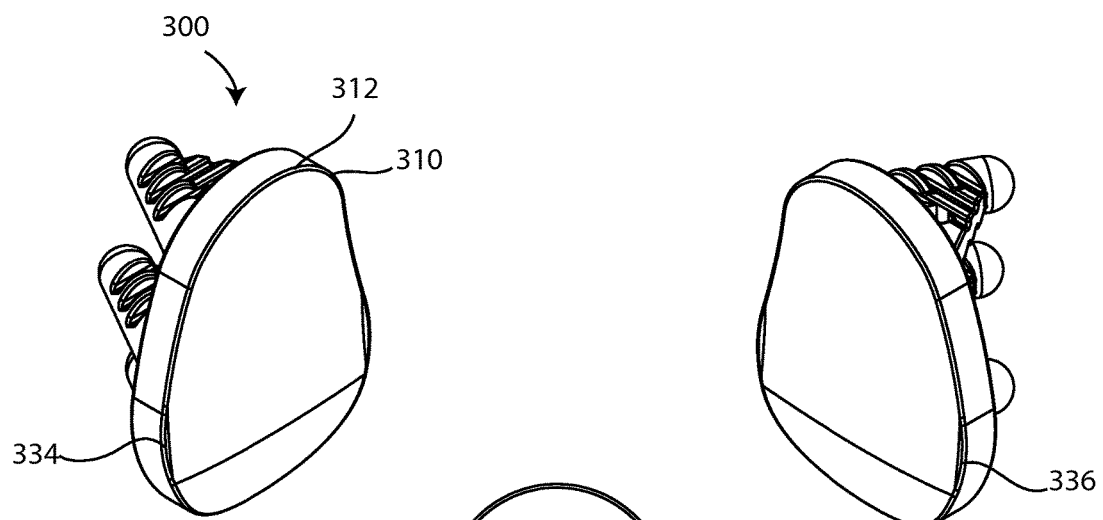
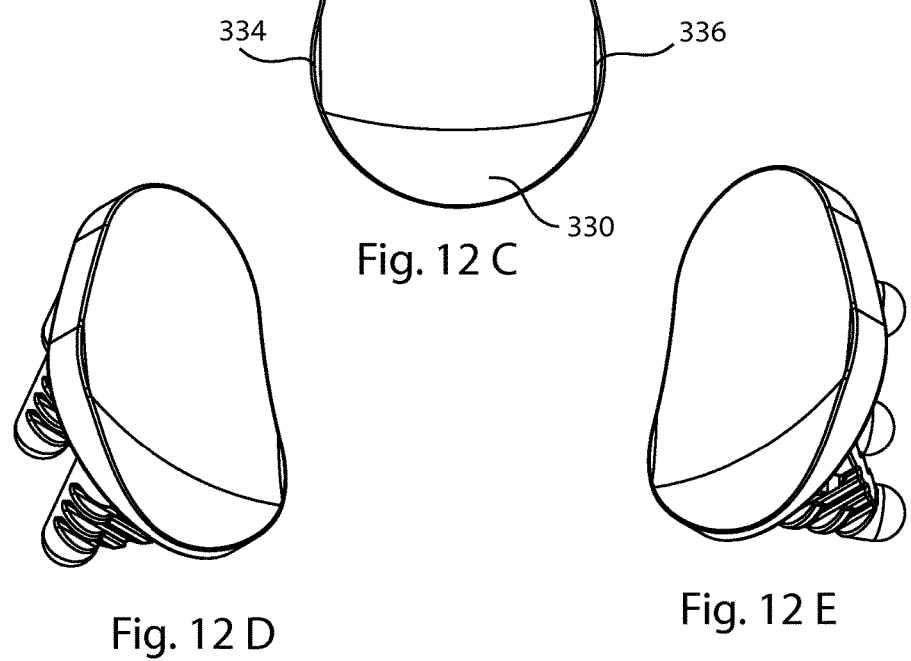
Fig. 12 A  Fig. 12 B  Fig. 12 C  Fig. 12 D  Fig. 12 E

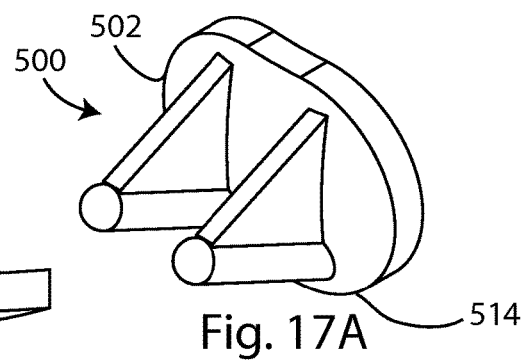
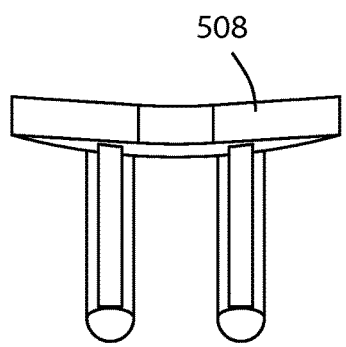
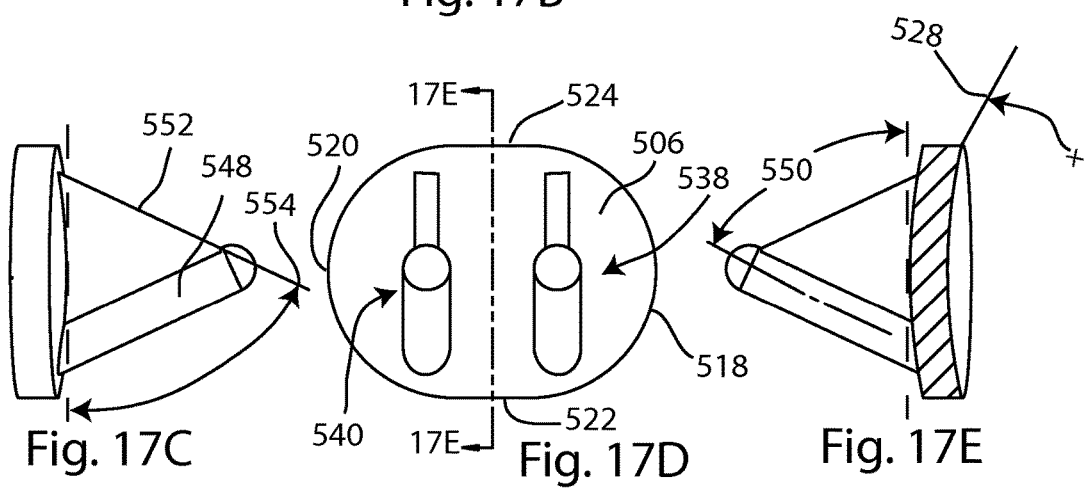
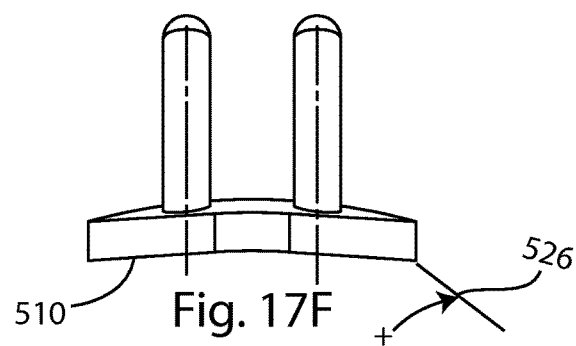

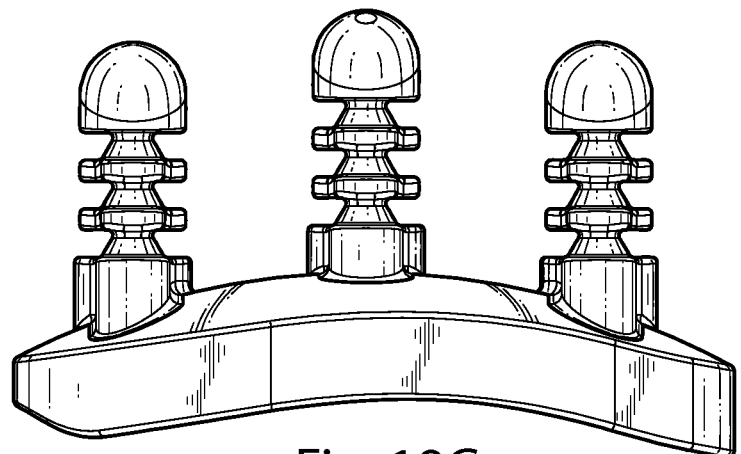
Fig. 19G
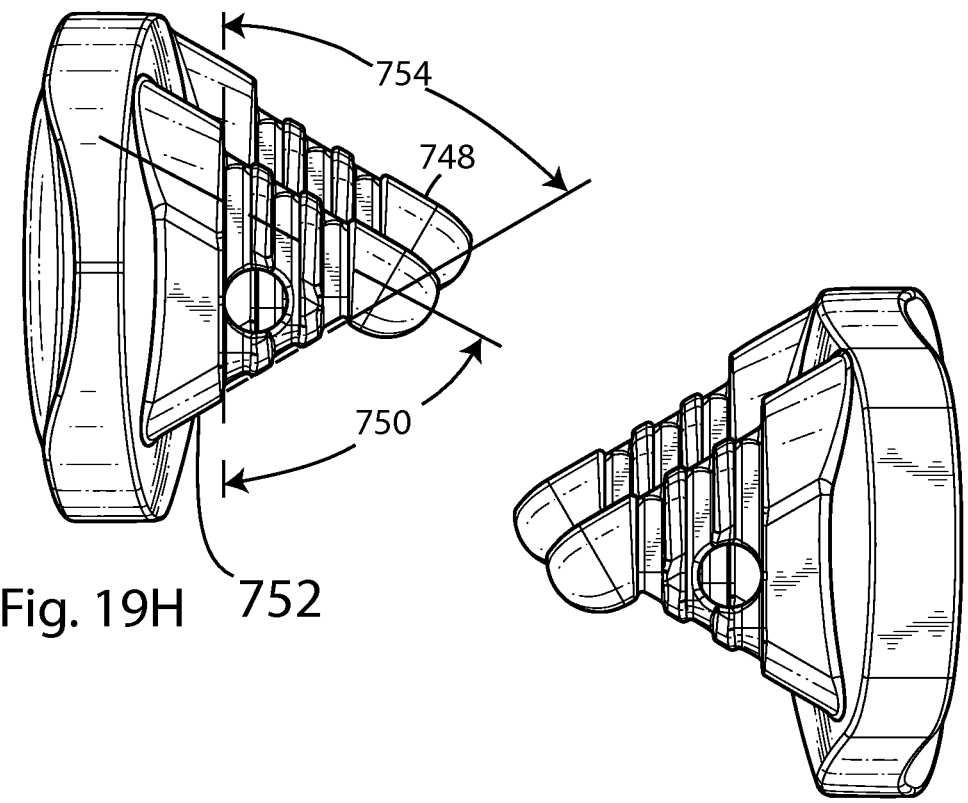
Fig. 19H  752
Fig. 19I

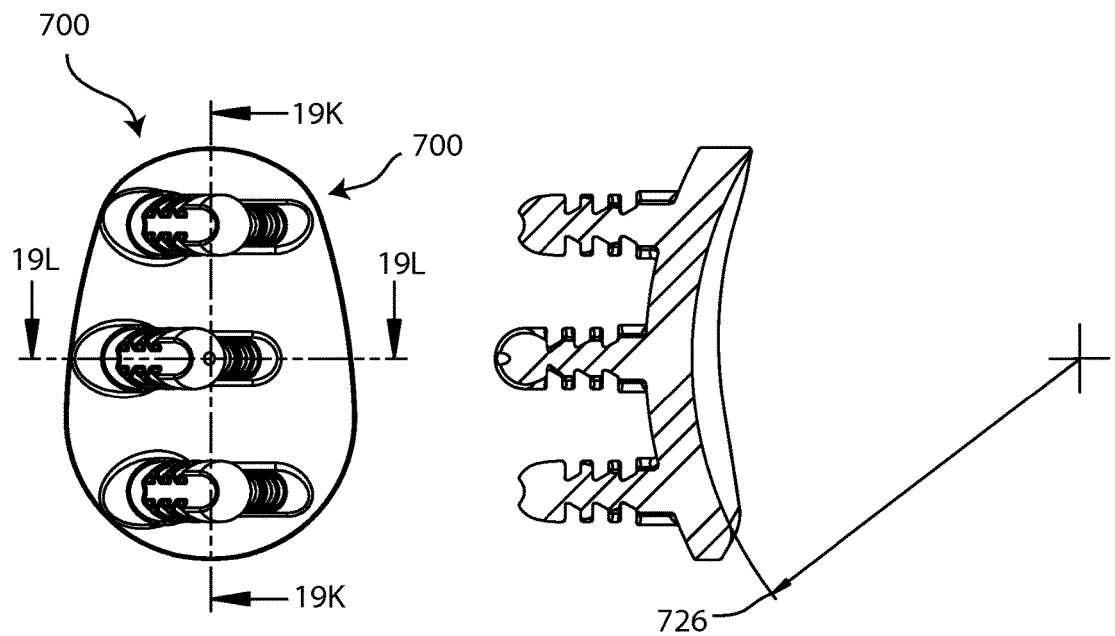
Fig. 19J
Fig. 19K
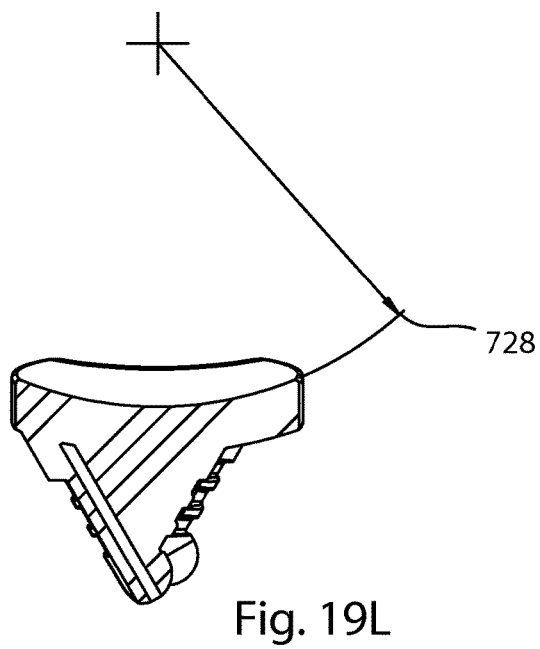
Fig. 19L

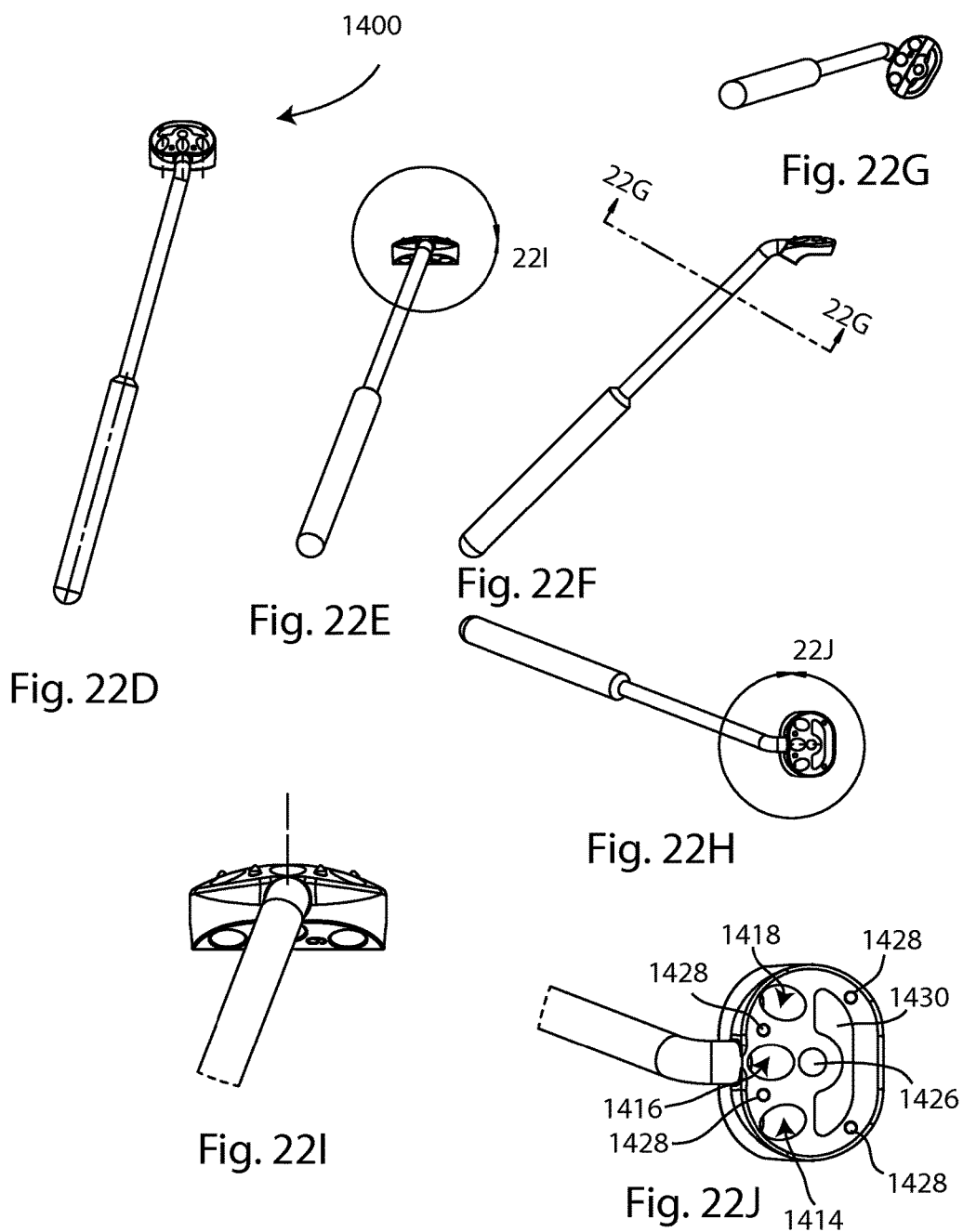

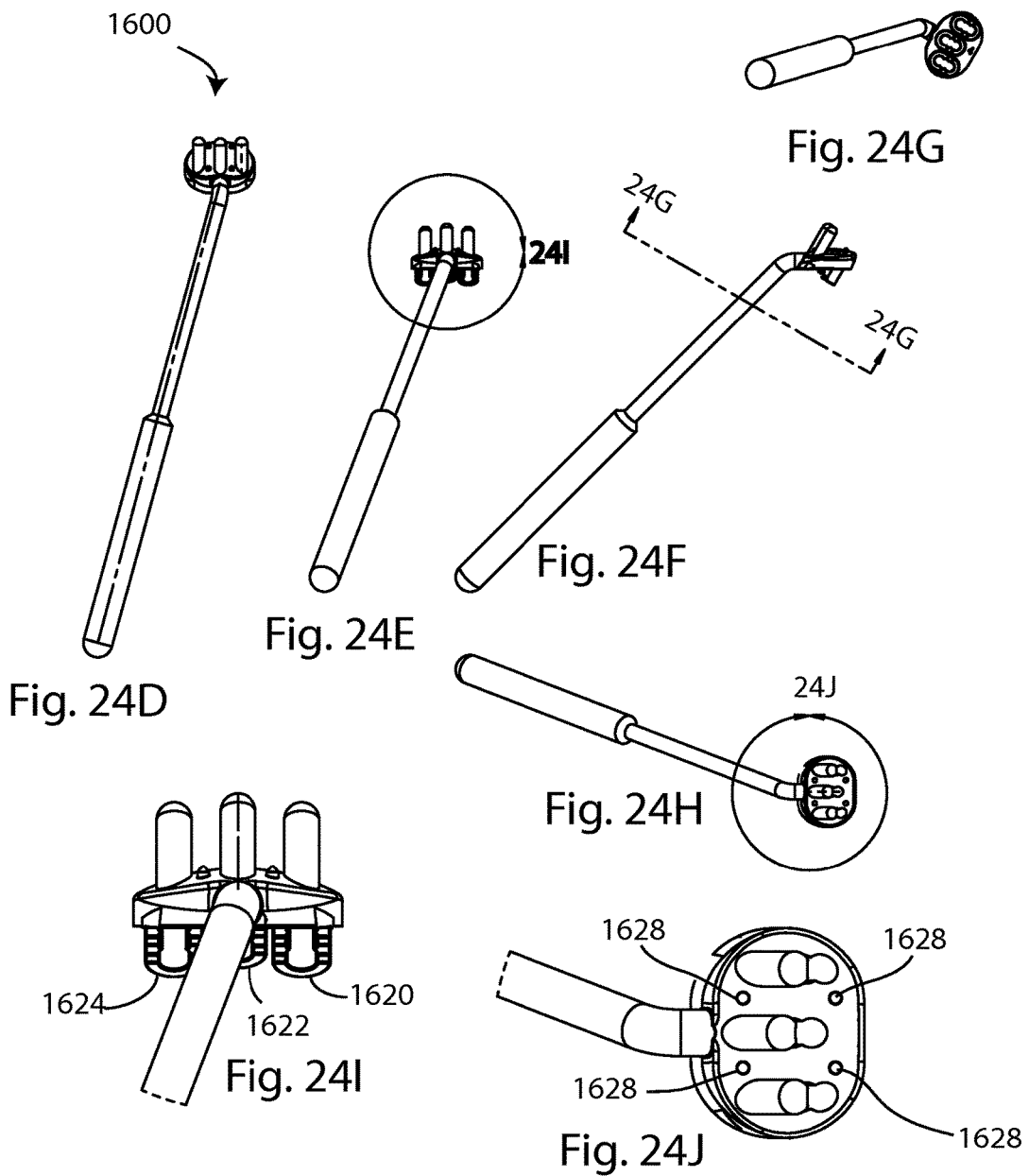

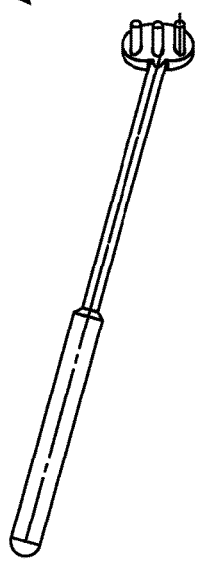
Fig. 27D
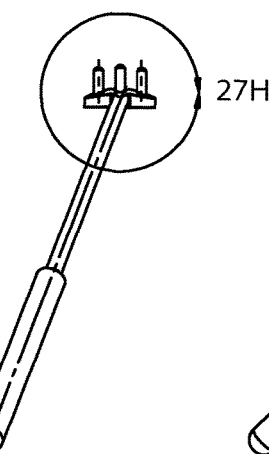
Fig. 27E
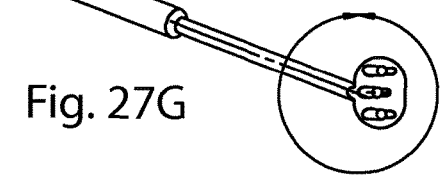
Fig. 27F
Fig. 27G
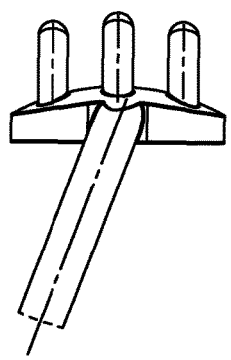
Fig. 27H
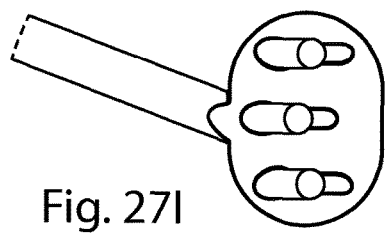
Fig. 27I

GLENOID ARTHROPLASTY

CROSS-REFERENCE TO RELATED APPLICATIONS

This application claims the benefit of:
U.S. Provisional Patent Application No. 61/776,398, filed Mar. 11, 2013, entitled OBLIQUE INSERTION ANCHORING MECHANISM FOR SHOULDER PROSTHETIC COMPONENT.

The above-identified document is incorporated herein by reference in its entirety.

BACKGROUND

The present disclosure relates to anchoring elements and articular surfaces for human or veterinary implants. The disclosed anchoring elements are useful in situations where exposure is difficult, the implantation trajectory is oblique to the implantation site, or the implantation site is tapered, conical, or wedge-shaped. For example, the disclosed anchoring elements are useful in the context of a glenoid implant for shoulder arthroplasty, so that the preparation of the glenoid and implantation of the glenoid component take place along an oblique surgical access and implantation trajectory. An oblique approach, or an antero-lateral approach, to the glenoid is technically simpler and less invasive than a lateral trajectory to the glenoid. This disclosure is made in the context of a glenoid component for shoulder arthroplasty for the purpose of illustrating the relevant principles of the technology.

In total shoulder arthroplasty, a glenoid implant is attached to a prepared glenoid or scapula, and a humeral implant is attached to a prepared humerus. The humeral implant usually includes a ball or convex articular surface at a proximal end thereof which engages and moves relative to a socket or concave articular surface formed in a lateral aspect of the glenoid implant, although this arrangement is sometimes reversed so that the humeral implant includes the concave articular surface and the glenoid implant includes the convex articular surface. The ligaments and muscles of the shoulder surround the implants and maintain the humeral implant against the glenoid implant, while at the same time allowing relative movement therebetween.

Current implants frequently have a central peg or keel, occasionally with two or three small peripheral supporting pegs. These implants rely on the centrally placed anchoring element to provide the majority of the fixation. In situations where the surgeon encounters bone defects, bone cysts, or where a prior component has been removed, there is often a central defect in the bone where fixation is not possible.

Current instruments for standard glenoid arthroplasty, including drill bits, reamers, and trial implant components, and final implant components are frequently designed for the surgeon to approach the scapula along a direction perpendicular to the face of the glenoid portion of the scapula; this may be referred to as a direct lateral trajectory. However, the standard incisions and safest surgical approach for glenoid arthroplasty provide exposure for the surgeon which is more oblique, or antero-lateral. In order to facilitate the insertion of instruments perpendicular to the face of the glenoid, the surgeon may find it necessary to resect the articular portion of the humeral head and forcefully retract the patient's skin, muscle and remaining humerus out of the way posteriorly to obtain adequate exposure. In doing so, the surgeon may potentially injure nerves or blood vessels. Often the surgeon will purposely cut the biceps tendon or portions of the pectoralis major tendon to improve exposure to facilitate this step, as well as releasing the glenohumeral ligaments. All of this dissection, retraction, and removal of bone and soft tissue is done in order to allow the surgeon enough room to implant the glenoid prosthetic component.

Thus, there is a need for an implant anchoring mechanism that can be inserted from an oblique angle to allow for a less invasive and technically simpler surgical operation, for example, for anchoring a glenoid prosthetic component to scapular bone.

The present disclosure sets forth an oblique-insertion anchoring mechanism for securing a glenoid prosthetic component to scapular bone. The anchoring mechanism can be inserted from an oblique angle to allow for a less invasive and technically simpler surgical operation. The anchoring mechanism is formed from a rounded dowel which projects from the medial aspect of a glenoid prosthetic component. The dowel projects at an angle which is not perpendicular to, or normal to, the medial side of the glenoid component, but is instead an acute angle less than 90 degrees. In the acute angle between the dowel and the medial side of the glenoid component there is a triangular reinforcement plate which buttresses the dowel and arises at a supplementary angle from the medial side of the glenoid component. The dowel and the edge of the reinforcement plate meet at the apex of the triangle.

It is contemplated that the number and location or placement of the anchoring elements will vary to accommodate different clinical situations.

The anchoring elements disclosed herein may be placed peripherally in a ring orientation, avoiding a bony central defect. Anchoring elements placed more peripherally provide more resistance to the effects of shear forces caused by the pressure of the humeral head during edge loading, as the distance and resultant lever arm decrease.

Biomechanically, the triangular arrangement of the dowel with the reinforcement plate allows the anchoring element to stabilize the body of the prosthesis from both legs of the triangular base to protect against both anterior and posterior eccentric forces. The triangular base of the anchoring element provides balanced anchoring to resist the anterior and posterior directed forces. The disclosed technology has fixation at both legs of the triangle, symmetric in distance from the edges of the body of the prosthesis, and all along the base of the triangle as well. The triangular shape also provides much larger surface area to resist superior and inferior directed forces than pegs alone. This is in contrast to a simple obliquely oriented peg which places the point of fixation of implant off center, allowing liftoff at the side farthest from the peg.

The disclosed design of the anchoring element may be even more preferable than traditional designs when glenoid deformity is present. Glenoid retroversion and glenoid vault bone loss are commonly seen in cases of advanced arthritis and the present design better fits the bony anatomy in these cases. This technology may also be preferable for revision glenoid arthroplasty operations.

The anchoring elements disclosed herein allow the prosthetic component to be inserted at an oblique angle. Therefore, there is less need to forcefully retract bone or soft tissues to obtain adequate exposure. The surgeon may be able to implant the prosthetic component without cutting the pectoralis major, the biceps tendon, or the glenohumeral ligaments. These tendons and ligaments serve as static and dynamic stabilizers of the humeral head during normal motion. If left intact, humeral motion remains more controlled and centered, reducing the incidence of humeral translation and contact with the far peripheral edges of the glenoid component. Reducing edge-loading results in less loosening forces transmitted to the anchoring elements, which is a common mode of failure of glenoid prosthetic components and total shoulder arthroplasty overall. Furthermore, the surgeon may not be compelled to resect the humeral head and may choose instead to use a bone-preserving humeral resurfacing arthroplasty component during the operation, which may further reduce operative time, blood loss and bone removal.

The inferior chamfer design of the lateral bearing surface of the glenoid component minimizes the incidence of impingement between the humeral component and the inferior articular margin of the glenoid prosthesis, thus reducing the likelihood of implant loosening and wear. Humeral impingement on the inferior glenoid is reported to be a cause of implant loosening and wear. Retrieval studies of loose failed glenoid implants have repeatedly demonstrated deformation at this inferior location.

For at least these reasons, the disclosed technology may simplify the operation, shorten the length of the operation, reduce soft-tissue dissection, reduce risk of neurovascular injury, reduce blood loss, reduce the need for bone resection, and may improve implant longevity.

Preservation of soft-tissues in glenoid preparation, optionally combined with the use of a humeral resurfacing component, may make shoulder arthroplasty more appealing for younger patients with significant degenerative disease, a patient group currently generally discouraged from undergoing shoulder arthroplasty.

An objective of the technology is to disclose a unique positioning of a dowel with planar buttress element in a glenoid prosthetic component.

Another objective of the technology is to disclose an improved glenoid prosthetic component that permit placement of anchoring elements in locations to better replicate normal human anatomy.

Yet another objective of the technology is to disclose an improved glenoid component that is inserted obliquely.

Yet another objective of the technology is to disclose an improved glenoid component having a dowel designed to match the specific anatomic shape of the surrounding bone.

Yet another objective of the technology is to disclose an improved glenoid prosthetic component having unique differential radius of curvature in the superior-inferior and anterior-posterior directions.

Yet another objective of the technology is to disclose an improved glenoid prosthetic component having a unique inferior chamfer.

Other objectives and advantages of this technology will become apparent from the following description taken in conjunction with the accompanying drawings which illustrate examples of this technology. The drawings constitute a part of this specification and include examples of the present technology and illustrate various objects and features thereof.

BRIEF DESCRIPTION OF THE DRAWINGS

While examples of the present technology are shown and described in detail below, it will be clear to the person skilled in the art that variations, changes and modifications may be made without departing from its scope. As such, that which is set forth in the following description and accompanying drawings is offered by way of illustration only and not as a limitation. The actual scope of the invention is intended to be defined by the following claims, along with the full range of equivalents to which such claims are entitled.

Identical reference numerals do not necessarily indicate an identical structure. Rather, the same reference numeral may be used to indicate a similar feature or a feature with similar functionality. Not every feature of each example is labeled in every figure in which that example appears, in order to keep the figures clear. Similar reference numbers (e.g., those that are identical except for the first numeral) are used to indicate similar features in different examples.

FIG. 1A is a superior-posterior-medial view of a glenoid component; FIG. 1B is a superior-anterior-medial view of the glenoid component of FIG. 1A; FIG. 1C is a medial view of the glenoid component of FIG. 1A; FIG. 1D is an inferior-posterior-medial view of the glenoid component of FIG. 1A; and FIG. 1E is an inferior-anterior-medial view of the glenoid component of FIG. 1A;

FIG. 12A is a superior-anterior-lateral view of the glenoid component of FIG. 11A; FIG. 12B is a superior-posterior-lateral view of the glenoid component of FIG. 11A; FIG. 12C is a lateral view of the glenoid component of FIG. 11A; FIG. 12D is an inferior-anterior-lateral view of the glenoid component of FIG. 11A; and FIG. 12E is an inferior-posterior-lateral view of the glenoid component of FIG. 11A;

FIG. 17A is a superior-posterior-medial view of yet another glenoid component; FIG. 17B is a posterior view of the glenoid component of FIG. 17A; FIG. 17C is an inferior view of the glenoid component of FIG. 17A; FIG. 17D is a medial view of the glenoid component of FIG. 17A; FIG. 17E is a cross sectional view of the glenoid component of FIG. 17A, taken along section line 17E-17E of FIG. 17D; and FIG. 17F is an anterior view of the glenoid component of FIG. 17A;

FIG. 19G is a posterior view of the glenoid component of FIG. 19A; FIG. 19H is an inferior view of the glenoid component of FIG. 19A; FIG. 19I is a superior view of the glenoid component of FIG. 19A; FIG. 19J is a medial view of the glenoid component of FIG. 19A; FIG. 19K is a cross sectional view of the glenoid component of FIG. 19J, taken along section line 19K-19K of FIG. 19J; and FIG. 19L is a cross sectional view of the glenoid component of FIG. 19J, taken along section line 19L-19L of FIG. 19J;

FIG. 22D is yet another isometric view of the drill guide of FIG. 22A from a different direction; FIG. 22E is yet another isometric view of the drill guide of FIG. 22A from a different direction; FIG. 22F is another side view of the drill guide of FIG. 22A; FIG. 22G is a projected view of the drill guide of FIG. 22A, from projection line 22G-22G of FIG. 22F; FIG. 22H is yet another isometric view of the drill guide of FIG. 22A from a different direction; FIG. 22I is a detail view of a working portion of the drill guide of FIG. 22A, as indicated by detail circle 22I of FIG. 22E; and FIG. 22J is a detail view of a working portion of the drill guide of FIG. 22A, as indicated by detail circle 22J of FIG. 22H;

FIG. 24D is yet another isometric view of the drill guide of FIG. 24A from a different direction; FIG. 24E is yet another isometric view of the drill guide of FIG. 24A from a different direction; FIG. 24F is another side view of the drill guide of FIG. 24A; FIG. 24G is a projected view of the drill guide of FIG. 24A, from projection line 24G-24G of FIG. 24F; FIG. 24H is yet another isometric view of the drill guide of FIG. 24A from a different direction; FIG. 24I is a detail view of a working portion of the drill guide of FIG. 24A, as indicated by detail circle 24I of FIG. 24E; FIG. 24J is a detail view of a working portion of the drill guide of FIG. 24A, as indicated by detail circle 24J of FIG. 24H.

FIG. 27D is yet another isometric view of the punch of FIG. 27A from a different direction; FIG. 27E is yet another isometric view of the punch of FIG. 27A from a different direction; FIG. 27F is another side view of the punch of FIG. 27A; FIG. 27G is yet another isometric view of the punch of FIG. 27A from a different direction; FIG. 27H is a detail view of a working portion of the punch of FIG. 27A, as indicated by detail circle 27H of FIG. 27E; and FIG. 27I is a detail view of a working portion of the punch of FIG. 27A, as indicated by detail circle 27I of FIG. 27G;

DETAILED DESCRIPTION

Figure 2A:
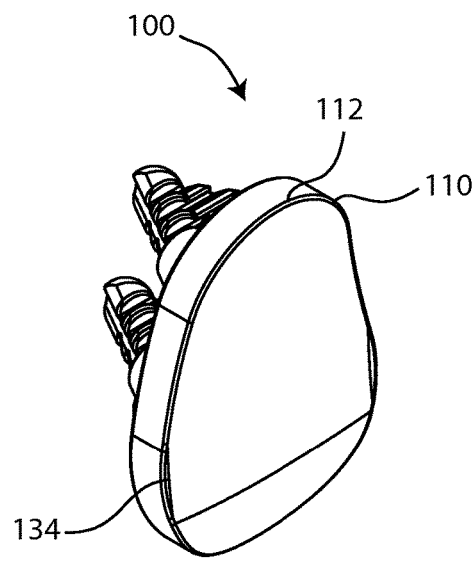
FIG. 2A is a superior-anterior-lateral view of the glenoid component of FIG. 1A.
Figure 2B:
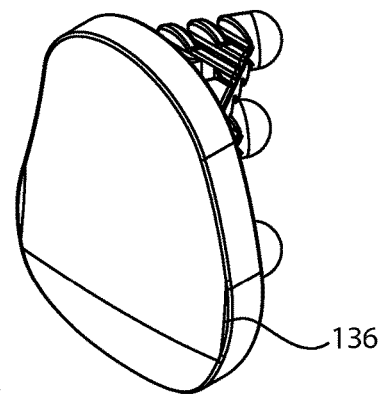
FIG. 2B is a superior-posterior-lateral view of the glenoid component of FIG. 1A.
Figure 2C:
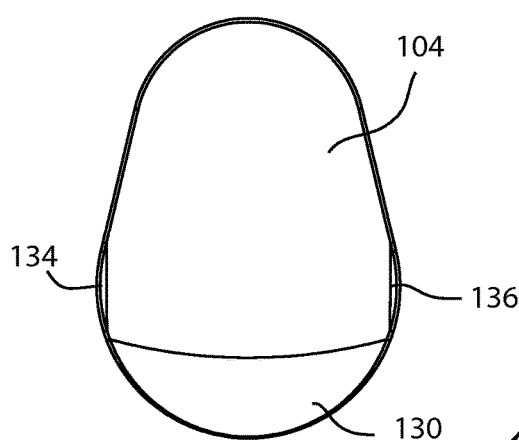
FIG. 2C is a lateral view of the glenoid component of FIG. 1A.
Figure 2D:
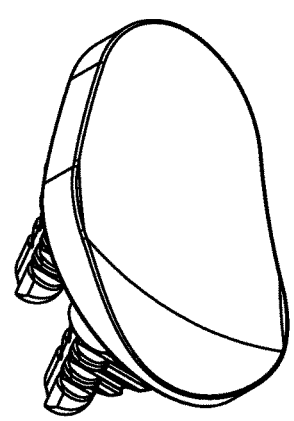
FIG. 2D is an inferior-anterior-lateral view of the glenoid component of FIG. 1A.
Figure 2E:
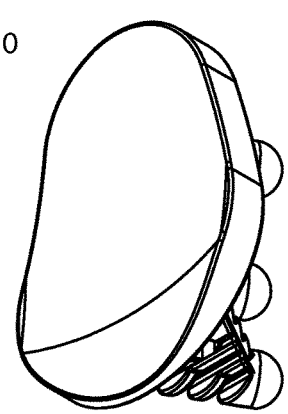
FIG. 2E is an inferior-posterior-lateral view of the glenoid component of FIG. 1A.
Figure 3A:
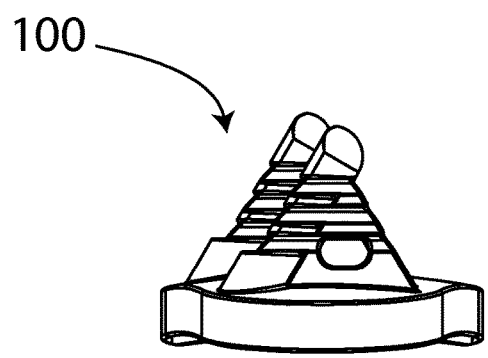
FIG. 3A is a superior view of the glenoid component of FIG. 1A.
Figure 3B:
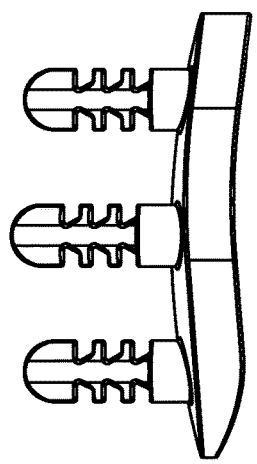
FIG. 3B is an anterior view of the glenoid component of FIG. 1A.
Figure 3C:
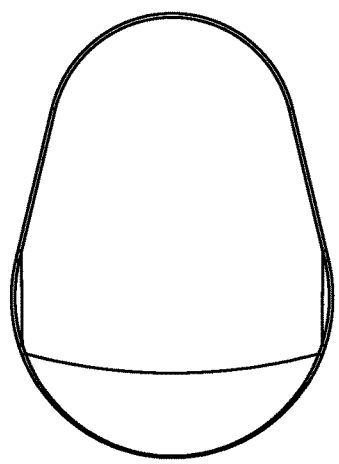
FIG. 3C is a lateral view of the glenoid component of FIG. 1A.
Figure 3D:
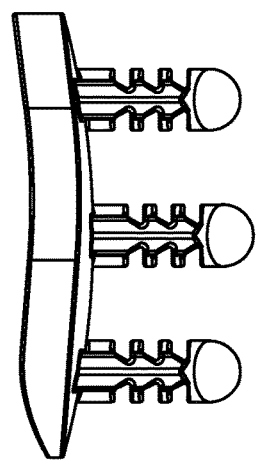
FIG. 3D is a posterior view of the glenoid component of FIG. 1A.
Figure 3E:
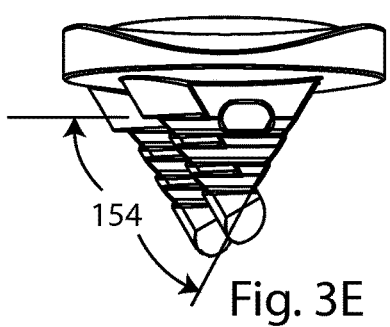
FIG. 3E is an inferior view of the glenoid component of FIG. 1A.
Figure 4A:
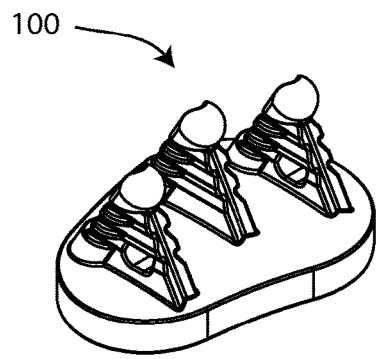
FIG. 4A is a superior-posterior-medial view of the glenoid component of FIG. 1A.
Figure 4B:
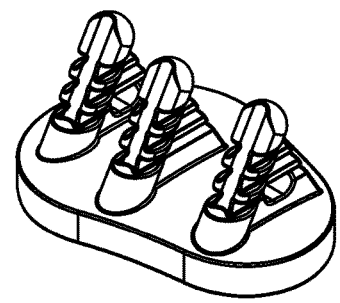
FIG. 4B is a superior-anterior-medial view of the glenoid component of FIG. 1A.
Figure 4C:
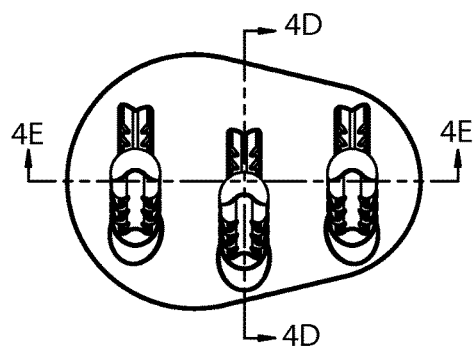
FIG. 4C is a medial view of the glenoid component of FIG. 1A.
Figure 4D:
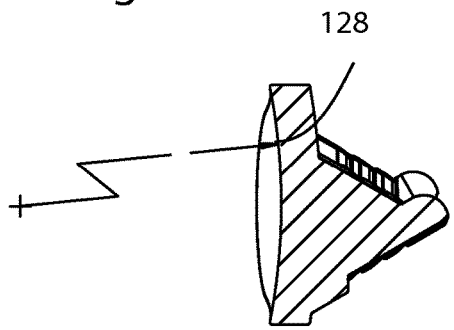
FIG. 4D is a cross sectional view of the glenoid component of FIG. 1A, taken along section line 4D-4D of FIG. 4C.
Figure 4E:
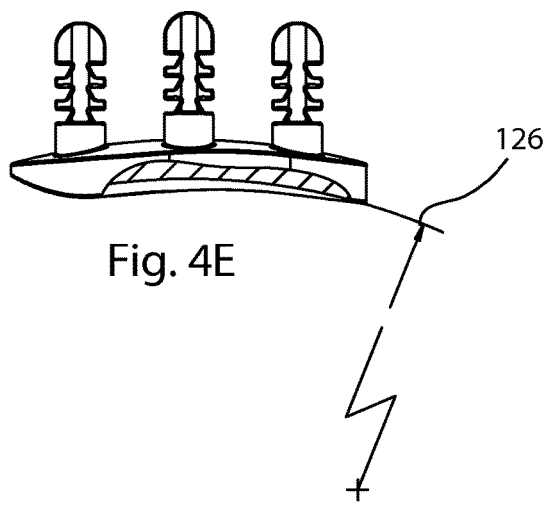
FIG. 4E is an anterior partial cross sectional view of the glenoid component of FIG. 1A, taken along section line 4E-4E of FIG. 4C.
Figure 4F:
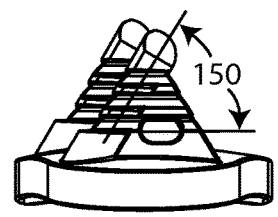
FIG. 4F is a superior view of the glenoid component of FIG. 1A.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

Referring to FIGS. 1A-4F, a glenoid component 100 includes a body 102 with a lateral articular surface 104 and an opposite medial bone-facing surface 106.

A peripheral wall 108 extends around the body 102 between the surfaces 104, 106. A lateral peripheral edge 110 extends around the body 102 where the lateral articular surface 104 meets the peripheral wall 108. The lateral peripheral edge 110 may include a lateral peripheral relief 112, such as a radius, fillet, chamfer, bevel, or the like. The lateral peripheral relief 112 may reduce point loading of a corresponding humeral articular surface at the lateral peripheral edge 110. A medial peripheral edge 114 extends around the body 102 where the medial bone-facing surface 106 meets the peripheral wall 108. The medial peripheral edge 114 may include a medial peripheral relief 116, such as a radius, fillet, chamfer, bevel, or the like.

The body 102 may be divided into a superior portion 118, an inferior portion 120, an anterior portion 122, and a posterior portion 124. These terms 118, 120, 122, 124 may also be used in reference to the peripheral wall 108. In examples other than shoulder glenoid components, the appropriate medical directional terms may be readily substituted by one of skill in the art.

The lateral articular surface 104 may be concave as shown, planar, or convex in order to complement a natural or prosthetic humeral articular surface. The lateral articular surface 104 may be spherical. Alternatively, with reference to FIGS. 4C-4E, the lateral articular surface 104 may have a first radius 126 which is dimensionally different from a second radius 128. The first radius 126 may be larger or smaller than the second radius 128. In the example shown, the first radius 126 lies on a first plane which extends normal to the lateral articular surface 104 in the superior-inferior and medial-lateral directions and is centered in the anterior-posterior width of the body 102, as can be seen with reference to FIGS. 4C and 4E. The first radius 126 may be referred to as an S-I radius. The second radius 128 lies on a second plane which extends normal to the lateral articular surface 104 in the anterior-posterior and medial-lateral directions and is centered in the superior-inferior length of the body 102, as can be seen with reference to FIGS. 4C and 4D. The second radius may be referred to as an A-P radius. The first and second radii 126, 128 may lie on planes that are eccentrically located relative to the S-I length and A-P width of the body 102, that intersect at an acute or perpendicular angle, or that are oriented without regard to standard orthogonal planes of reference.

When the first radius 126 is dimensionally different from the second radius 128, the corresponding humeral articular surface is less constrained in the direction of the larger radius. For example, when the S-I radius 126 is larger than the A-P radius 128, the humeral articular surface is less constrained in the S-I direction than in the A-P direction. Less constraint may result in lower eccentric forces applied to the glenoid articular surface 104, and thus reduced risk of implant loosening. A glenoid articular surface 104 in which the S-I radius 126 is larger than the A-P radius 128 may therefore exhibit improved performance when tested according to ASTM F-2028, "Standard Test Methods for Dynamic Evaluation of Glenoid Loosening or Disassociation."

The inferior portion 120 of the body 102 may include an inferior chamfer 130 which extends between the lateral articular surface 104 and the peripheral wall 108. The inferior chamfer 130 lowers the profile and thickness of the inferior portion 120. This arrangement lessens the risk of impingement between a corresponding humerus and the inferior portion 120. The inferior chamfer 130 and rounded edges 112, 116 on the lateral articular surface 104 may reduce microscopic cracking and wear of the body 102. This may reduce the formation of particulate debris which is associated with inflammatory reactions in the local tissue, osteolysis, and component loosening.

The anterior portion 122 of the body 102 may include an anterior relief 134 which extends between the lateral articular surface 104 and the peripheral wall 108. The anterior relief 134 lowers the profile and thickness of the anterior portion 122. Similarly, the posterior portion 124 of the body 102 may include a posterior relief 136 which extends between the lateral articular surface 104 and the peripheral wall 108. The posterior relief 136 lowers the profile and thickness of the posterior portion 124.

The medial bone-facing surface 106 may be convex as shown, planar, or concave.

The glenoid component 100 includes at least one anchoring element 138 which protrudes outwardly from the medial bone-facing surface 106. The example shown includes a superior anchoring element 138, an inferior anchoring element 140, and a middle anchoring element 142, although any number of anchoring elements may be present. The middle anchoring element 142 is positioned slightly anterior to the other anchoring elements 138, 140 in order to more closely match the normal anatomy of the glenoid vault. Each anchoring element may be independently positioned on the medial bone-facing surface 106, and may be independently sized.

The anchoring element 138 includes a dowel 148 and a triangular reinforcement plate 152. The dowel may also be referred to as a mast. The reinforcement plate may also be referred to as a sail or buttress. The dowel 148 projects from the medial bone-facing surface 106 at an angle 150 less than ninety degrees and greater than zero degrees. The angle 150 may be referred to as a dowel angle or a mast angle. More specifically, the angle 150 may be measured between a central longitudinal axis of the dowel 148 and a plane which is tangent to the medial bone-facing surface 106, if surface 106 is concave or convex, or a plane which is coplanar with the medial bone-facing surface 106, if surface 106 is planar. For example, the plane may be tangent to the medial bone-facing surface 106 at an intersection point between the central longitudinal axis of the dowel 148 and the medial bone-facing surface 106, or at a centroid of the medial bone-facing surface 106. The dowel 148 may project from the anterior portion 122 of the body 102, as shown, or from another portion of the body 102. In the example shown, the dowels 148 of anchoring elements 138, 140, 142 project from peripheral locations in the anterior portion 122 and terminate in medially located free ends. The dowel 148 may have a round basic cross sectional shape, as shown, or may be another shape, such as a rectangle or dovetail. The dowel 148 may include a hole (shown in later embodiments), which may receive a radiographic marker. The reinforcement plate 152 also projects from the medial bone-facing surface 106 in the acute angle 150 between the dowel 148 and the medial bone-facing surface 106, coplanar with the dowel 148. An exposed side of the reinforcement plate 152 projects from the medial bone-facing surface 106 at an angle 154 less than ninety degrees and greater than zero degrees. The angle 154 may be referred to as a supplementary angle or a reinforcement angle. The angle 154 opens toward the angle 150, and the sum of angles 150 and 154 is greater than zero degrees and less than one hundred eighty degrees. The reinforcement plate 152 intersects the dowel 148 to form a triangular shape with one side formed by the medial bone-facing surface 106, one side formed by the dowel 148, and one side formed by the exposed side of the reinforcement plate 152. The anchoring element 138 may include a pedestal 156 or footing which reinforces the base of the anchoring element 138 where it joins the medial bone-facing surface 106. The pedestal 156 may be described as an enlargement of the anchoring element 138, and may be present on the dowel 148 or the reinforcement plate 152, or both. Pedestal 156 as shown is present on the dowel 148. The pedestal 156 may terminate in a planar face 157 which establishes the plane from which the angles 150, 154 are measured. The planar face 157 may be tangent to the medial bone-facing surface 106 at a center point along the medial bone-facing surface side of the triangular shape.

The anchoring element 138 may include surface features to improve the pull-out strength after implantation. The surface features may be described as fixation features 158, and may include notches, ridges, barbs, threads, or perforations. For example, alternating ridges 160 and grooves 162 are shown, as well as fenestrations 168 in superior and inferior anchoring elements 138 and 140. All of these surface features may facilitate bony ingrowth or bone cement interdigitation.

A slot 164, or groove or channel may be present along the dowel side of the triangular shape, the reinforcement plate side of the triangular shape, or both. In cemented applications of the technology, the bone cement may flow along the slot(s) 164 on the anchoring element to facilitate more uniform and stronger fixation. The slot(s) 164, or channels, of the dowel 148 and/or the reinforcement plate 152 permit cement flow and promote cement interdigitation more evenly throughout the anchoring element and just below subchondral bone rather than pushing the cement to the deepest portion of the glenoid vault. In the example shown, the three-dowel glenoid component includes slots 164 along both the dowel side and the reinforcement plate side of the triangular shape. In other examples, a flat surface may extend along the dowel side of the triangular shape, the reinforcement plate side of the triangular shape, or both.

Figure 5A:
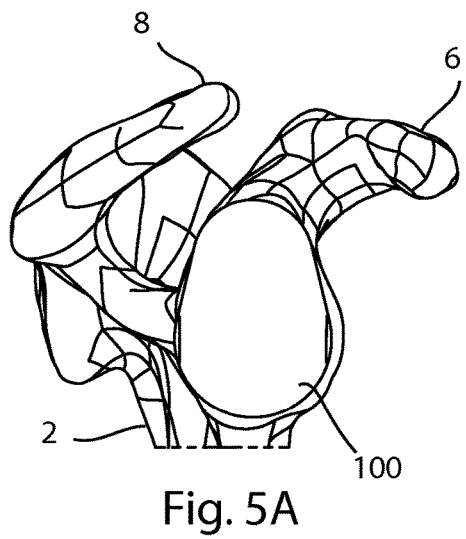
FIG. 5A is a lateral view of the glenoid component of FIG. 1A and a portion of a scapula, the glenoid component operatively implanted in the scapula.
Figure 5B:
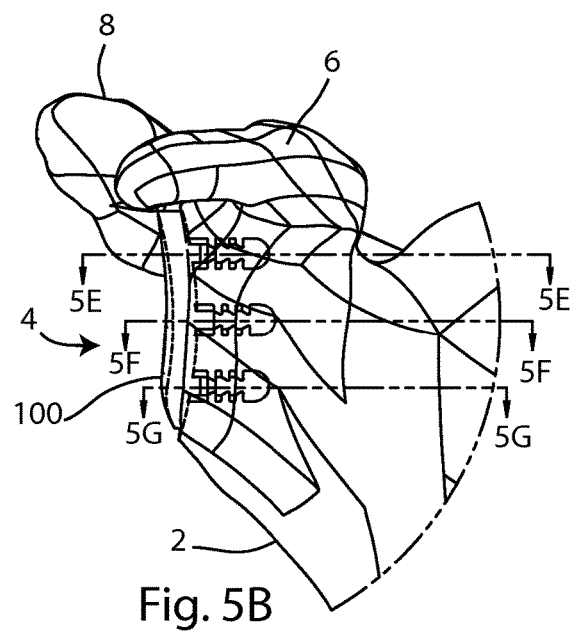
FIG. 5B is an anterior view of the glenoid component and scapula of FIG. 5A.
Figure 5C:
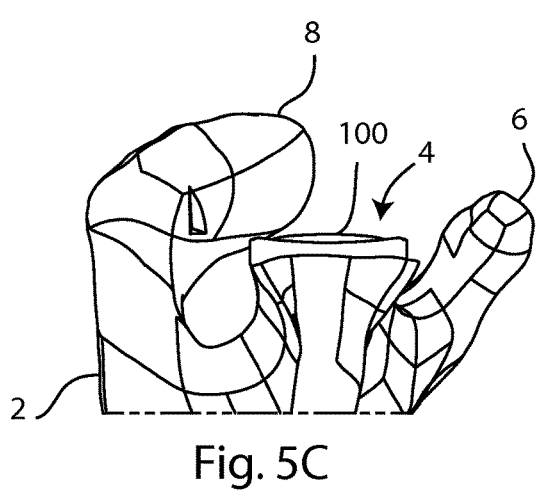
FIG. 5C is an inferior view of the glenoid component and scapula of FIG. 5A.
Figure 5D:
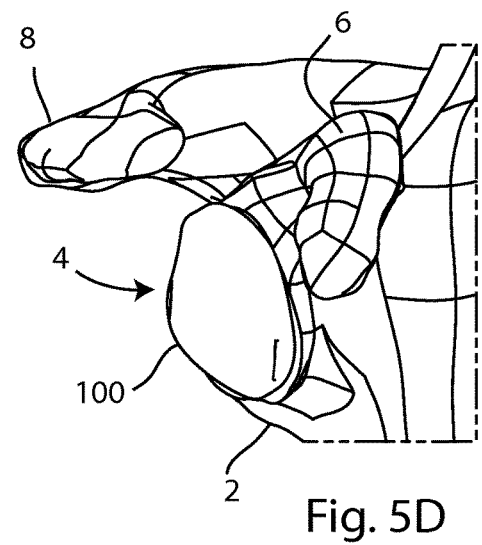
FIG. 5D is an anterior-lateral view of the glenoid component and scapula of FIG. 5A.
Figure 5E:
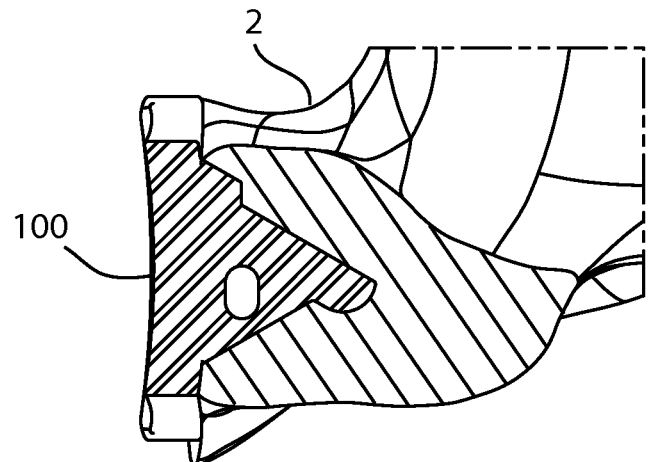
FIG. 5E is a cross sectional view of the glenoid component and scapula of FIG. 5A, taken along section line 5E-5E of FIG. 5B.
Figure 5F:
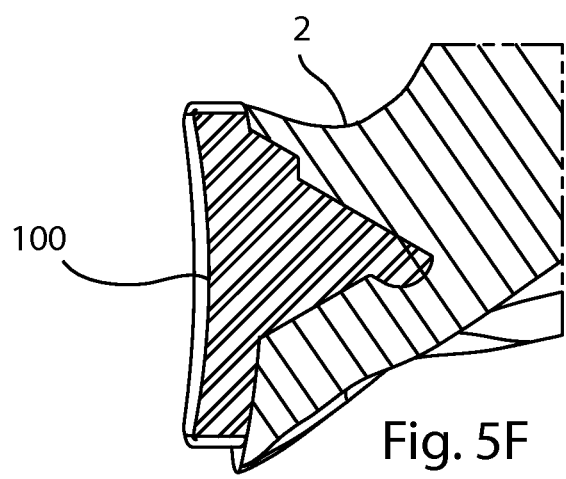
FIG. 5F is a cross sectional view of the glenoid component and scapula of FIG. 5A, taken along section line 5F-5F of FIG. 5B.
Figure 5G:
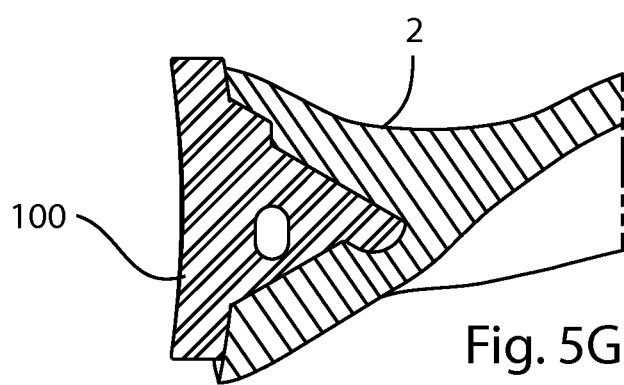
FIG. 5G is a cross sectional view of the glenoid component and scapula of FIG. 5A, taken along section line 5G-5G of FIG. 5B.
Figure 6A:
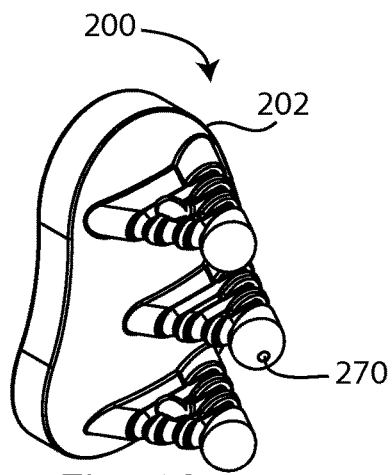
FIG. 6A is a superior-posterior-medial view of another glenoid component.
Figure 6B:
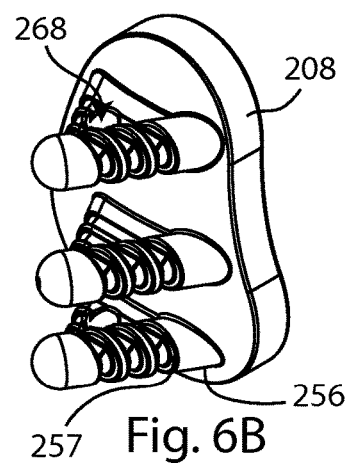
FIG. 6B is a superior-anterior-medial view of the glenoid component of FIG. 6A.
Figure 6C:
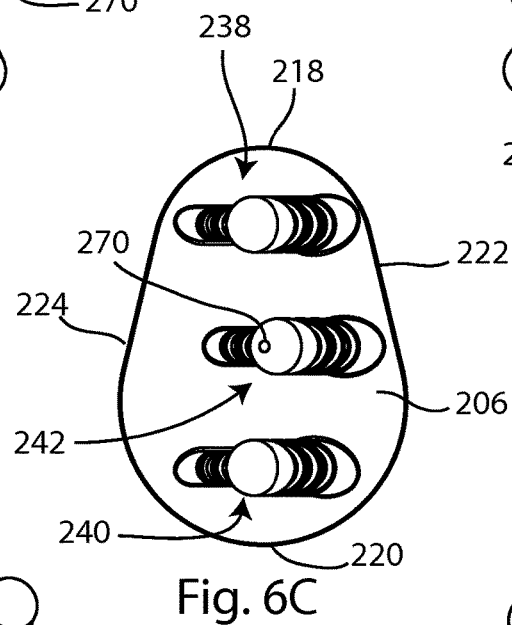
FIG. 6C is a medial view of the glenoid component of FIG. 6A.
Figure 6D:
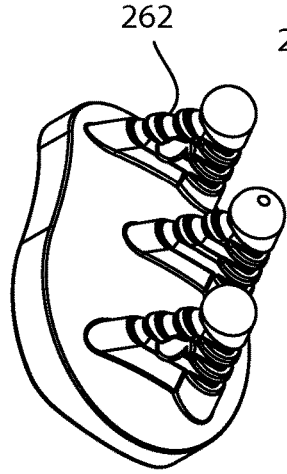
FIG. 6D is an inferior-posterior-medial view of the glenoid component of FIG. 6A.
Figure 6E:
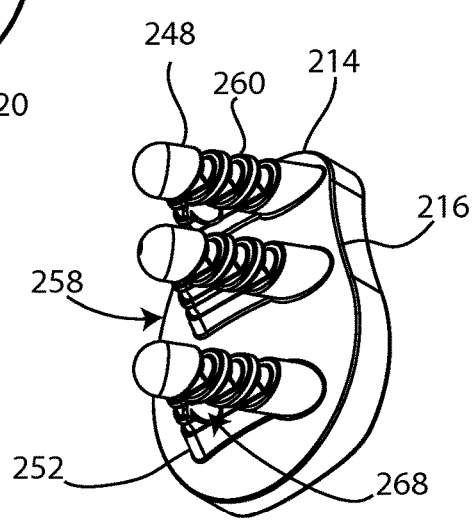
FIG. 6E is an inferior-anterior-medial view of the glenoid component of FIG. 6A.
Figure 7A:
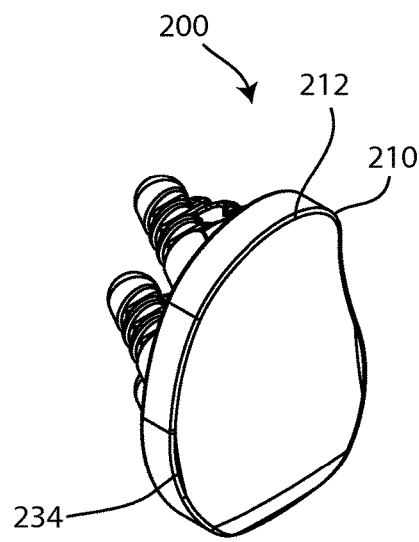
FIG. 7A is a superior-anterior-lateral view of the glenoid component of FIG. 6A.
Figure 7B:
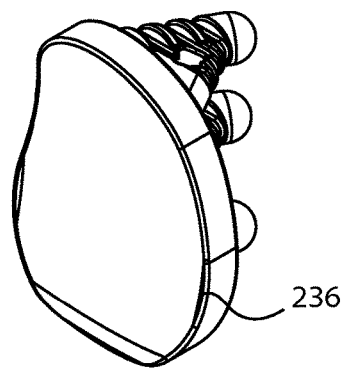
FIG. 7B is a superior-posterior-lateral view of the glenoid component of FIG. 6A.
Figure 7C:
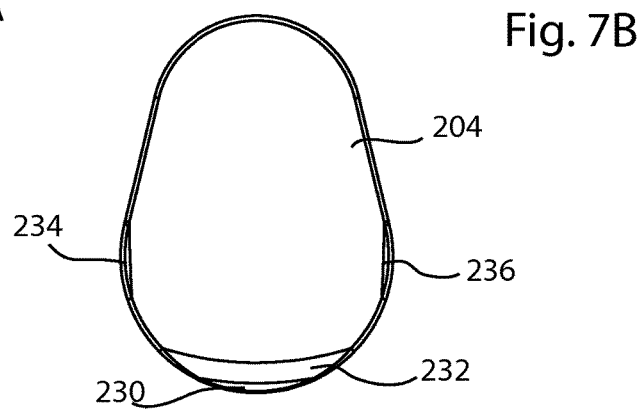
FIG. 7C is a lateral view of the glenoid component of FIG. 6A.
Figure 7D:
FIG. 7D is an inferior-anterior-lateral view of the glenoid component of FIG. 6A.
Figure 7E:
FIG. 7E is an inferior-posterior-lateral view of the glenoid component of FIG. 6A.
Figure 8A:
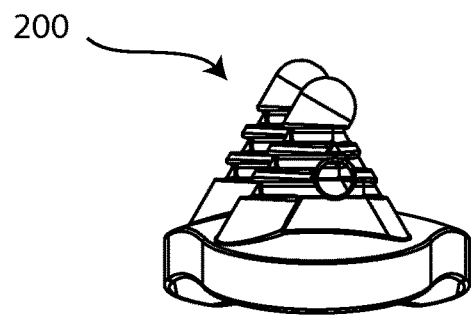
FIG. 8A is a superior view of the glenoid component of FIG. 6A.
Figure 8B:
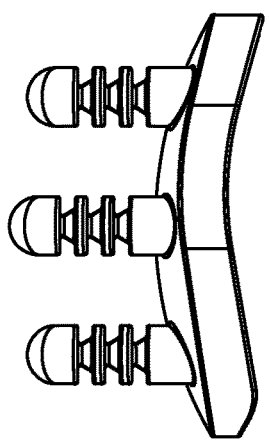
FIG. 8B is an anterior view of the glenoid component of FIG. 6A.
Figure 8C:
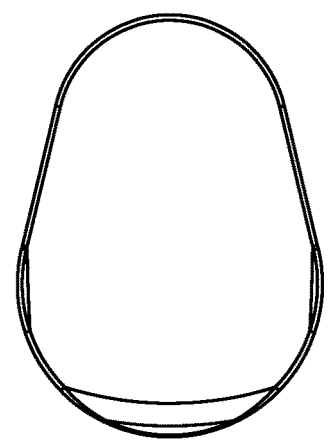
FIG. 8C is a lateral view of the glenoid component of FIG. 6A.
Figure 8D:
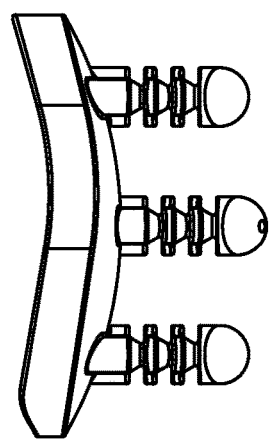
FIG. 8D is a posterior view of the glenoid component of FIG. 6A.
Figure 8E:
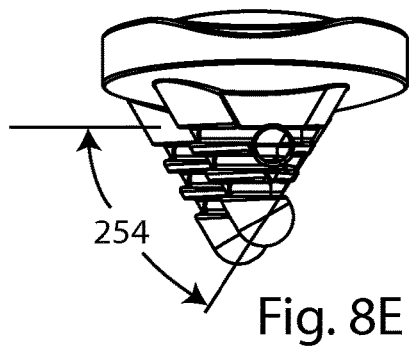
FIG. 8E is an inferior view of the glenoid component of FIG. 6A.
Figure 9A:
FIG. 9A is a superior-posterior-medial view of the glenoid component of FIG. 6A.
Figure 9B:
FIG. 9B is a superior-anterior-medial view of the glenoid component of FIG. 6A.
Figure 9C:
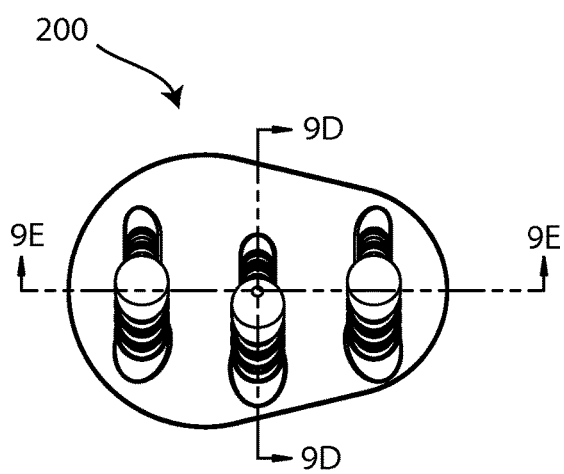
FIG. 9C is a medial view of the glenoid component of FIG. 6A.
Figure 9D:
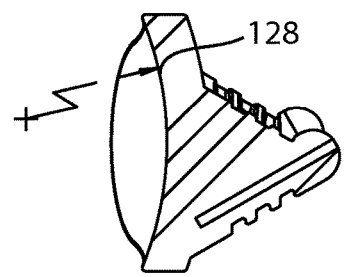
FIG. 9D is a cross sectional view of the glenoid component of FIG. 6A, taken along section line 9D-9D of FIG. 9C.
Figure 9E:
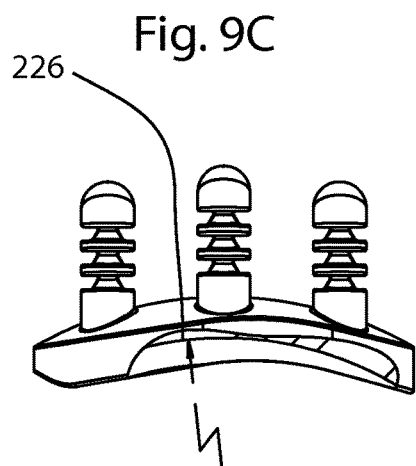
FIG. 9E is an anterior partial cross sectional view of the glenoid component of FIG. 6A, taken along section line 9E-9E of FIG. 9C.
Figure 9F:
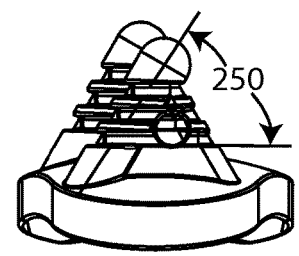
FIG. 9F is a superior view of the glenoid component of FIG. 6A.

Referring to FIGS. 5A-5G, the glenoid component 100 is shown operatively implanted in a scapula 2. The scapula 2 includes a glenoid fossa 4, a coracoid process 6, and an acromion process 8. FIGS. 5E-5G show various cross sections through the glenoid component 100 and the scapula 2. With reference to FIG. 5G, the triangular shape of the anchoring elements matches the conical shape of the glenoid vault more closely than does a central peg or keel. The triangular anchoring elements may be placed more peripherally on the glenoid component. The dowels 148 are peripherally arranged along the anterior portion 122 in the example shown. This places the base, or pedestal 156, of the anchoring elements into regions of denser subchondral bone for stronger fixation. Medially in the glenoid vault, the edges of the dowel and planar portions may lie adjacent and parallel to the thick cortical walls of the glenoid vault. Referring to FIG. 5F, the anterior location of the middle anchor element 142 more closely matches normal anatomy and allows the anchor element 142 to fit more precisely within the normal shape of the glenoid vault, due to the spinoglenoid notch. Better fit may result in reduced incidence of glenoid vault perforation by instruments and/or bone cement leakage through the cortical bone of the scapula into surrounding soft tissues.

Referring to FIGS. 6A-9F, a glenoid component 200 includes a body 202 with a lateral articular surface 204 and an opposite medial bone-facing surface 206. Glenoid component 200 includes the following features, which may be substantially similar to, or the same as, the corresponding features of glenoid component 100: peripheral wall 208, lateral peripheral edge 210, lateral peripheral relief 212, medial peripheral edge 214, medial peripheral relief 216, superior portion 218, inferior portion 220, anterior portion 222, posterior portion 224, S-I radius of curvature 226, A-P radius of curvature 228, inferior chamfer 230, anterior relief 234, posterior relief 236, superior anchoring element 238, inferior anchoring element 240, middle anchoring element 242, dowel or mast 248, mast angle 250, triangular reinforcement plate or sail 252, supplementary angle 254, pedestal 256, face 257, fixation feature 258, ridge 260, groove 262, and fenestration 268. Glenoid component 200 also includes a chamfer blend radius 232 and a hole 270. The chamfer blend radius 232 is adjacent to the inferior chamfer 230. The chamfer blend radius 232 is more centrally located than is the inferior chamfer 230. The hole 270 extends lengthwise into the dowel 248 of middle anchoring element 242, and may receive a radiographic marker (not shown). Glenoid component 200 lacks a slot, channel, or groove comparable to slot 164.

Figure 10A:
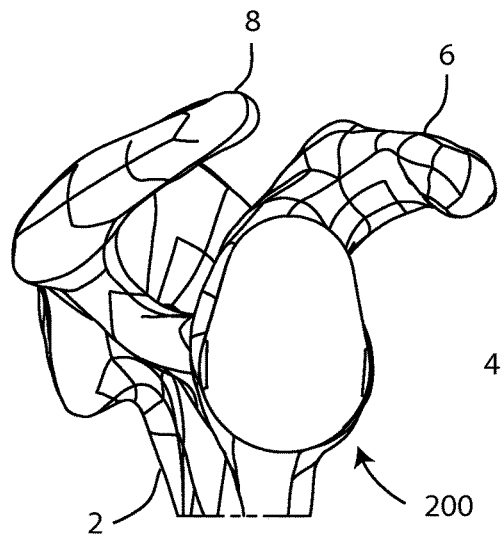
FIG. 10A is a lateral view of the glenoid component of FIG. 6A and a portion of a scapula, the glenoid component operatively implanted in the scapula.
Figure 10B:
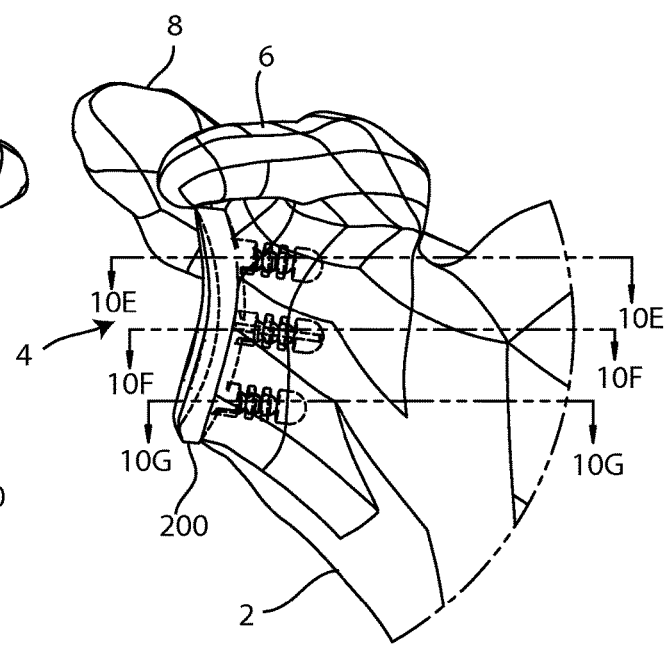
FIG. 10B is an anterior view of the glenoid component and scapula of FIG. 10A.
Figure 10C:
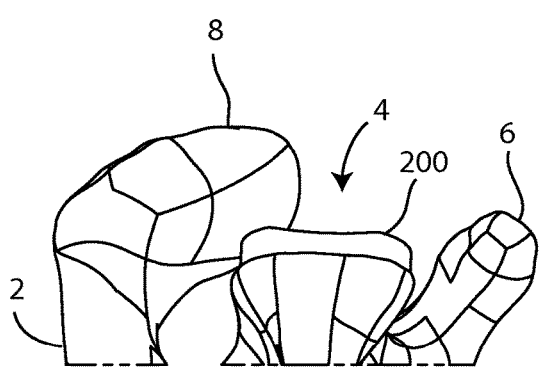
FIG. 10C is an inferior view of the glenoid component and scapula of FIG. 10A.
Figure 10D:
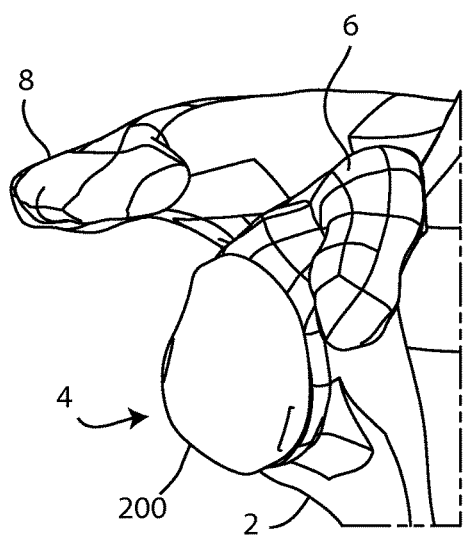
FIG. 10D is an anterior-lateral view of the glenoid component and scapula of FIG. 10A.
Figure 10E:
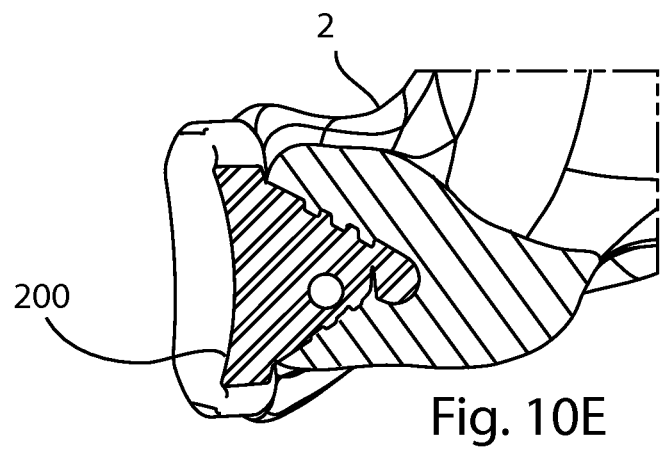
FIG. 10E is a cross sectional view of the glenoid component and scapula of FIG. 10A, taken along section line 10E-10E of FIG. 10B.
Figure 10F:
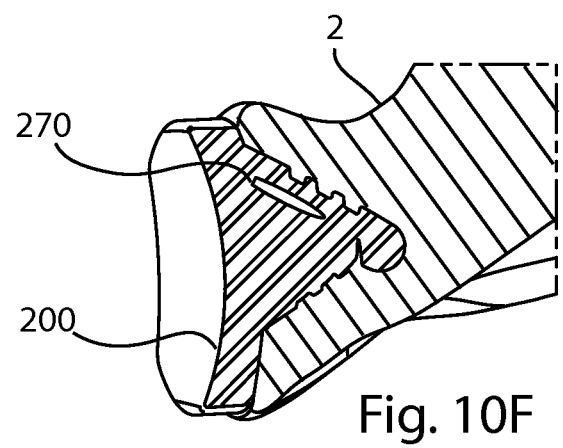
FIG. 10F is a cross sectional view of the glenoid component and scapula of FIG. 10A, taken along section line 10E-10F of FIG. 10B.
Figure 10G:
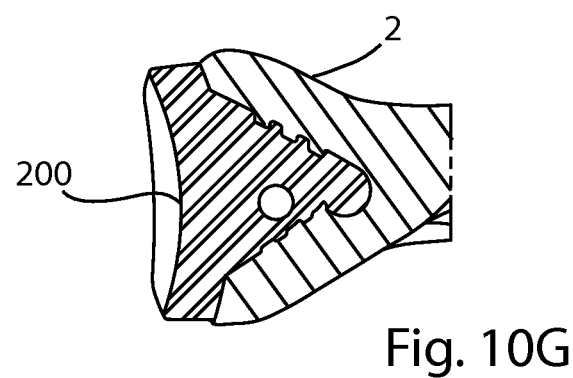
FIG. 10G is a cross sectional view of the glenoid component and scapula of FIG. 10A, taken along section line 10G-10G of FIG. 10B.
Figure 11A:
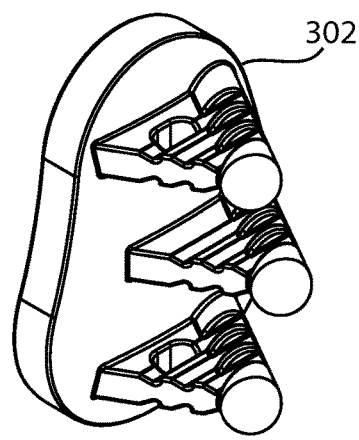
FIG. 11A is a superior-posterior-medial view of yet another glenoid component.
Figure 11B:
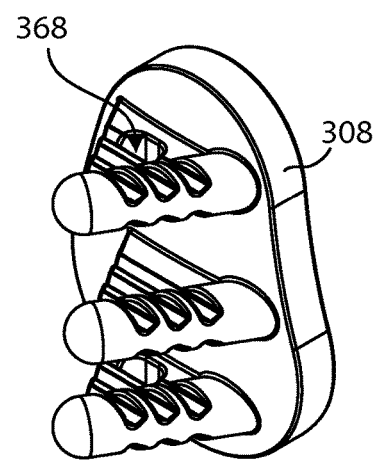
FIG. 11B is a superior-anterior-medial view of the glenoid component of FIG. 11A.
Figure 11C:
FIG. 11C is a medial view of the glenoid component of FIG. 11A.
Figure 11D:
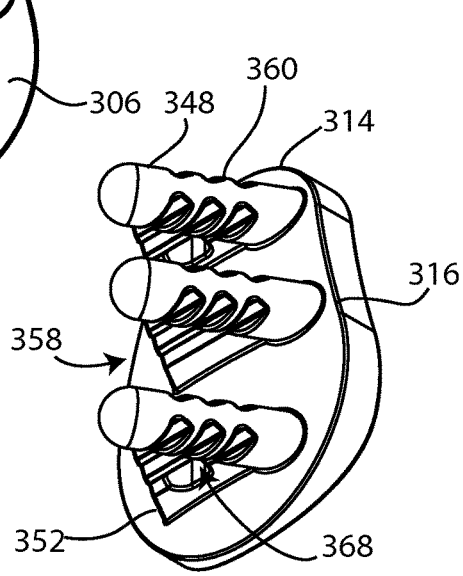
FIG. 11D is an inferior-posterior-medial view of the glenoid component of FIG. 11A.
Figure 11E:
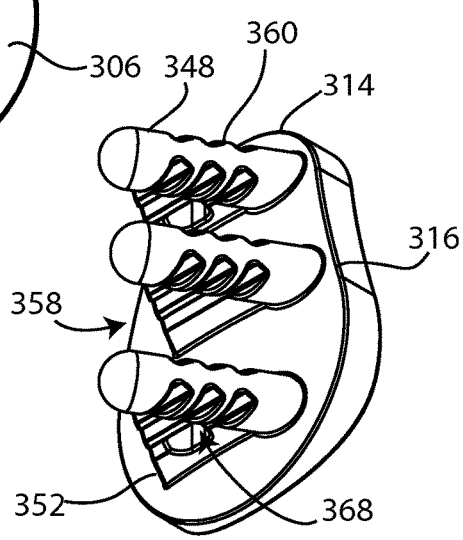
FIG. 11E is an inferior-anterior-medial view of the glenoid component of FIG. 11A.
Figure 13A:
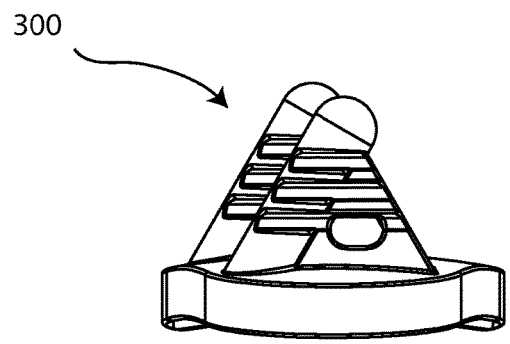
FIG. 13A is a superior view of the glenoid component of FIG. 11A.
Figure 13B:
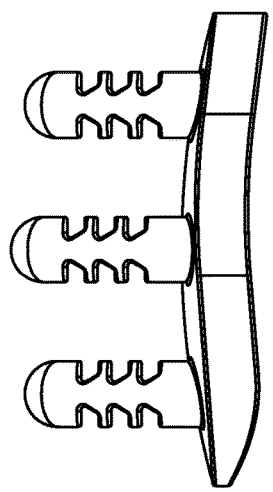
FIG. 13B is an anterior view of the glenoid component of FIG. 11A.
Figure 13C:
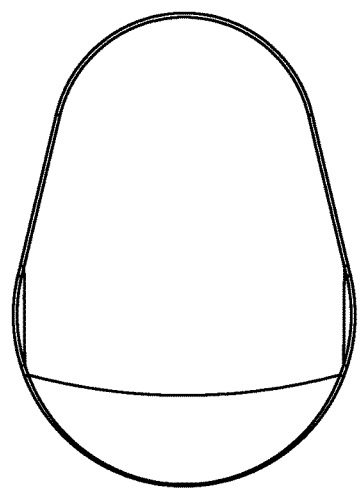
FIG. 13C is a lateral view of the glenoid component of FIG. 11A.
Figure 13D:
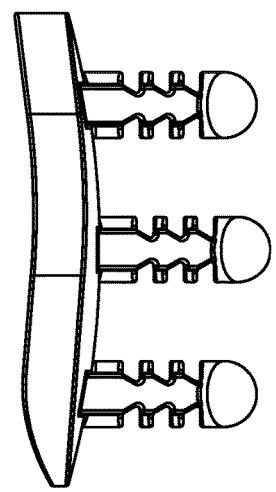
FIG. 13D is a posterior view of the glenoid component of FIG. 11A.
Figure 13E:
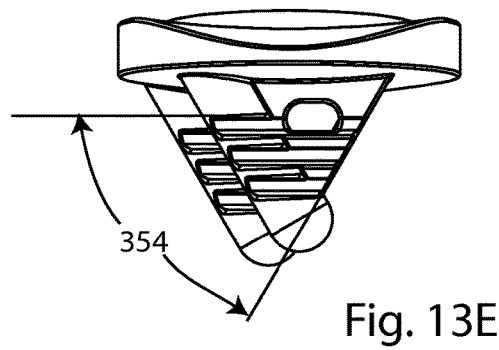
FIG. 13E is an inferior view of the glenoid component of FIG. 11A.
Figure 14A:
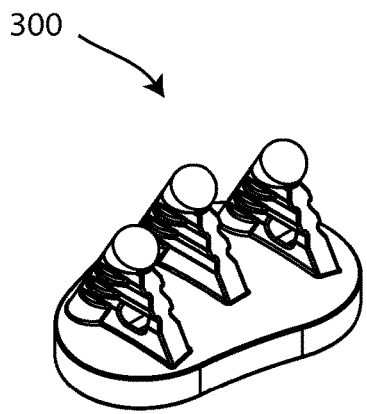
FIG. 14A is a superior-posterior-medial view of the glenoid component of FIG. 11A.
Figure 14B:
FIG. 14B is a superior-anterior-medial view of the glenoid component of FIG. 11A.
Figure 14C:
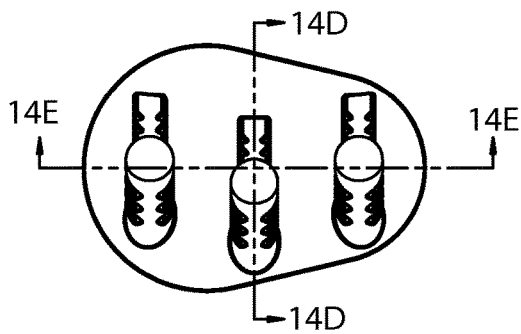
FIG. 14C is a medial view of the glenoid component of FIG. 11A.
Figure 14D:
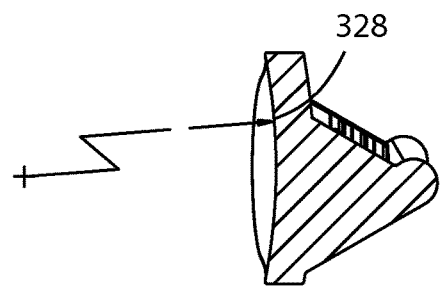
FIG. 14D is a cross sectional view of the glenoid component of FIG. 11A, taken along section line 14D-14D of FIG. 14C.
Figure 14E:
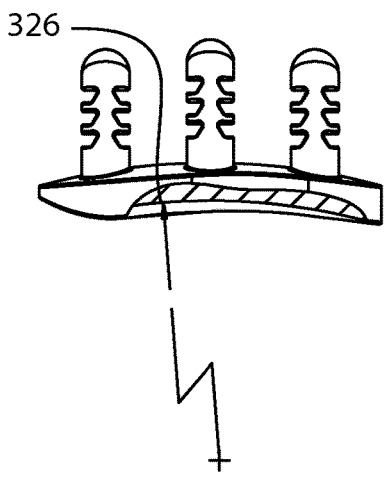
FIG. 14E is an anterior partial cross sectional view of the glenoid component of FIG. 11A, taken along section line 14E-14E of FIG. 14C.
Figure 14F:
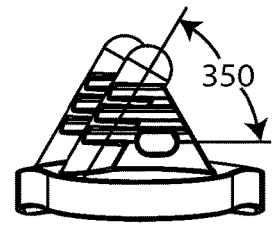
FIG. 14F is a superior view of the glenoid component of FIG. 11A.
Figure 15A:
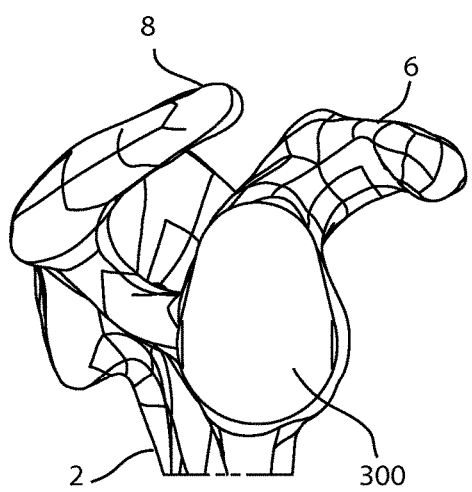
FIG. 15A is a lateral view of the glenoid component of FIG. 11A and a portion of a scapula, the glenoid component operatively implanted in the scapula.
Figure 15B:
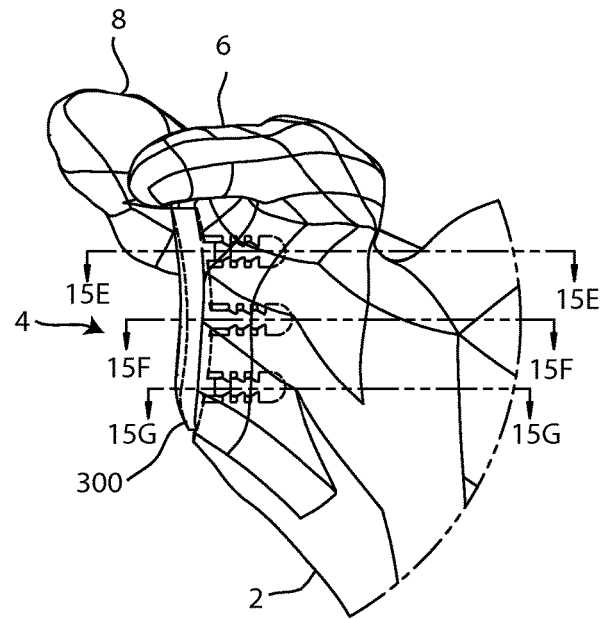
FIG. 15B is an anterior view of the glenoid component and scapula of FIG. 15A.
Figure 15C:
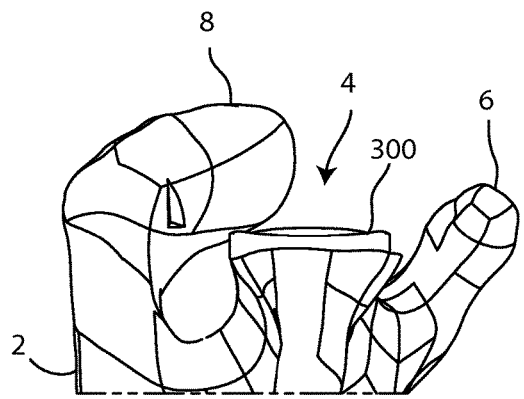
FIG. 15C is an inferior view of the glenoid component and scapula of FIG. 15A.
Figure 15D:
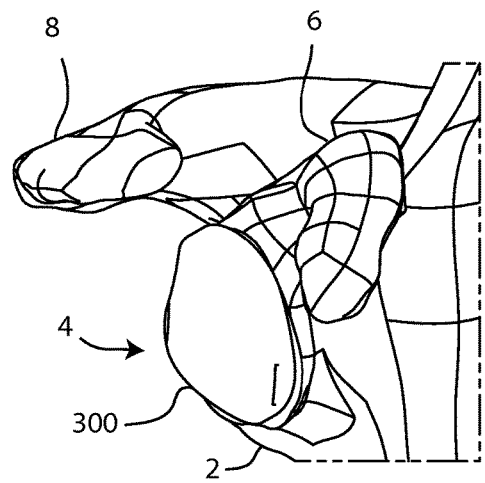
FIG. 15D is an anterior-lateral view of the glenoid component and scapula of FIG. 15A.
Figure 15E:
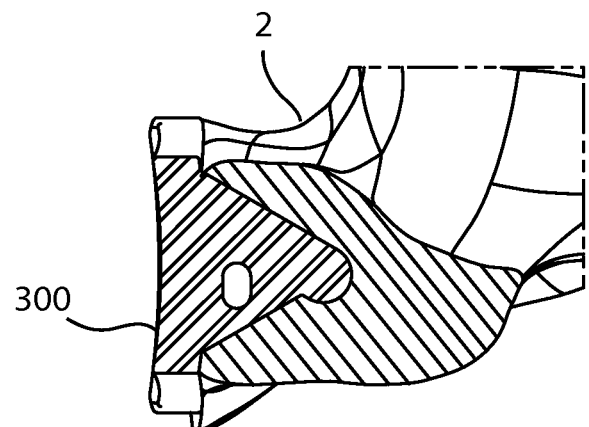
FIG. 15E is a cross sectional view of the glenoid component and scapula of FIG. 15A, taken along section line 15E-15E of FIG. 15B.
Figure 15F:
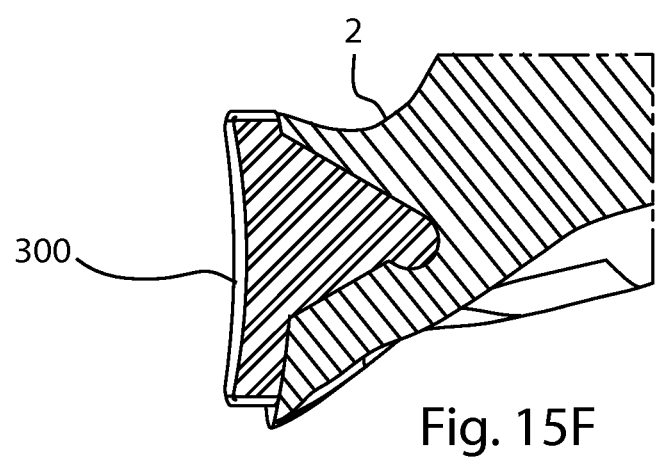
FIG. 15F is a cross sectional view of the glenoid component and scapula of FIG. 15A, taken along section line 15F-15F of FIG. 15B.
Figure 15G:
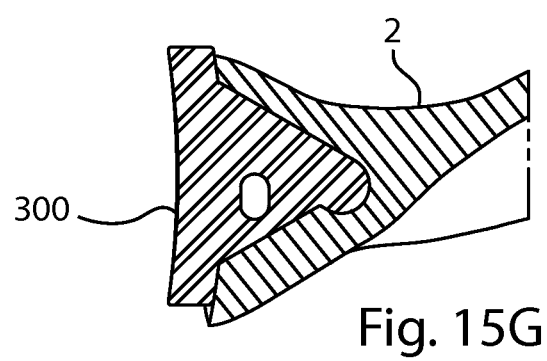
FIG. 15G is a cross sectional view of the glenoid component and scapula of FIG. 15A, taken along section line 15G-15G of FIG. 15B.
Figure 16A:
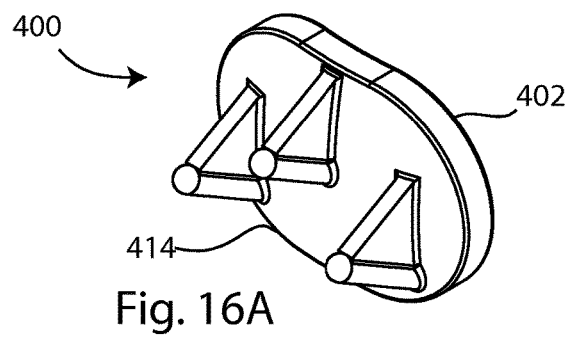
FIG. 16A is a superior-posterior-medial view of yet another glenoid component.
Figure 16B:
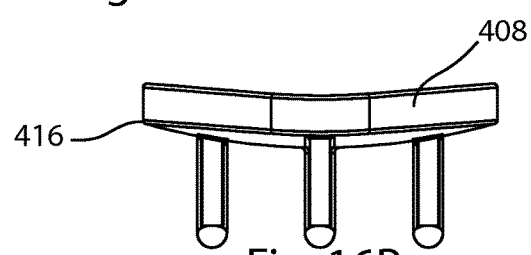
FIG. 16B is a posterior view of the glenoid component of FIG. 16A.
Figures 16C, 16D, 16E:
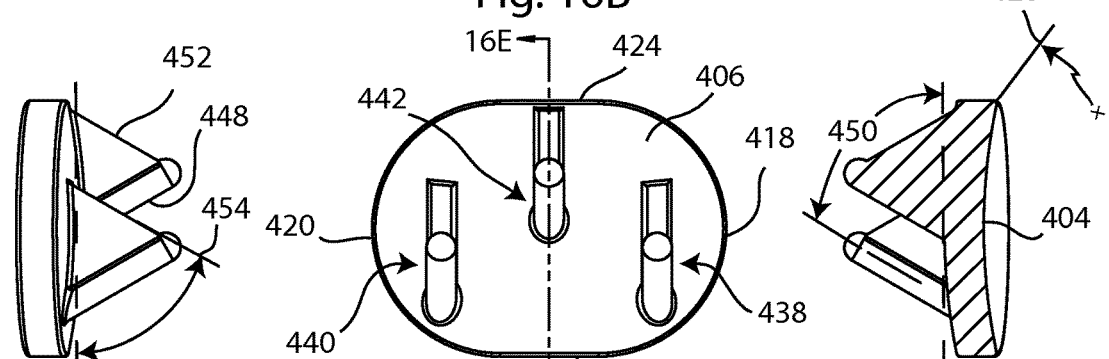
FIG. 16C is an inferior view of the glenoid component of FIG. 16A.
FIG. 16D is a medial view of the glenoid component of FIG. 16A.
FIG. 16E is a cross sectional view of the glenoid component of FIG. 16A, taken along section line 16E-16E of FIG. 16D.
Figure 16F:
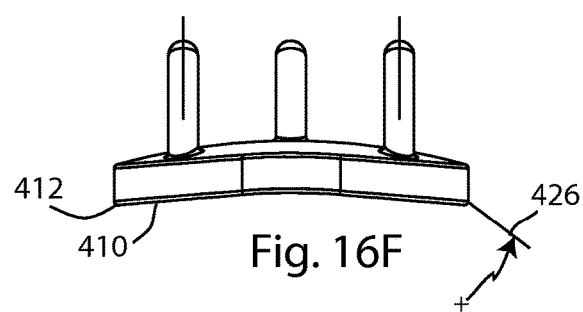
FIG. 16F is an anterior view of the glenoid component of FIG. 16A.
Figure 18A:
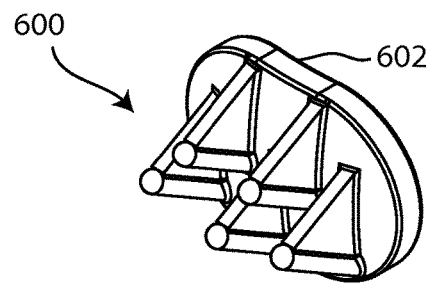
FIG. 18A is a superior-posterior-medial view of yet another glenoid component.
Figure 18B:
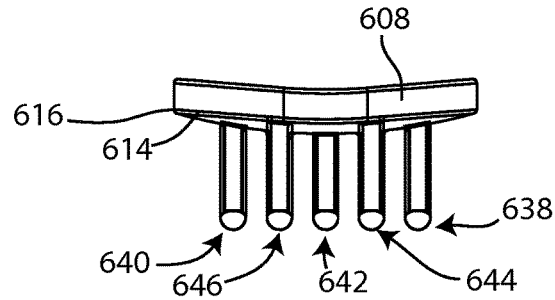
FIG. 18B is a posterior view of the glenoid component of FIG. 18A.
Figures 18C, 18D:
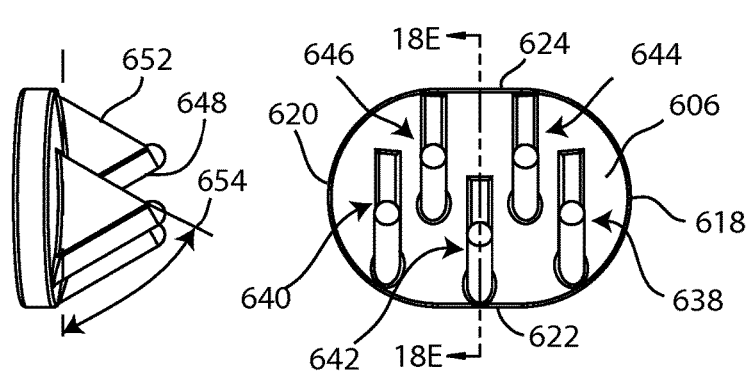
FIG. 18C is an inferior view of the glenoid component of FIG. 18A.
FIG. 18D is a medial view of the glenoid component of FIG. 18A.
Figure 18E:
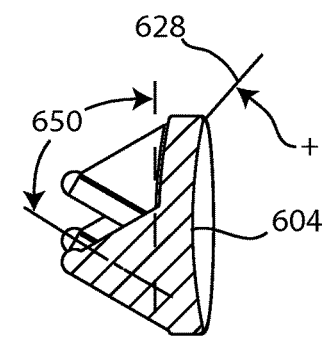
FIG. 18E is a cross sectional view of the glenoid component of FIG. 18A, taken along section line 18E-18E of FIG. 18D.
Figure 18F:
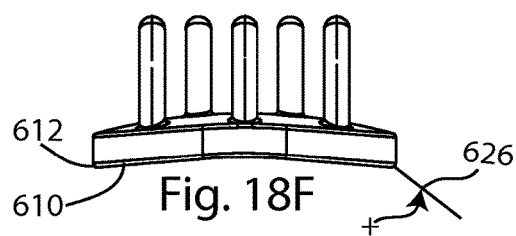
FIG. 18F is an anterior view of the glenoid component of FIG. 18A.
Figure 19A:
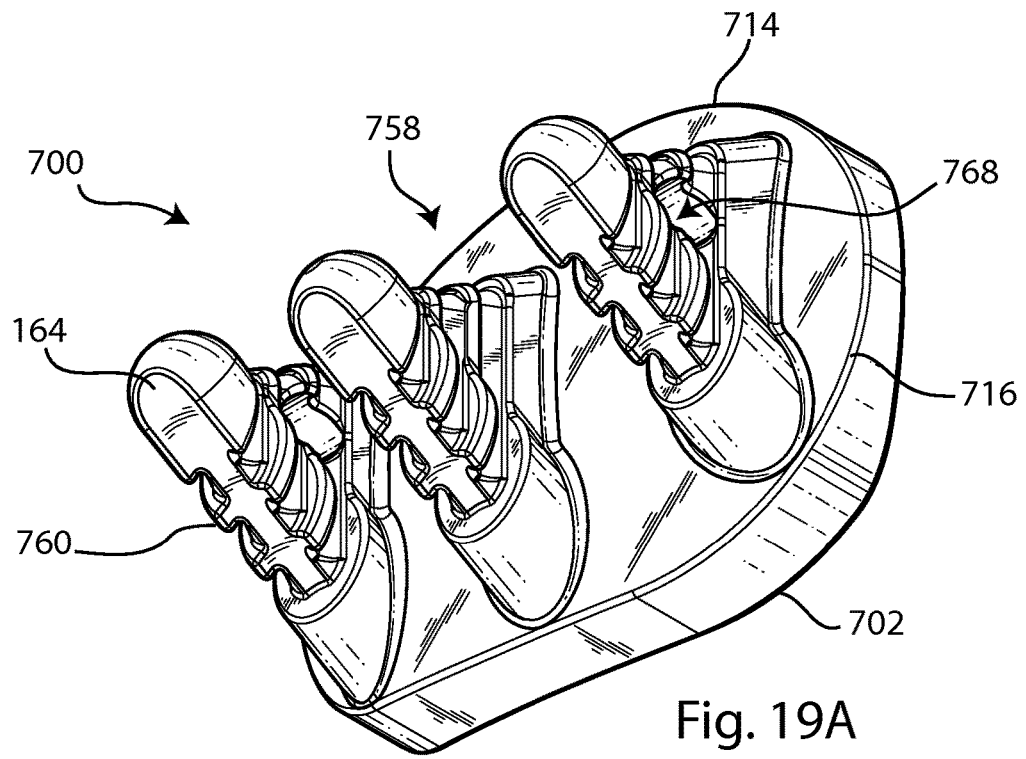
FIG. 19A is an inferior-anterior-medial view of yet another glenoid component.
Figure 19B:
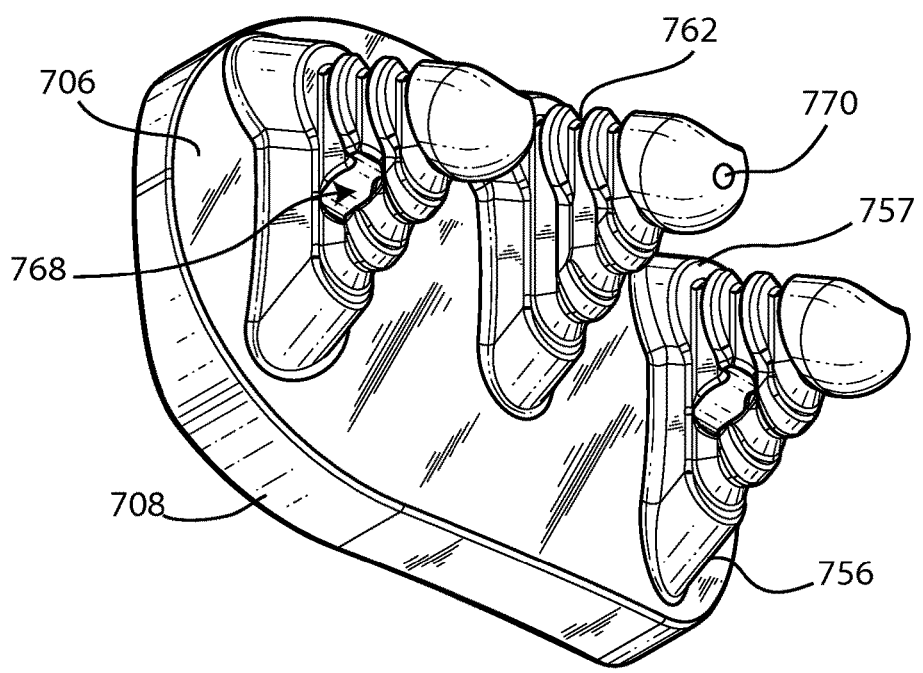
FIG. 19B is an inferior-posterior-medial view of the glenoid component of FIG. 19A.
Figure 19C:
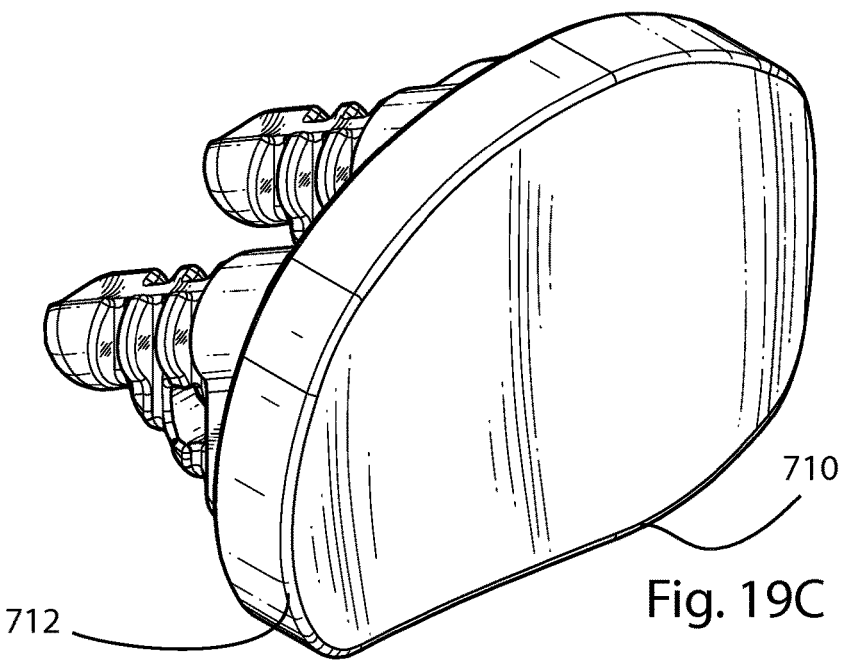
FIG. 19C is a superior-anterior-lateral view of the glenoid component of FIG. 19A.
Figure 19D:
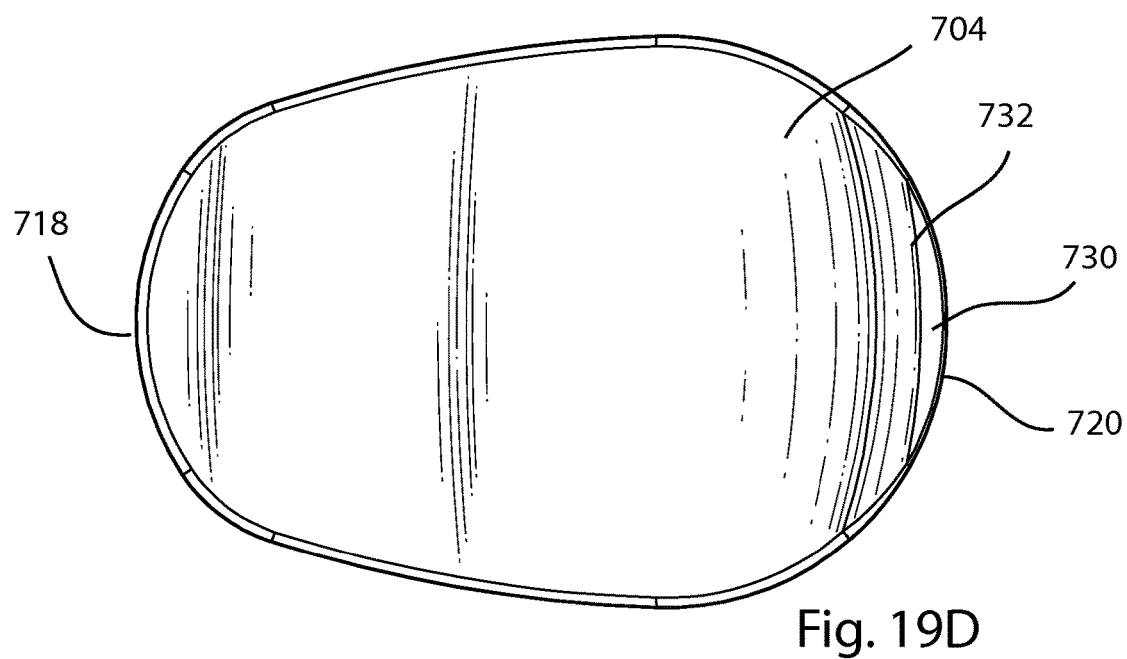
FIG. 19D is a lateral view of the glenoid component of FIG. 19A.
Figure 19E:
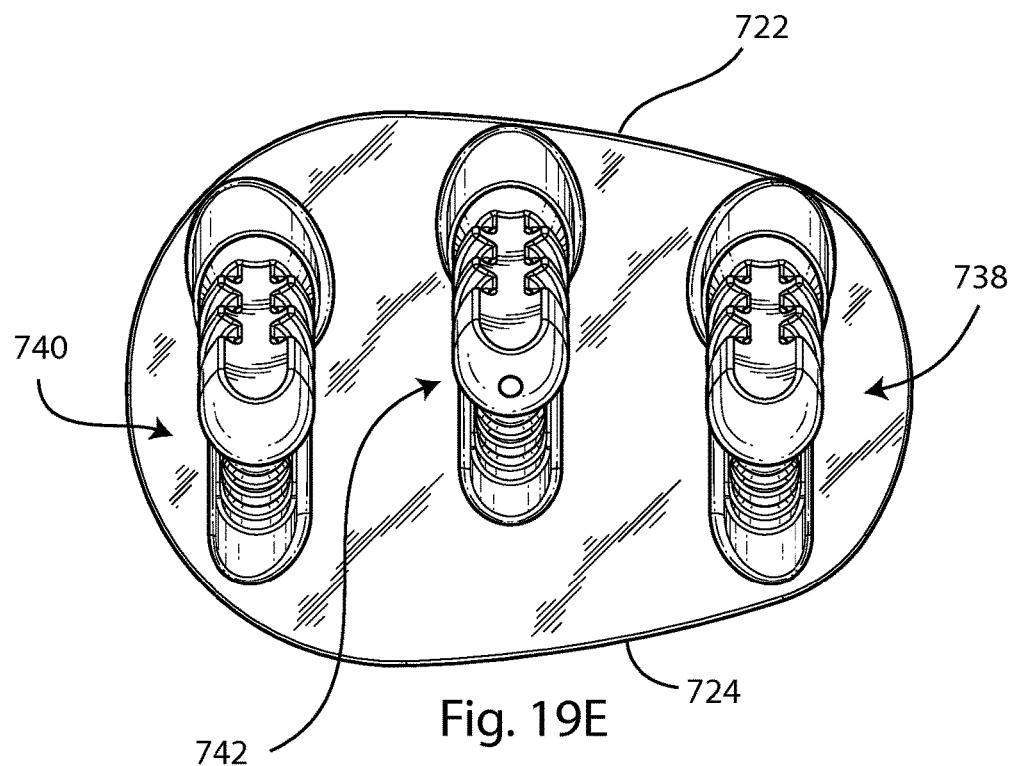
FIG. 19E is a medial view of the glenoid component of FIG. 19A.
Figure 19F:
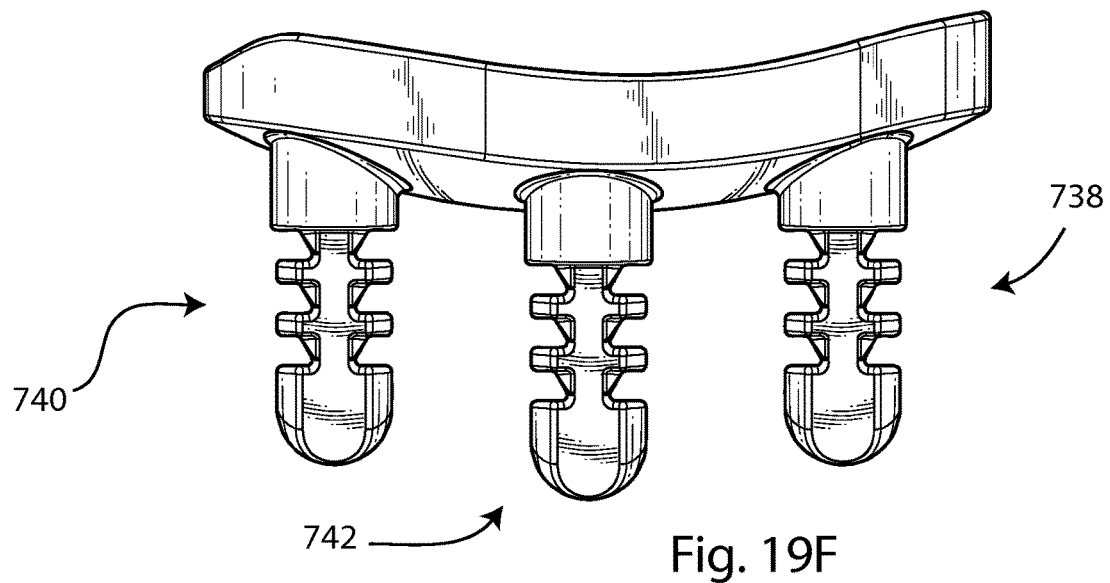
FIG. 19F is an anterior view of the glenoid component of FIG. 19A.

Referring to FIGS. 10A-10G, the glenoid component 200 is shown operatively implanted in a scapula 2. Referring to FIG. 10B, the anchoring elements 238, 240, 242 protrude from the medial bone-facing surface 206 at a slight acute angle in the coronal plane.

Referring to FIGS. 11A-14F, a glenoid component 300 includes a body 302 with a lateral articular surface 304 and an opposite medial bone-facing surface 306. Glenoid component 300 includes the following features, which may be substantially similar to, or the same as, the corresponding features of glenoid component 100: peripheral wall 308, lateral peripheral edge 310, lateral peripheral relief 312, medial peripheral edge 314, medial peripheral relief 316, superior portion 318, inferior portion 320, anterior portion 322, posterior portion 324, S-I radius of curvature 326, A-P radius of curvature 328, inferior chamfer 330, anterior relief 334, posterior relief 336, superior anchoring element 338, inferior anchoring element 340, middle anchoring element 342, dowel or mast 348, mast angle 350, triangular reinforcement plate or sail 352, supplementary angle 354, fixation feature 358, ridge 360, groove 362, and fenestration 368. Glenoid component 300 also includes a flat surface 366 extending along the reinforcement plate side of the triangular shape instead of a slot, channel, or groove comparable to slot 164. Glenoid component 300 lacks a well-defined pedestal, although a face 357 is present at the base of the dowel 348.

Referring to FIGS. 15A-15G, the glenoid component 300 is shown operatively implanted in a scapula 2.

Referring to FIGS. 16A-16F, a glenoid component 400 includes a body 402 with a lateral articular surface 404 and an opposite medial bone-facing surface 406. Glenoid component 400 includes the following features, which may be substantially similar to, or the same as, the corresponding features of glenoid component 100: peripheral wall 408, lateral peripheral edge 410, lateral peripheral relief 412, medial peripheral edge 414, medial peripheral relief 416, superior portion 418, inferior portion 420, anterior portion 422, posterior portion 424, S-I radius of curvature 426, A-P radius of curvature 428, superior anchoring element 438, inferior anchoring element 440, middle anchoring element 442, dowel or mast 448, mast angle 450, triangular reinforcement plate or sail 452, and supplementary angle 454. The middle anchoring element 442 is offset posteriorly so that its dowel 448 projects from a more medial or central location than do the dowels of anchoring elements 438, 440, 138, 140, 142, 238, 240, 242, 338, 340, 342. Dowel 448 of anchoring element 442 also terminates in a more laterally located free end. However, the reinforcement plate 452 remains located in the acute mast angle 450. Glenoid component 400 lacks an inferior chamfer, anterior relief, posterior relief, pedestal, face, fixation feature, ridge, groove, slot, flat surface, or fenestration.

Referring to FIGS. 17A-17F, a glenoid component 500 includes a body 502 with a lateral articular surface 504 and an opposite medial bone-facing surface 506. Glenoid component 500 includes the following features, which may be substantially similar to, or the same as, the corresponding features of glenoid component 100: peripheral wall 508, lateral peripheral edge 510, medial peripheral edge 514, superior portion 518, inferior portion 520, anterior portion 522, posterior portion 524, S-I radius of curvature 526, A-P radius of curvature 528, superior anchoring element 538, inferior anchoring element 540, dowel or mast 548, mast angle 550, triangular reinforcement plate or sail 552, supplementary angle 554. Glenoid component 500 lacks a lateral peripheral relief, medial peripheral relief, inferior chamfer, anterior relief, posterior relief, middle anchoring element, pedestal, face, fixation feature, ridge, groove, slot, flat surface, or fenestration.

Referring to FIGS. 18A-18F, a glenoid component 600 includes a body 602 with a lateral articular surface 604 and an opposite medial bone-facing surface 606. Glenoid component 600 includes the following features, which may be substantially similar to, or the same as, the corresponding features of glenoid component 100: peripheral wall 608, lateral peripheral edge 610, lateral peripheral relief 612, medial peripheral edge 614, medial peripheral relief 616, superior portion 618, inferior portion 620, anterior portion 622, posterior portion 624, S-I radius of curvature 626, A-P radius of curvature 628, superior anchoring element 638, inferior anchoring element 640, middle anchoring element 642, dowel or mast 648, mast angle 650, triangular reinforcement plate or sail 652, and supplementary angle 654. Glenoid component 600 also includes a mid-superior anchoring element 644 between anchoring elements 638, 642 and a mid-inferior anchoring element 646 between anchoring elements 640, 642. The anchoring elements 644, 646 are offset posteriorly so that their dowels 448 project from medial or central locations as described above for anchoring element 442 of glenoid component 400. Glenoid component 600 lacks an inferior chamfer, anterior relief, posterior relief, pedestal, face, fixation feature, ridge, groove, slot, flat surface, or fenestration.

Referring to FIGS. 19A-19L, a glenoid component 700 includes a body 702 with a lateral articular surface 704 and an opposite medial bone-facing surface 706. Glenoid component 700 includes the following features, which may be substantially similar to, or the same as, the corresponding features of glenoid component 100: peripheral wall 708, lateral peripheral edge 710, lateral peripheral relief 712, medial peripheral edge 714, medial peripheral relief 716, superior portion 718, inferior portion 720, anterior portion 722, posterior portion 724, S-I radius of curvature 726, A-P radius of curvature 728, inferior chamfer 730, superior anchoring element 738, inferior anchoring element 740, middle anchoring element 742, dowel or mast 748, mast angle 750, triangular reinforcement plate or sail 752, supplementary angle 754, pedestal 756, face 757, fixation features 758, ridge 760, groove 762, slot 764, flat surface 766, and fenestration 768. Glenoid component 700 also includes a chamfer blend radius 732 and a hole 770. The chamfer blend radius 732 is adjacent to the inferior chamfer 730. The chamfer blend radius 732 is more centrally located than is the inferior chamfer 730. The hole 770 extends lengthwise into the dowel 748 of middle anchoring element 742, and may receive a radiographic marker (not shown). Glenoid component 700 lacks an anterior relief or a posterior relief.

Referring now to FIGS. 20A-28C, instruments for use with the disclosed glenoid prostheses will now be described.

Figure 20A:
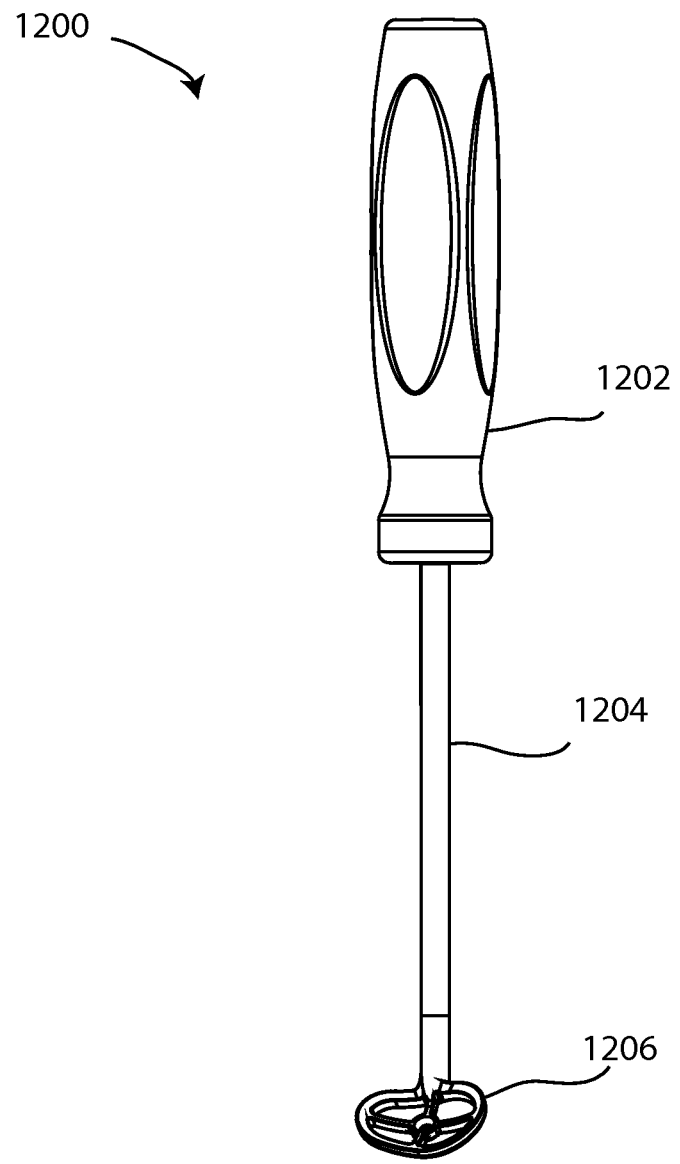
FIG. 20A is an isometric view of a size template.
Figure 20B:
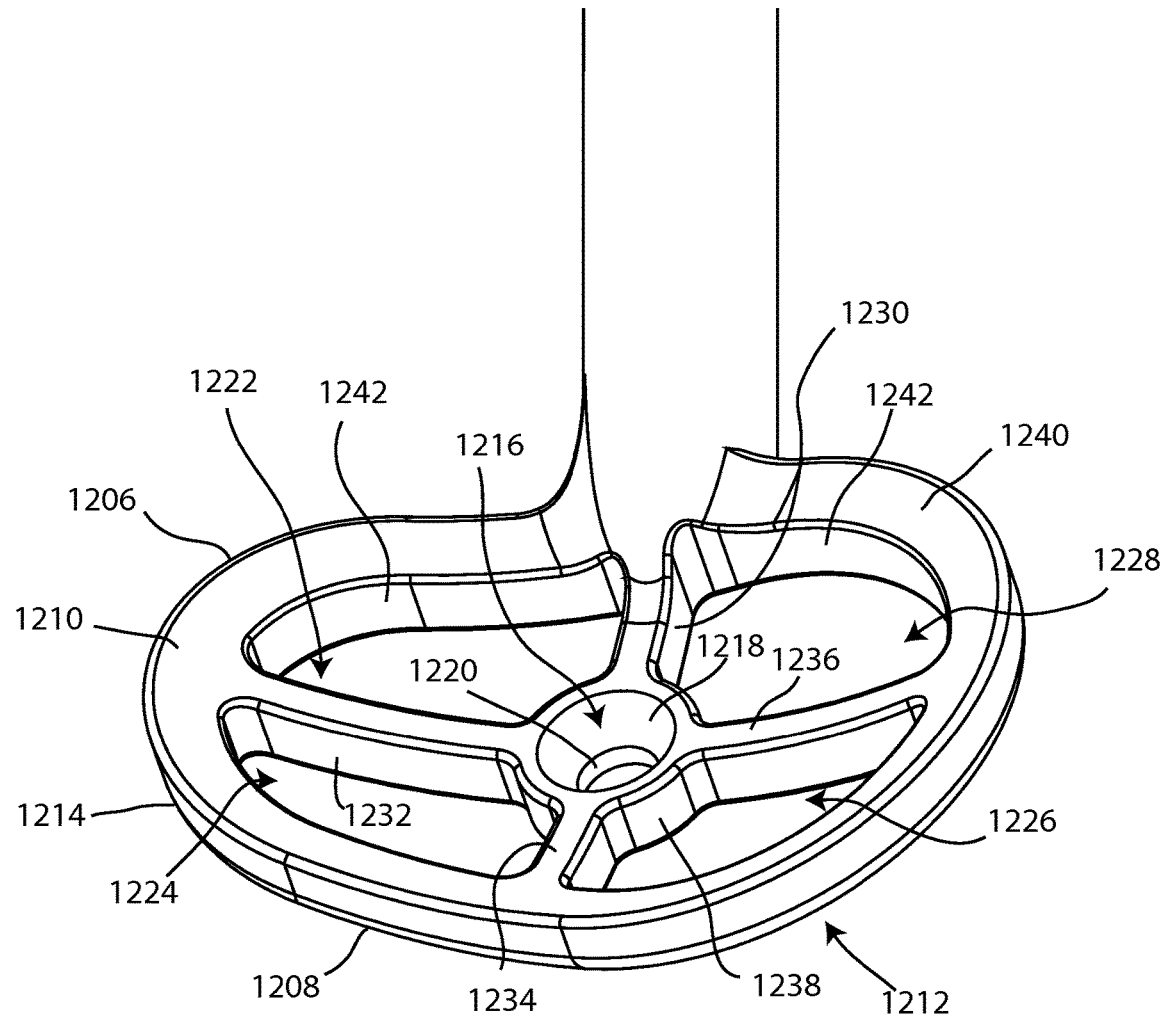
FIG. 20B is a detail view of a working portion of the size template of FIG. 20A.

Referring to FIGS. 20A-20B, a size template 1200 includes a handle 1202, a shaft 1204, and a working portion 1206. The handle 1202 and the working portion 1206 are arranged at opposite ends of the shaft 1204, which is straight in this example. The working portion 1206 includes a body 1208 with a first surface 1210 and an opposite bone-facing surface 1212. The bone-facing surface 1212 may match the bone-facing surface 106, 206, 306, 406, 506, 706 of one of the glenoid components. The body 1208 is oriented at an obtuse angle relative to the shaft 1204. The obtuse angle is greater than ninety degrees and less than one hundred eighty degrees. A peripheral wall 1214 extends around the body 1208 between the surfaces 1210, 1212. The body 1208 includes a central hole 1216. The central hole 1216 includes a conical portion 1218 that extends through the first surface 1210, and a cylindrical portion 1220 that extends through the bone-facing surface. The body 1208 may include one or more apertures; the example shown includes four apertures 1222, 1224, 1226, 1228 which may let the user see portions of a bone surface against which the body 1208 rests. The central hole 1216 in the illustrated example is supported in the midst of the apertures 1222, 1224, 1226, 1228 by at least one rib; four ribs 1230, 1232, 1234, 1236 are shown. The central hole 1216 is encircled by a ring 1238 in this example. The body 1208 may be described as forming a loop 1240 bounded externally by the peripheral wall 1214 and internally by an inner wall 1242, which is intersected by the at least one rib.

Figure 21A:
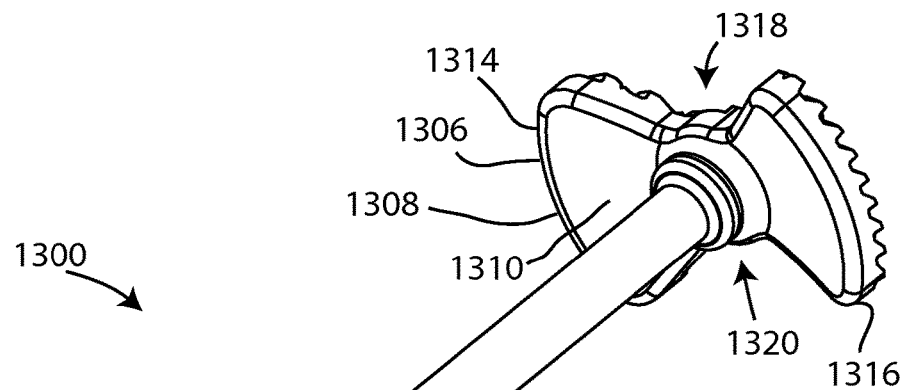
FIG. 21A is an isometric view of a reamer.
Figure 21B:
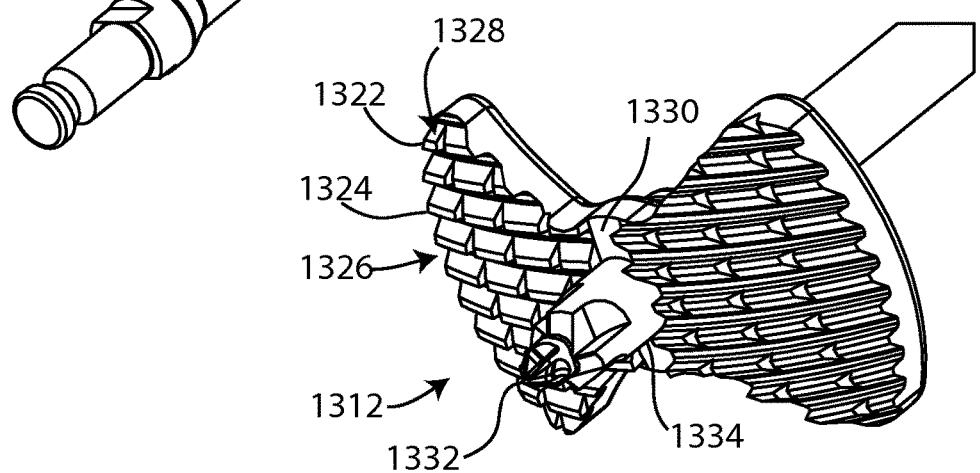
FIG. 21B is another isometric view of the reamer of FIG. 21A from a different direction.
Figure 22A:
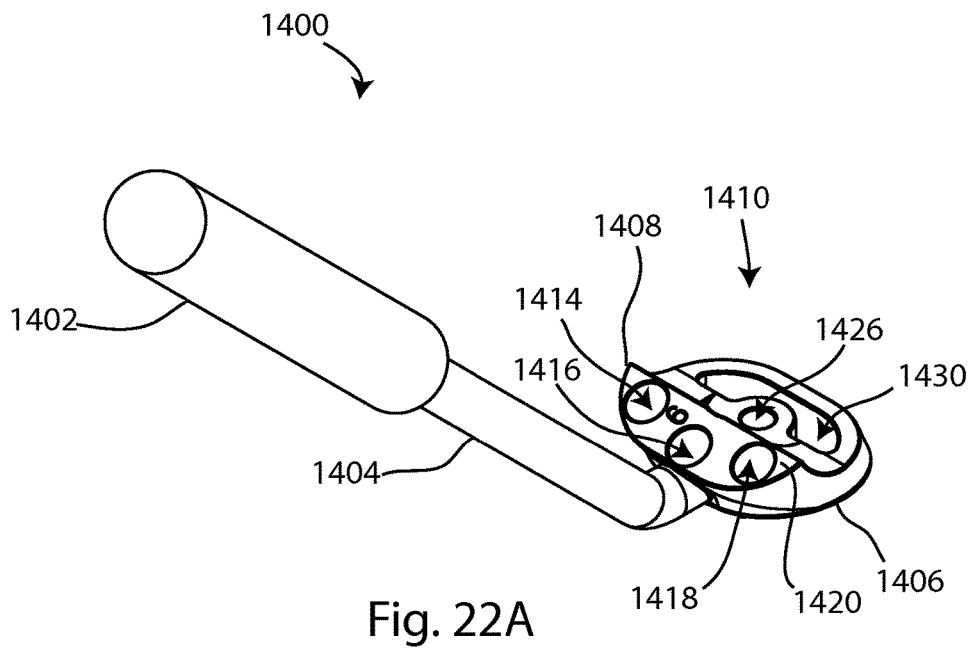
FIG. 22A is an isometric view of a drill guide.
Figure 22B:
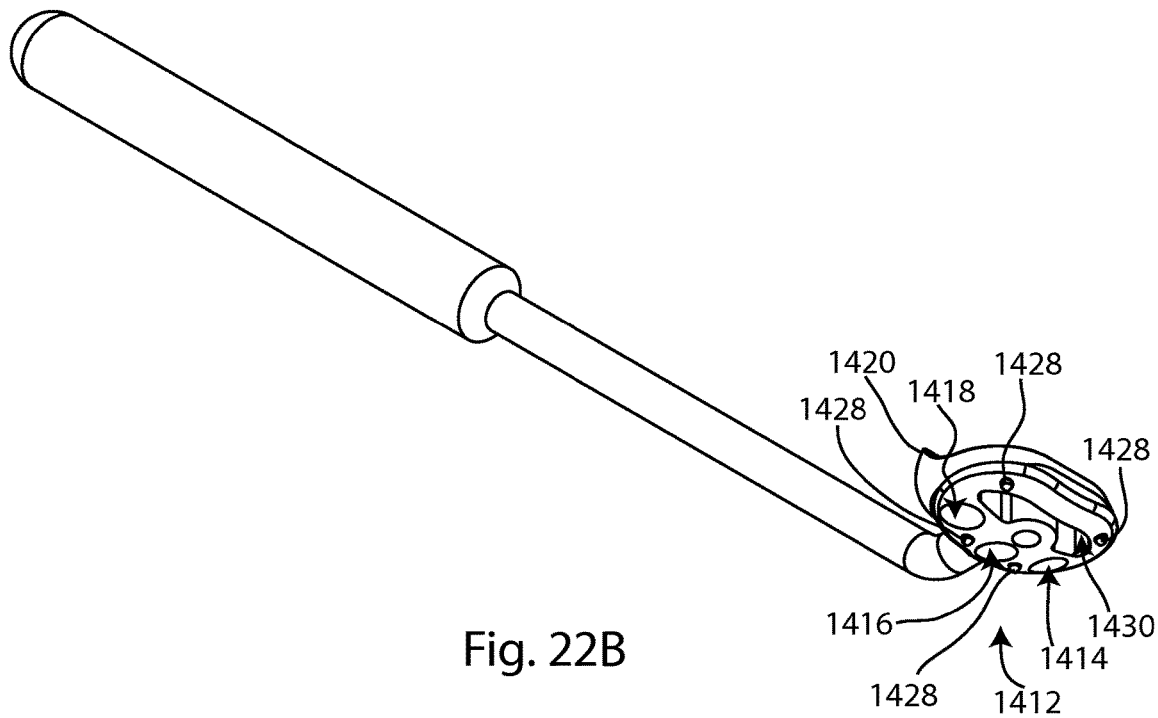
FIG. 22B is another isometric view of the drill guide of FIG. 22A from a different direction.
Figure 22C:
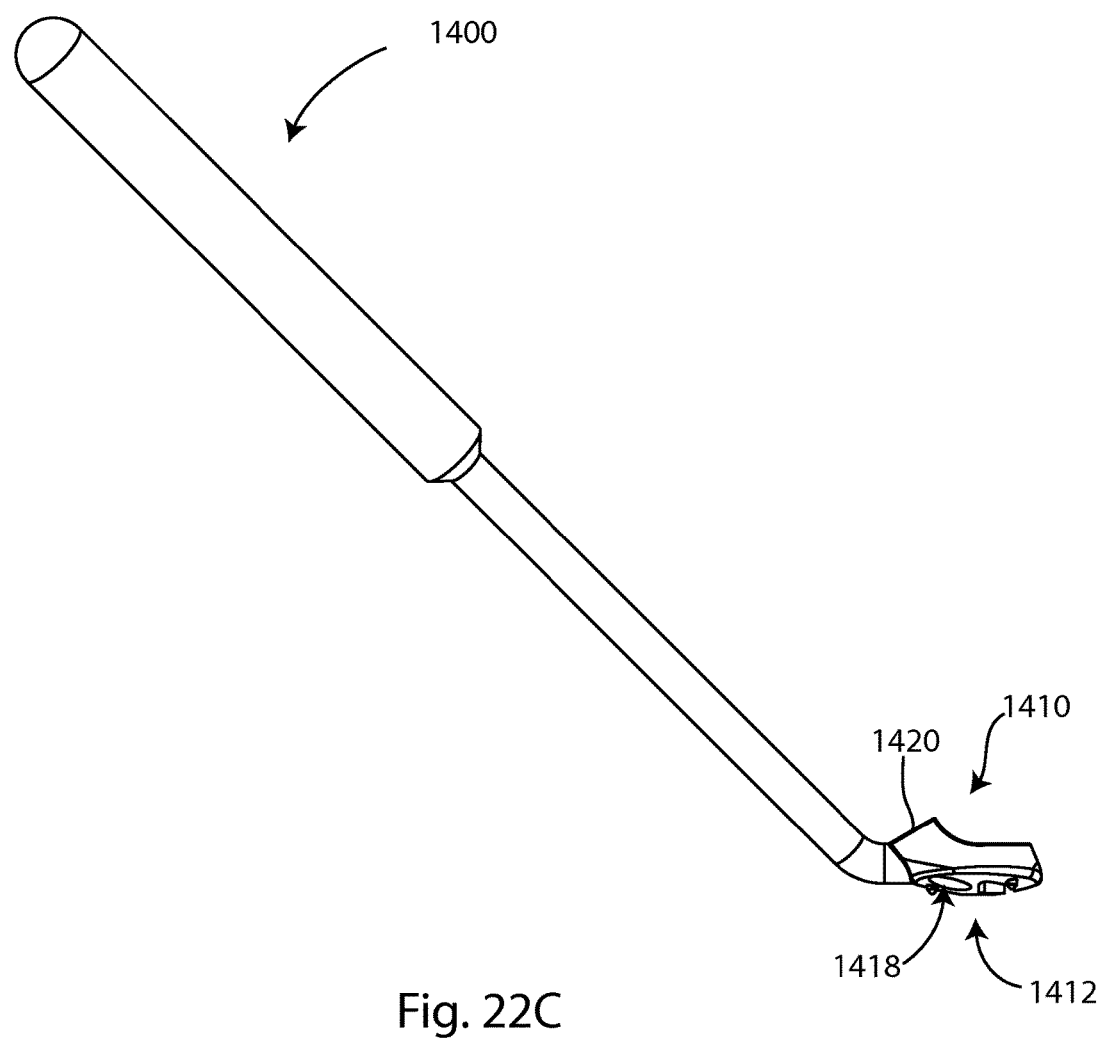
FIG. 22C is a side view of the drill guide of FIG. 22A.

Referring to FIGS. 21A-21B, a reamer 1300 includes a coupling 1302, a shaft 1304, and a working portion 1306. The coupling 1302 and the working portion 1306 are arranged at opposite ends of the shaft 1304, which is straight in this example. The coupling 1302 connects the reamer 1300 to a torque source, such as a power handpiece or a T-handle, so that the reamer 1300 may be rotated or spun about a central longitudinal axis of the shaft 1304 by the torque source. The working portion 1306 includes a body 1308 with a first surface 1310 and an opposite bone-facing surface 1312. The bone-facing surface 1312 may match the bone-facing surface 106, 206, 306, 406, 506, 706 of one of the glenoid components. The body 1308 may be described as bi-lobular, the two lobes 1314, 1316 established by opposing indentations 1318, 1320. In other examples, the body 1308 may be round or nearly round. The bone-facing surface 1312 includes bone removal features 1322, which may be teeth, serrations, ridges and grooves, knurling, a sandpaper texture, or the like. In the example shown, the bone removal features 1322 are alternating ridges 1324 and grooves 1326. The cutting edges of the ridges 1324 are interrupted or scored by cross grooves 1328. The bone removal features 1322 on lobe 1314 are oriented opposite to the bone removal features 1322 on lobe 1316 so that the bone removal features 1322 on each lobe 1314, 1316 are oriented to efficiently remove bone as the reamer 1300 spins in one direction. A trough 1330 separates the bone removal features 1322 on lobe 1314 from the bone removal features 1322 on lobe 1316. A drill tip 1332 protrudes from the bone-facing surface 1312. The drill tip 1332 may be end-cutting, side-cutting, or both; an end-cutting example is shown. A second, larger diameter, drill feature 1334 may protrude from the bone-facing surface 1312 around the base of the drill tip 1332. The drill feature 1334 may be end-cutting, side-cutting, or both; an end-cutting example is shown.

The recipient site on the scapula can be prepared quickly using a matched-design cutting jig with adjacent slots for drill bits and/or burrs or oscillating saw blades, all of which are instruments commonly used by orthopedic surgeons. The matched-design recipient hole preparation jig includes a handle to be held by the operating surgeon. The handle is attached to a drill guide that has openings that match the number and location of the anchoring elements that are present on the chosen glenoid prosthetic component. When the drill guide is placed flush against the glenoid bony surface, the angle of the drill guide opening matches the dowel angle 150, 250, 350, 450, 550, 650, 750.

Referring to FIGS. 22A-22J, a drill guide 1400 includes a handle 1402, a shaft 1404, and a working portion 1406. The handle 1402 and the working portion 1406 are arranged at opposite ends of the shaft 1404, which is straight in this example. The working portion 1406 includes a body 1408 with a first surface 1410 and an opposite bone-facing surface

1412. The bone-facing surface 1412 may match the bone-facing surface 106, 206, 306, 406, 506, 706 of one of the glenoid components. The body 1408 is oriented at an obtuse angle relative to the shaft 1404. The obtuse angle is greater than ninety degrees and less than one hundred eighty degrees. The body 1408 includes at least one hole whose size, location, and angle relative to the bone-facing surface 1412 correspond to the size, location, and angle of the dowel of one of the previously described anchoring elements. While the present example is shown with three holes 1414, 1416, 1418 corresponding to a three-anchor glenoid component, other examples may have a different number or arrangement of holes corresponding to another glenoid component. The body 1408 may include a protrusion 1420 extending from the first surface 1410 around the holes 1414, 1416, 1418 to increase the length of the holes. A central hole 1426 extends through the body 1408 normal to the bone-facing surface 1412. One or more spikes 1428 may protrude from the bone-facing surface 1412. One or more apertures 1430 may extend through the body 1408 to provide a visualization window for the user. The body 1408 may resemble one of the previously-described glenoid components, as illustrated in FIGS. 22A-22J. Alternatively, the body 1408 may include only enough material to form or surround the surfaces, hole(s), and/or protrusion described above.

Figure 23A:
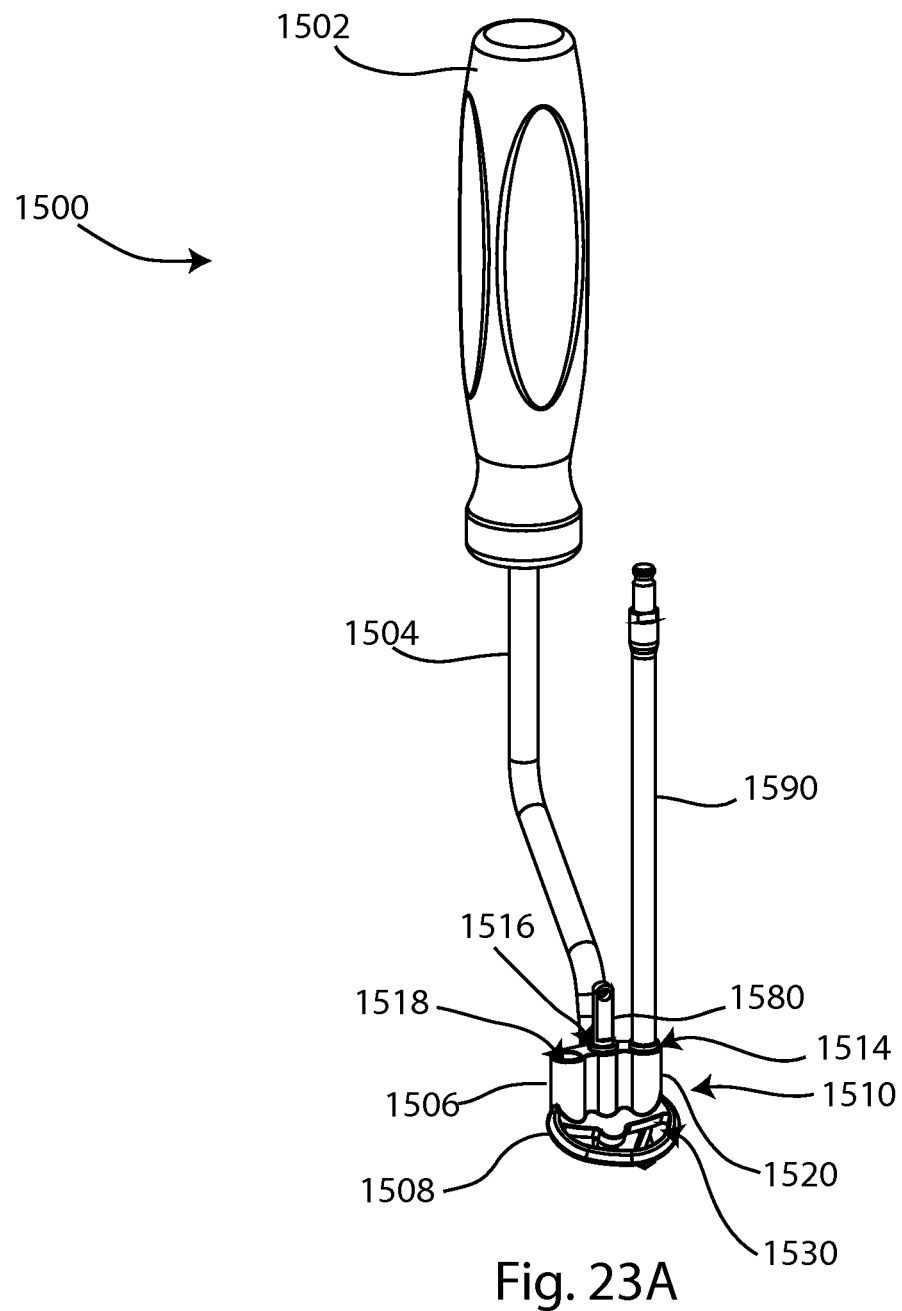
FIG. 23A is an isometric view of another drill guide with a drill and a keel position tamp.
Figure 23B:
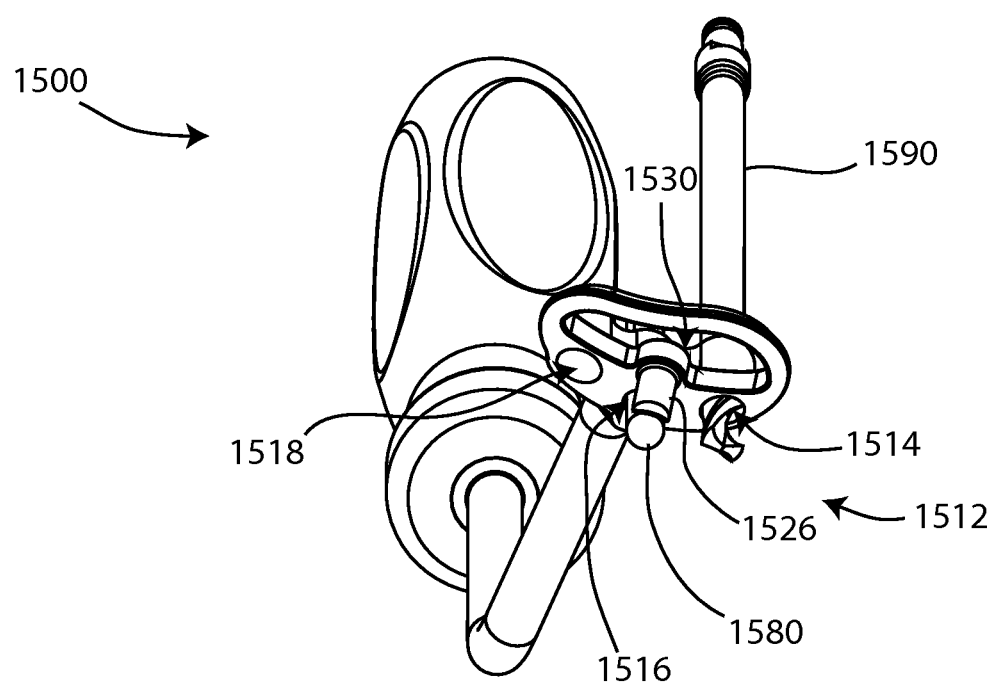
FIG. 23B is another isometric view of the drill guide, drill, and keel position tamp of FIG. 23A from a different direction.
Figure 24A:
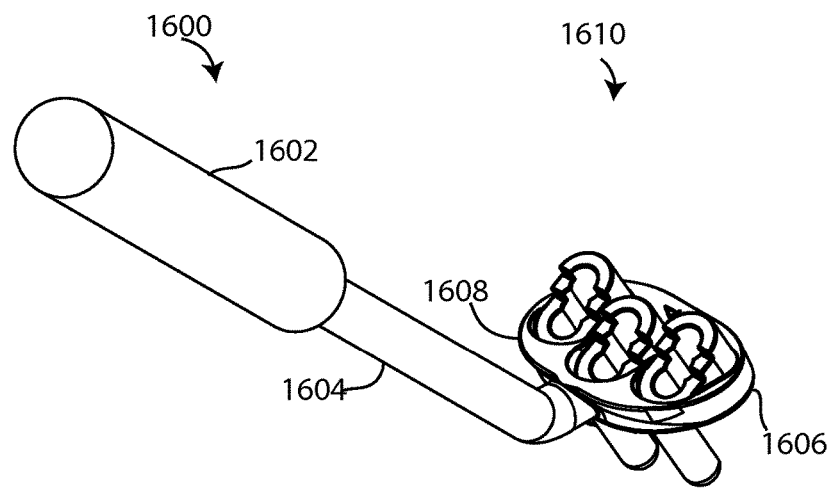
FIG. 24A is an isometric view of yet another drill guide.
Figure 24B:
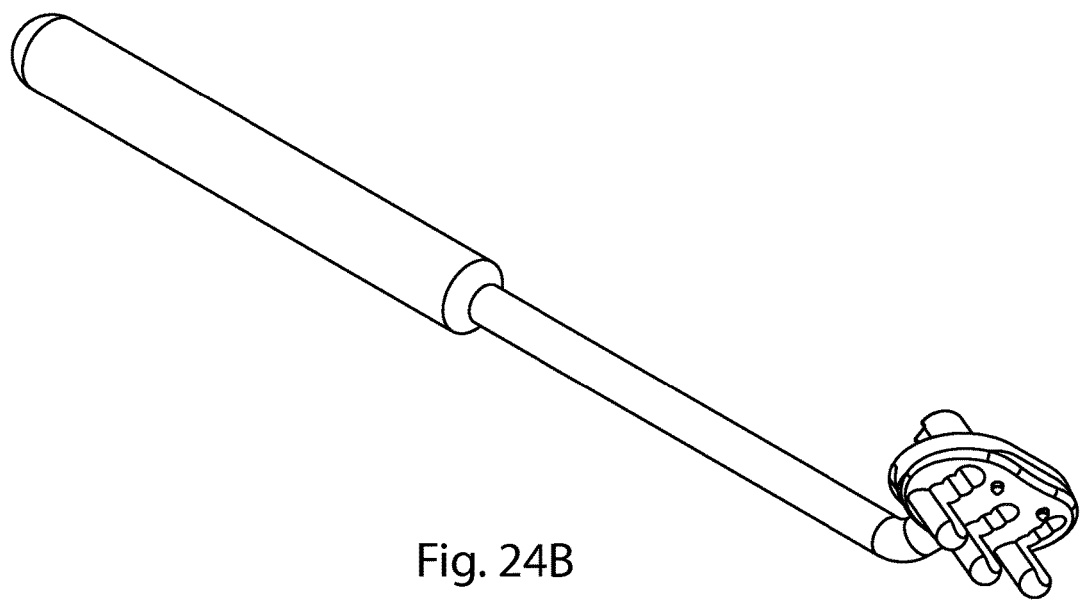
FIG. 24B is another isometric view of the drill guide of FIG. 24A from a different direction.
Figure 24C:
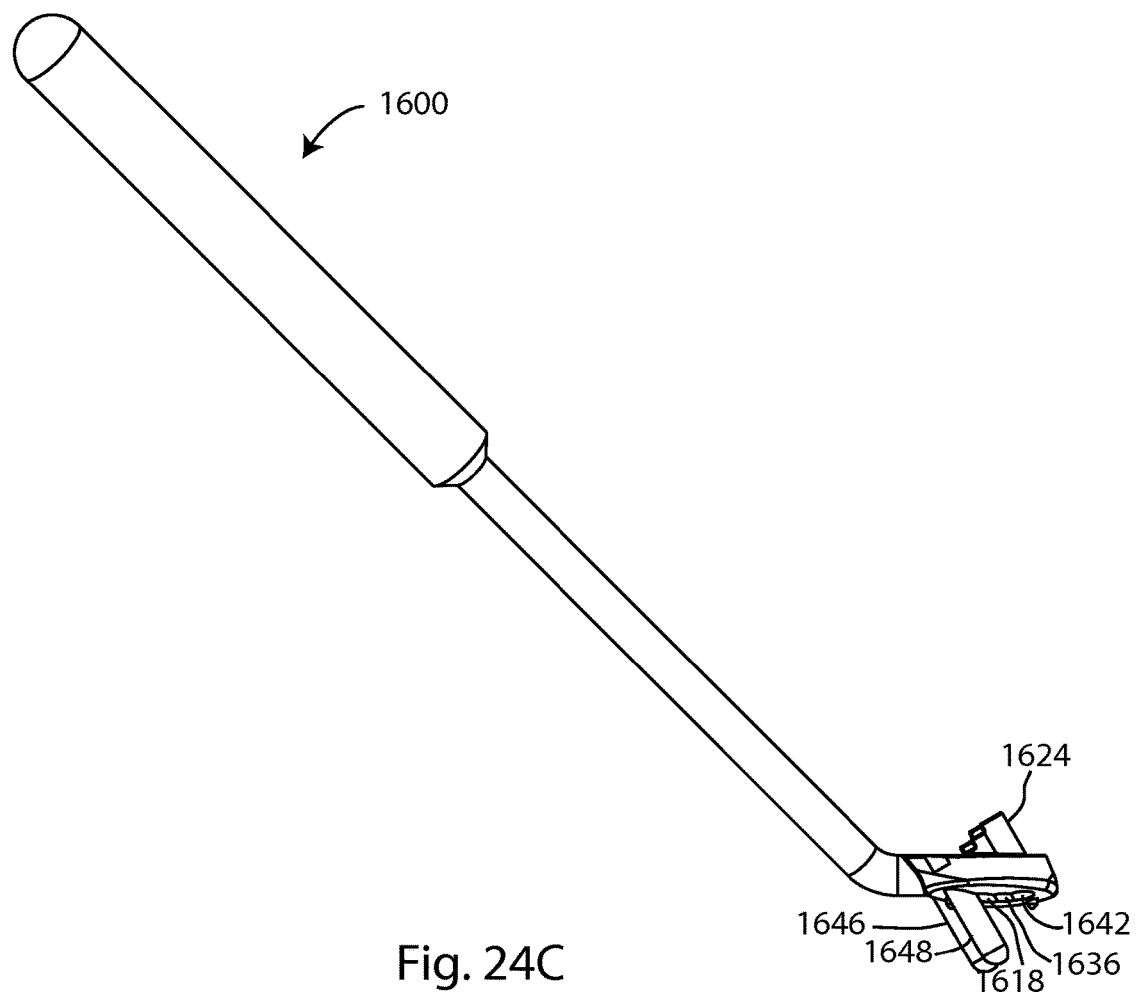
FIG. 24C is a side view of the drill guide of FIG. 24A.
Figure 24K:
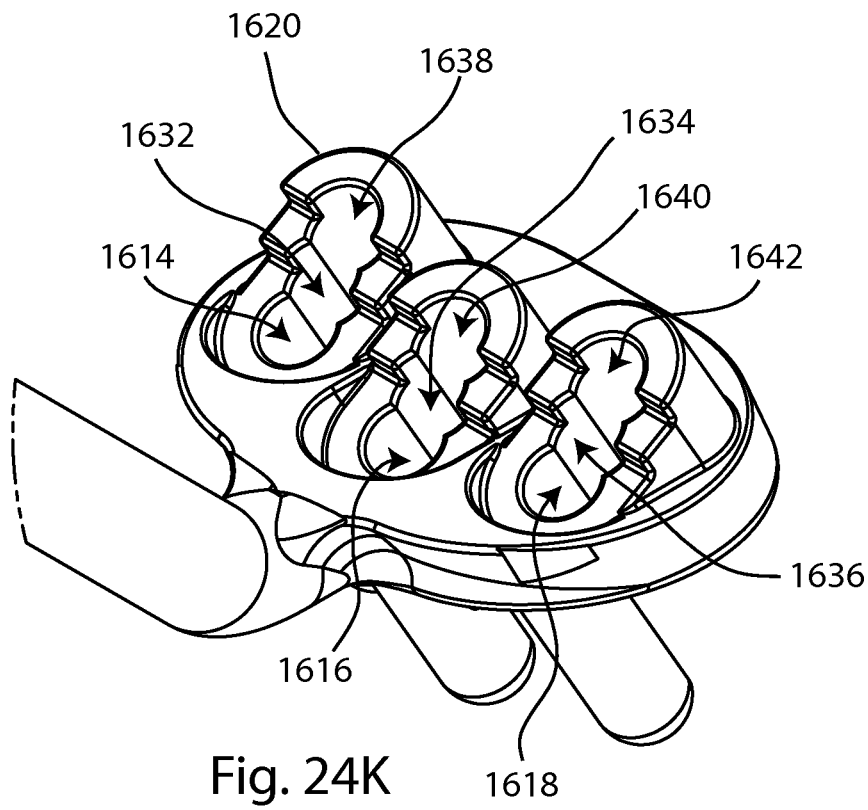
FIG. 24K is an enlarged detail view of a portion of the drill guide of FIG. 24A.
Figure 24L:
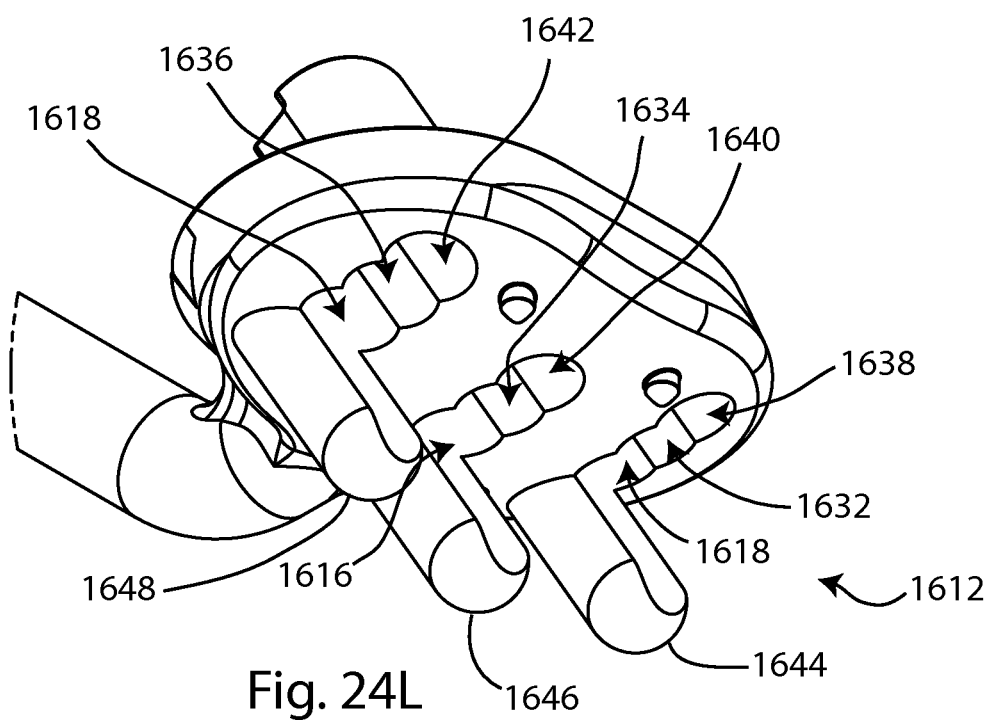
FIG. 24L is an enlarged detail view of a portion of the drill guide of FIG. 24A.

Referring to FIGS. 23A-23B, another drill guide 1500 includes a handle 1502, a shaft 1504, and a working portion 1506. The shaft 1504 is bent, or zig-zag, in this example. Drill guide 1500 includes the following features, which may be substantially similar to, or the same as, the corresponding features of drill guide 1400: body 1508, first surface 1510, bone-facing surface 1512, hole 1514, hole 1516, hole 1518, protrusion 1520, aperture 1530. Drill guide 1500 also includes central peg 1526, which projects from the body 1508 normal to the bone-facing surface 1512. Drill guide 1500 lacks a central hole or a spike.

Drill guide 1500 is shown with a drill 1590 in hole 1514 and a keel position tamp 1580 in hole 1516. The drill 1590 and keel position tamp 1580 are interchangeably received in holes 1514, 1516, 1518. The drill 1590 forms a hole sized to receive a dowel. In one example, the drill 1590 may form a 6.0 mm hole. The keel position tamp 1580 may also be referred to as a locator pin or peg.

Referring to FIGS. 24A-24J, yet another drill guide 1600 includes a handle 1602, a shaft 1604, and a working portion 1606. The shaft 1604 is straight in this example. Drill guide 1600 includes the following features, which may be substantially similar to, or the same as, the corresponding features of drill guide 1400: body 1608, first surface 1610, bone-facing surface 1612, hole 1614, hole 1616, hole 1618, protrusion 1620, spike 1628. Drill guide 1600 also includes protrusion 1622, protrusion 1624, holes 1632, 1634, 1636, 1638, 1640, 1642, and pegs 1644, 1646, 1648. Peg 1644 and holes 1614, 1632, 1638 form a line with each hole partially overlapping the adjacent peg or hole(s). In this example, protrusion 1620 extends from the first surface 1610 around the holes 1614, 1632, 1638. Peg 1646 and holes 1616, 1634, 1640 form a line with each hole partially overlapping the adjacent peg or hole(s). Protrusion 1622 extends from the first surface 1610 around the holes 1616, 1634, 1640. Peg 1648 and holes 1618, 1636, 1642 form a line with each hole partially overlapping the adjacent peg or hole(s). Protrusion 1624 extends from the first surface 1610 around the holes 1618, 1636, 1642. Drill guide 1600 lacks a central hole or an aperture. It is contemplated that some examples of guide 1600 may include elongated slots, similar to the apertures 1930, 1932 of the broach 2000 presented below, instead of the illustrated arrangement of partially overlapping holes, Such slots may receive cutting tools such as saw blades, burrs, punches, osteotomes, and/or curettes, as well as drills.

Figure 25A:
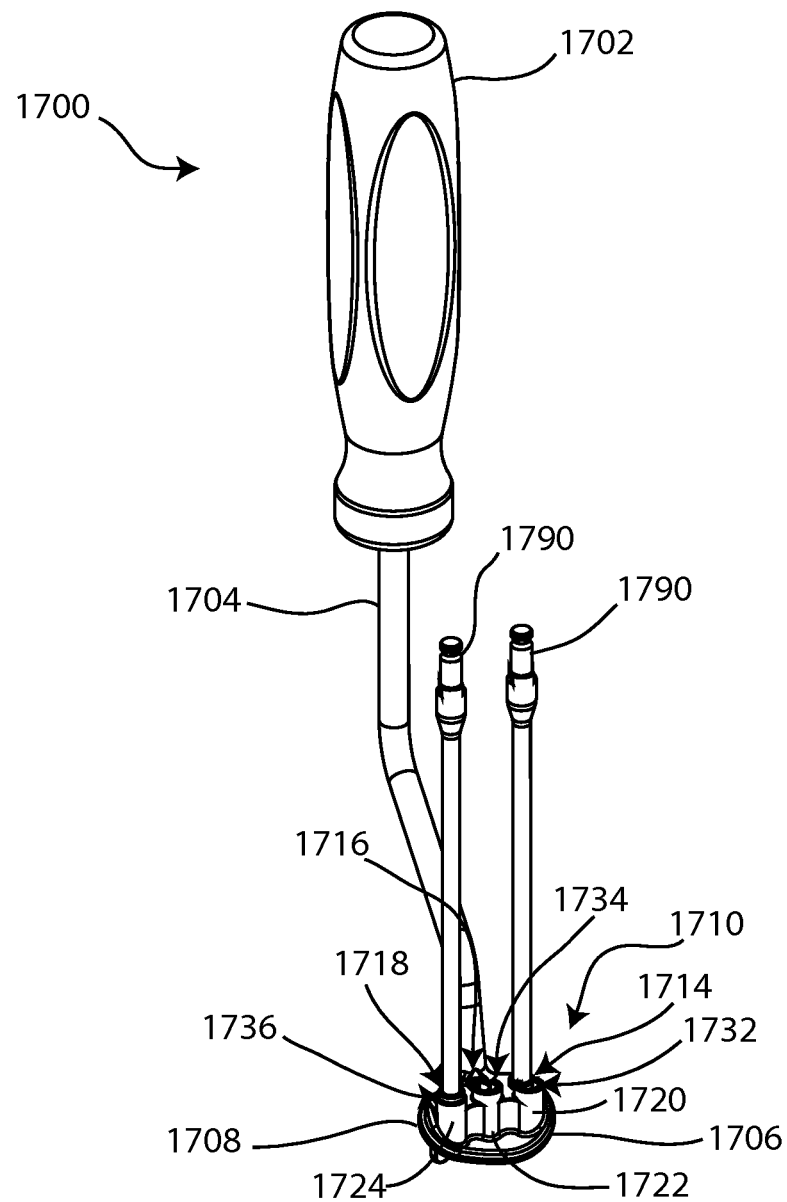
FIG. 25A is an isometric view of yet another drill guide with drills.
Figure 25B:
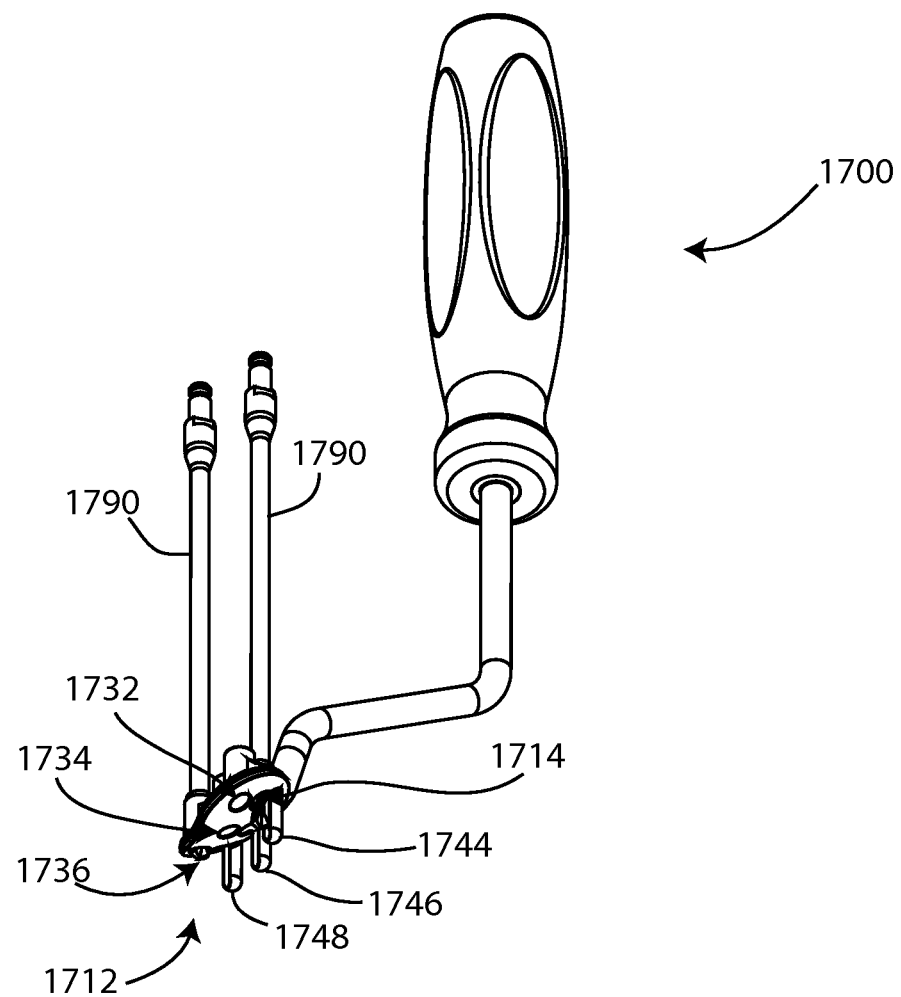
FIG. 25B is another isometric view of the drill guide and drills of FIG. 25A from a different direction.

Referring to FIGS. 25A-25B, yet another drill guide 1700 includes a handle 1702, a shaft 1704, and a working portion 1706. The shaft 1704 is bent, or zig-zag, in this example. Drill guide 1700 includes the following features, which may be substantially similar to, or the same as, the corresponding features of drill guide 1400: body 1708, first surface 1710, bone-facing surface 1712, hole 1714, hole 1716, hole 1718, and protrusion 1720. Drill guide 1700 also includes protrusion 1722, protrusion 1724, holes 1732, 1734, 1736, and pegs 1744, 1746, 1748. Peg 1744 and holes 1714, 1732 form a line with each hole partially overlapping the adjacent peg or hole. In this example, protrusion 1720 extends from the first surface 1710 around the holes 1714, 1732. Peg 1746 and holes 1716, 1734 form a line with each hole partially overlapping the adjacent peg or hole. Protrusion 1722 extends from the first surface 1710 around the holes 1716, 1734. Peg 1748 and holes 1718, 1736 form a line with each hole partially overlapping the adjacent peg or hole. Protrusion 1724 extends from the first surface 1710 around the holes 1718, 1736. Drill guide 1700 lacks a central hole, an aperture, or a spike.

Drill guide 1700 is shown with a drill 1790 in hole 1714 and another drill 1790 in hole 1736. Drill 1790 is interchangeably received in holes 1714, 1716, 1718, 1732, 1734, 1736. The drill 1790 forms a hole sized to receive a portion of a triangular reinforcement plate. In one example, the drill 1790 may form a 4.5 mm hole.

Figure 26A:
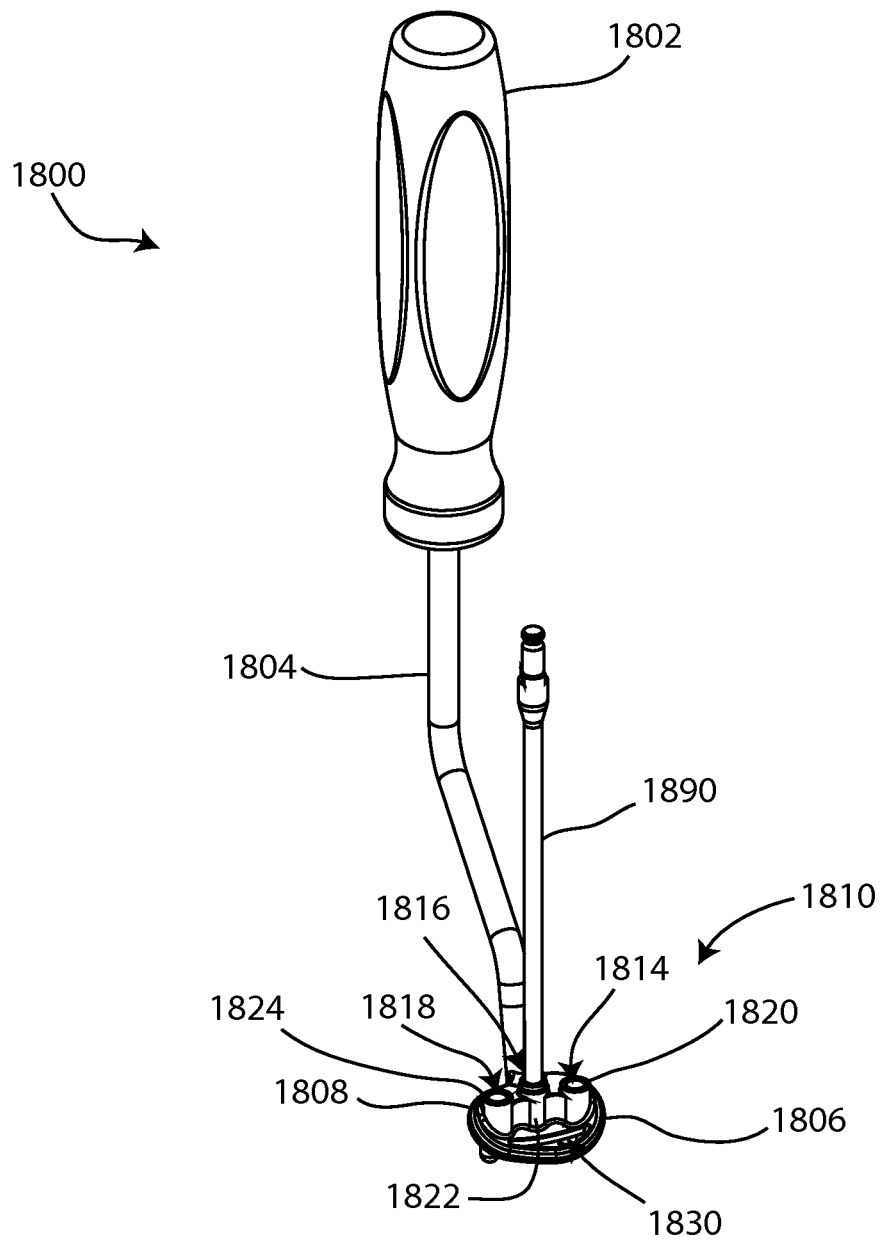
FIG. 26A is an isometric view of yet another drill guide with a drill.
Figure 26B:
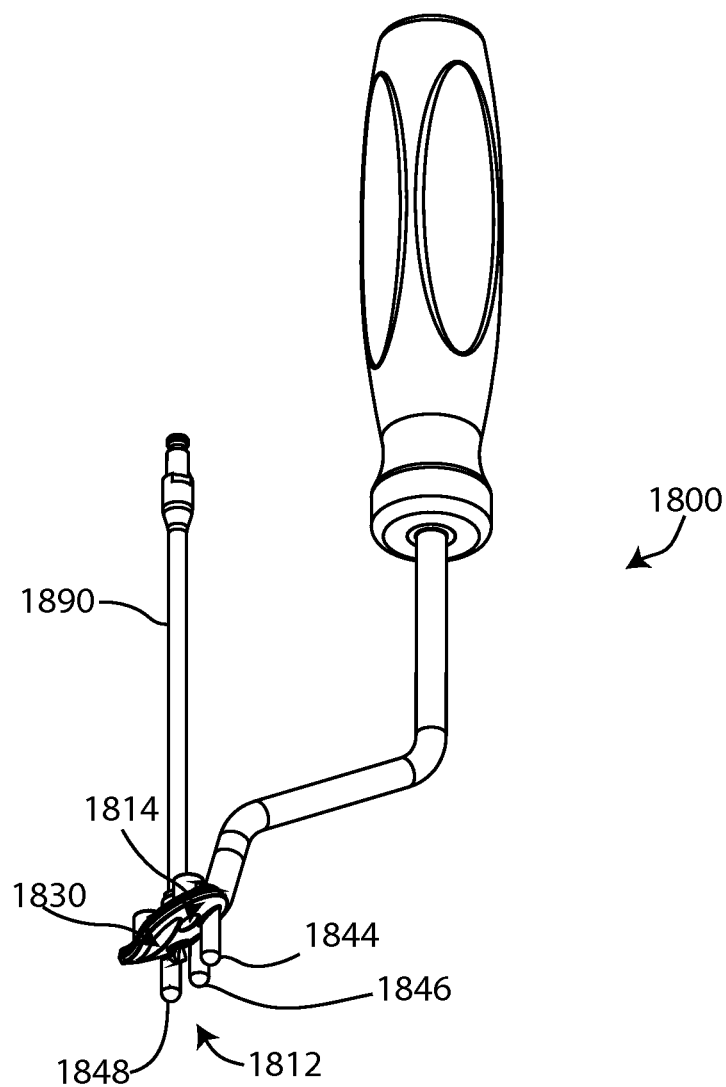
FIG. 26B is another isometric view of the drill guide and drills of FIG. 26A from a different direction.
Figure 27A:
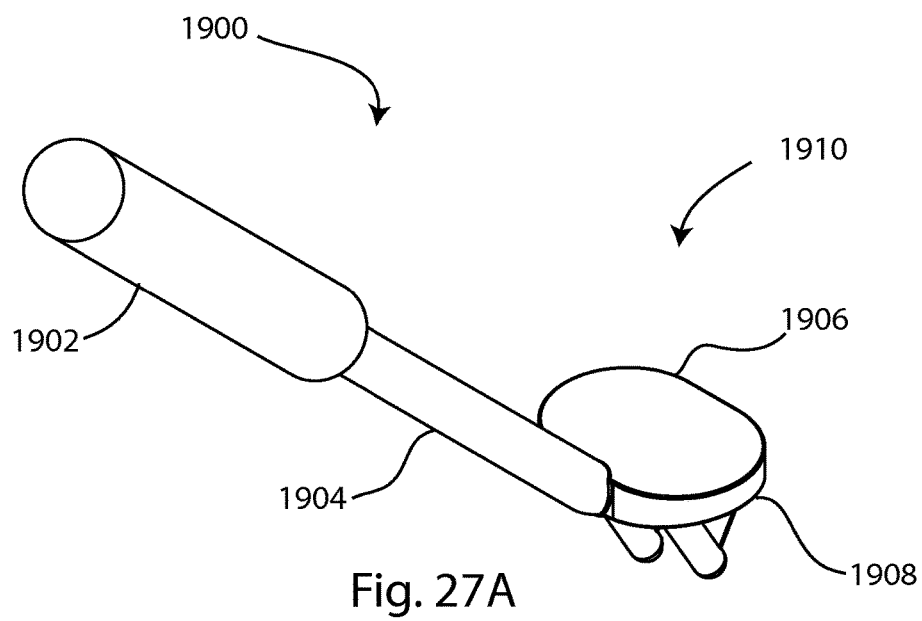
FIG. 27A is an isometric view of a punch.
Figure 27B:
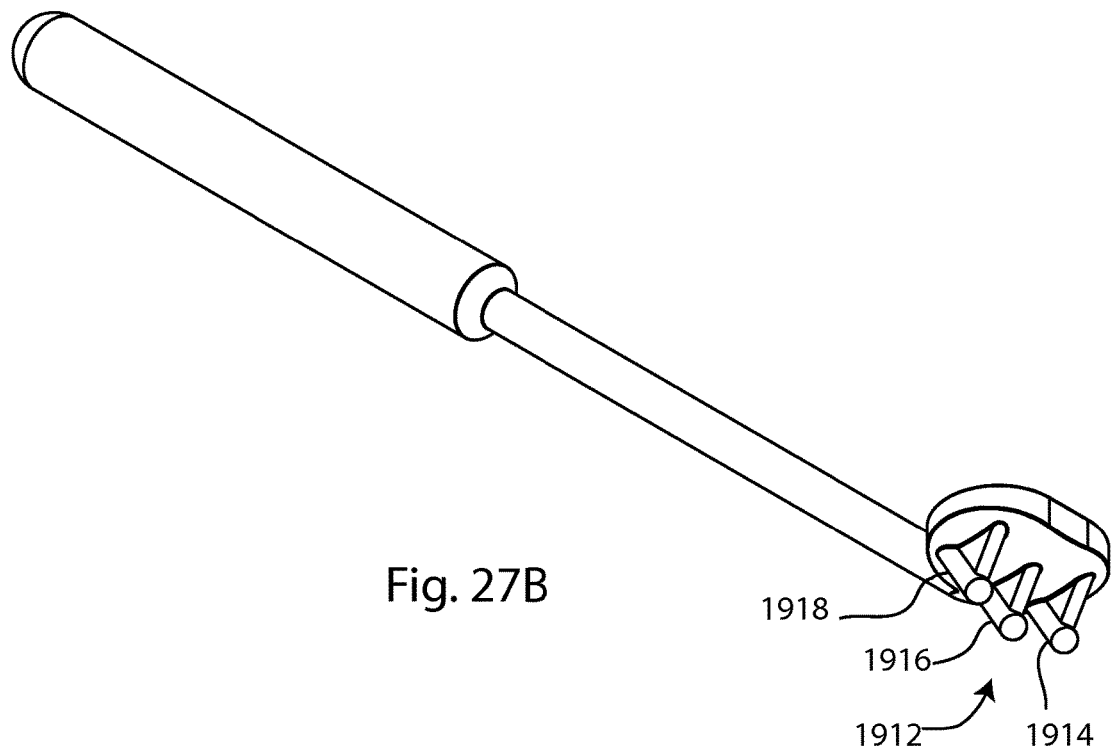
FIG. 27B is another isometric view of the punch of FIG. 27A from a different direction.
Figure 27C:
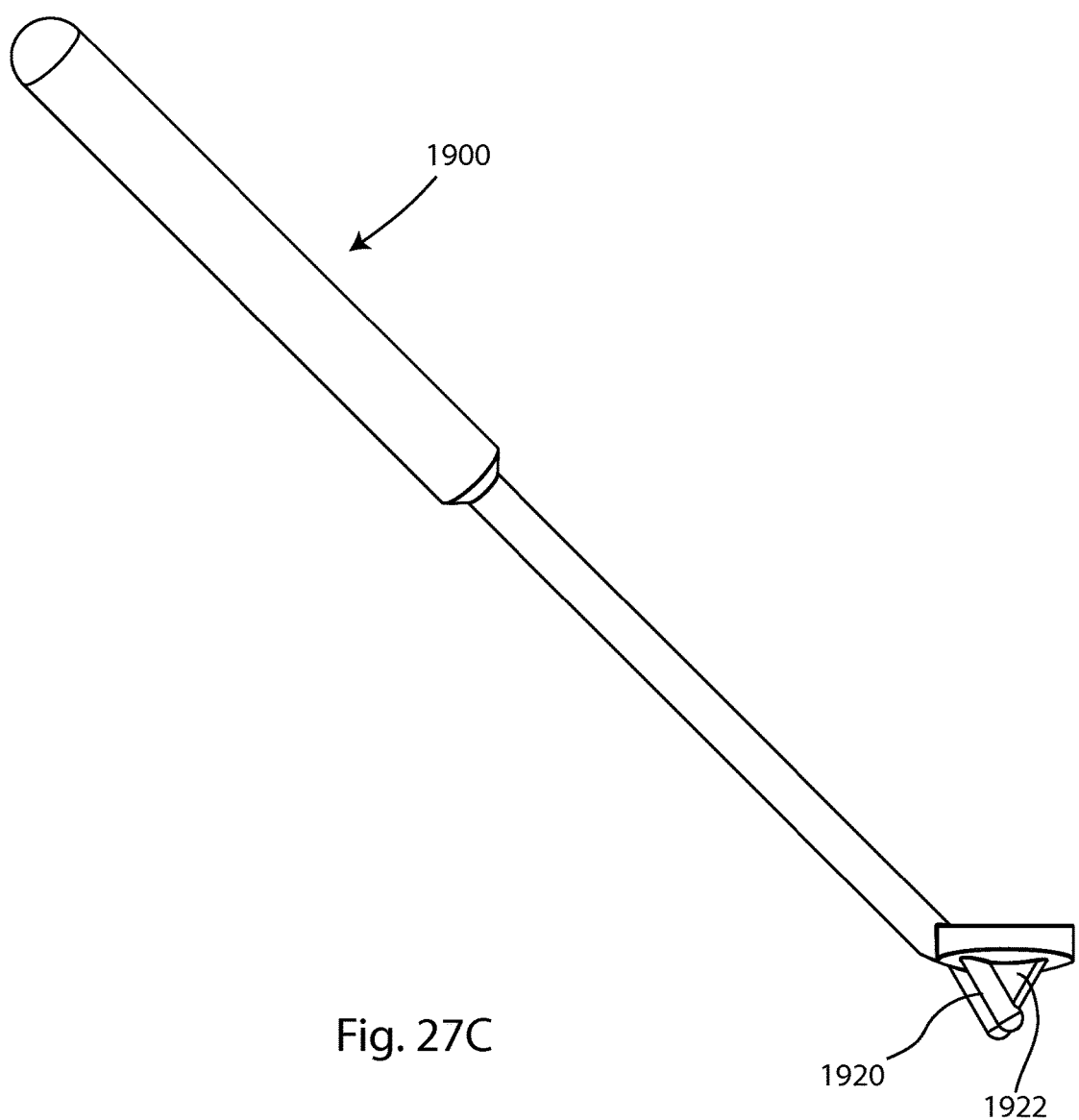
FIG. 27C is a side view of the punch of FIG. 27A.

Referring to FIGS. 26A-26B, yet another drill guide 1800 includes a handle 1802, a shaft 1804, and a working portion 1806. The shaft 1804 is bent, or zig-zag, in this example. Drill guide 1800 includes the following features, which may be substantially similar to, or the same as, the corresponding features of drill guide 1400: body 1808, first surface 1810, bone-facing surface 1812, hole 1814, hole 1816, hole 1818, protrusion 1820, and aperture 1830. Drill guide 1800 also includes protrusion 1822, protrusion 1824, and pegs 1844, 1846, 1848. Peg 1844 and hole 1814 are adjacent. In this example, protrusion 1820 extends from the first surface 1810 around the hole 1814. Peg 1846 and hole 1816 are adjacent. Protrusion 1822 extends from the first surface 1810 around the hole 1816. Peg 1848 and hole 1818 are adjacent. Protrusion 1824 extends from the first surface 1810 around the hole 1818. Drill guide 1800 lacks a central hole or a spike.

Drill guide 1800 is shown with a drill 1890 in hole 1816. The drill 1890 is interchangeably received in holes 1814, 1816, 1818. The drill 1890 forms a hole sized to receive a portion of a triangular reinforcement plate, and may be identical to drill 1790. In one example, the drill 1890 may form a 4.5 mm hole.

In addition to the matched-design cutting jig described above, the dowel opening may be further prepared and expanded with punches or broaches. This preparation step may be useful when the dowel shape is other than circular, such as a dovetail design, although a punch or broach may also be used when the dowel shape is circular.

Referring to FIGS. 27A-27I, a punch 1900 includes a handle 1902, a shaft 1904, and a working portion 1906. The handle 1902 and the working portion 1906 are arranged at opposite ends of the shaft 1904, which is straight in this example. The working portion 1906 includes a body 1908 with a first surface 1910 and an opposite bone-facing surface 1912. The bone-facing surface 1912 may match the bone-facing surface 106, 206, 306, 406, 506, 706 of one of the glenoid components. The body 1908 is oriented at an obtuse angle relative to the shaft 1904. The obtuse angle is greater than ninety degrees and less than one hundred eighty degrees. The working portion 1906 includes at least one anchoring element 1914 which protrudes outwardly from the bone-facing surface. The example shown includes anchoring elements 1914, 1916, 1918. Each anchoring element includes a dowel 1920 and a triangular reinforcement plate 1922, as described above for the glenoid components. The body 1908 may resemble one of the previously-described glenoid components, as illustrated in FIGS. 27A-27I. Alternatively, the body 1908 may include only enough material to form or surround the surfaces, hole(s), and/or protrusion described above.

One example of the punch 1900 may be used as a cement tamp or pressurizer to push bone cement into bony interstices. Another example of the punch 1900 may include bone removal features 1924, which may be teeth, serrations, ridges and grooves, knurling, a sandpaper texture, or the like, so that the punch 1900 may be used to form a complementary socket to receive a glenoid component.

Figure 28A:
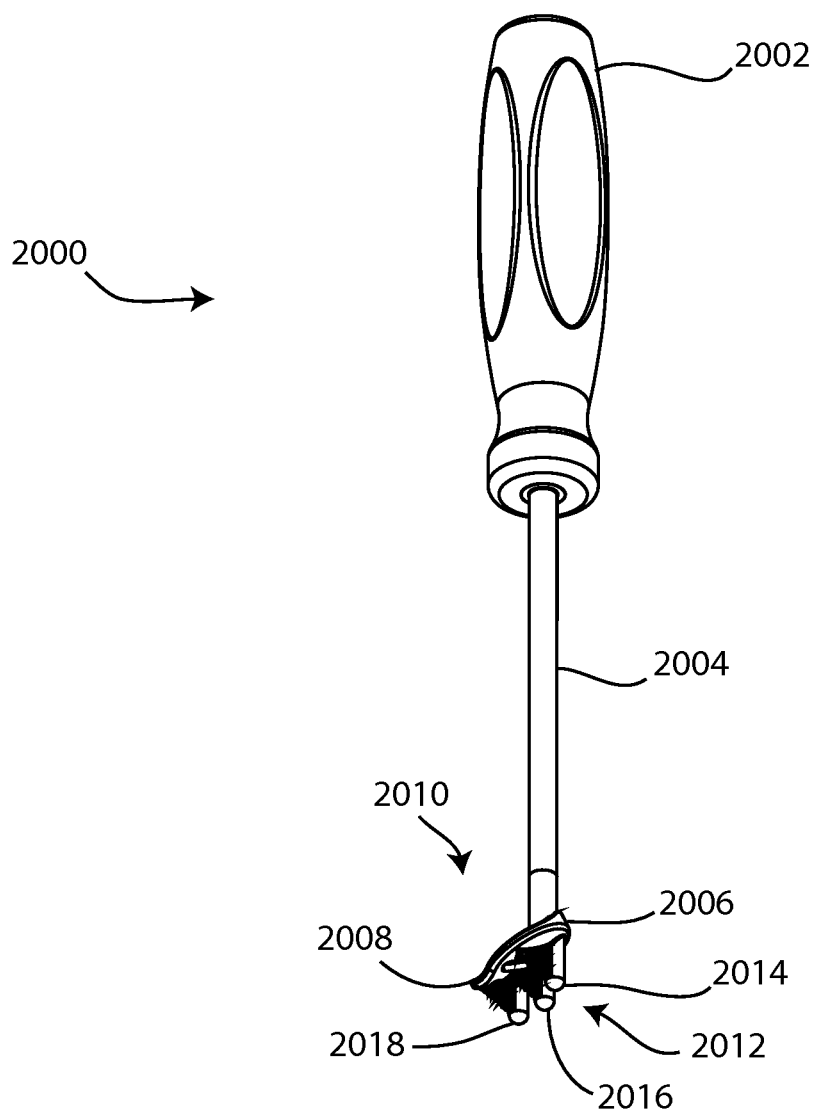
FIG. 28A is an isometric view of a broach.
Figure 28B:
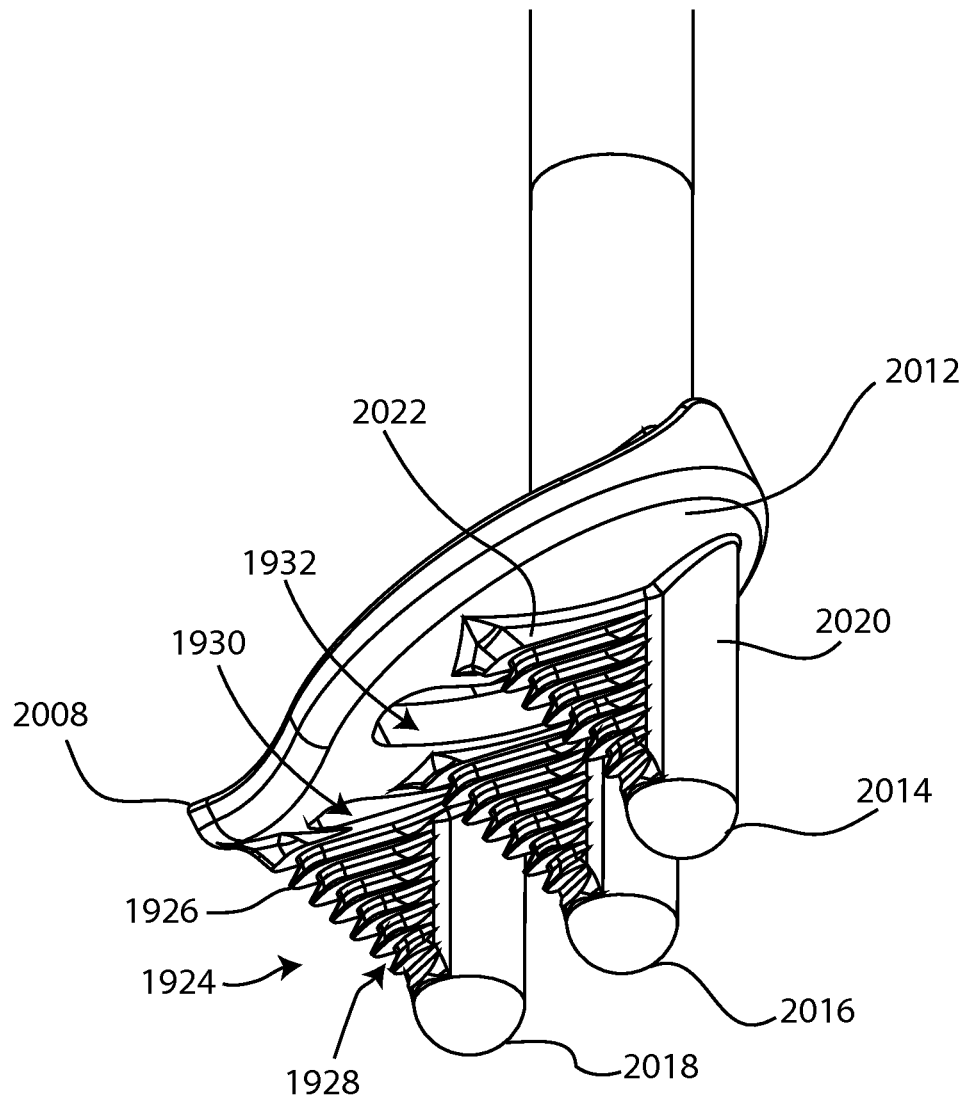
FIG. 28B is a detail view of a working portion of the broach of FIG. 28A.
Figure 28C:
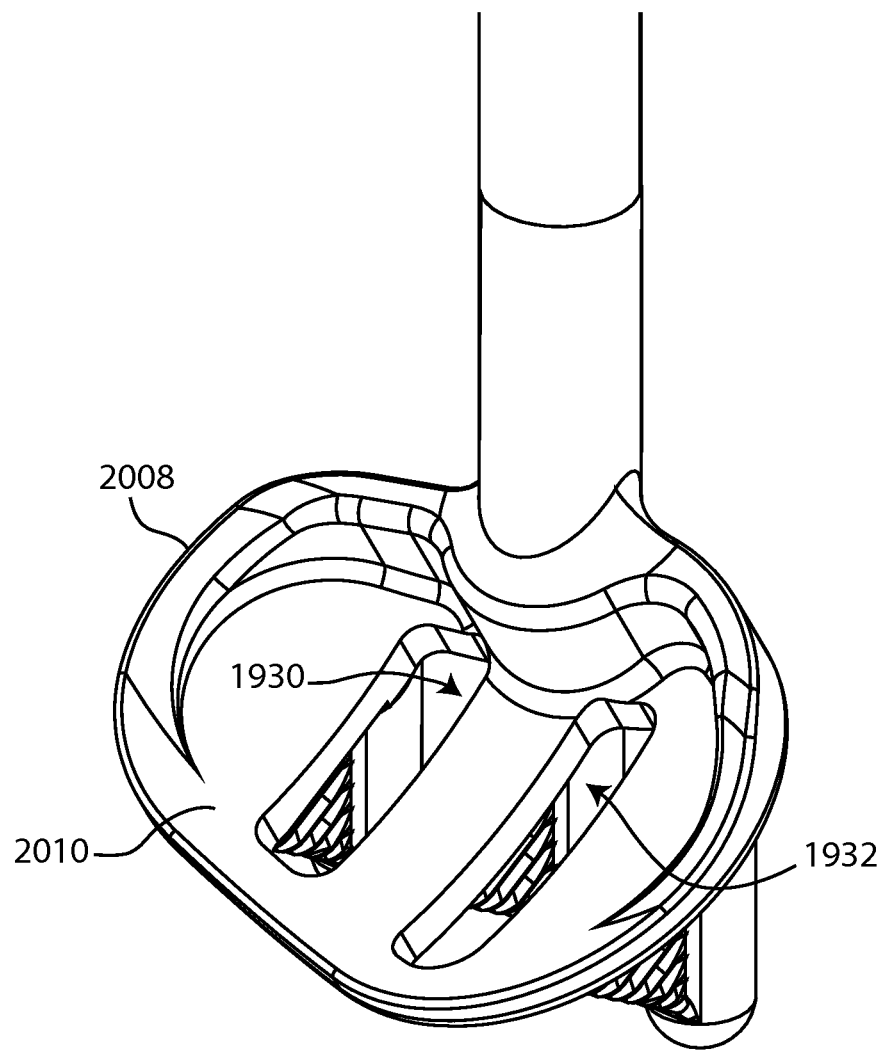
FIG. 28C is another detail view of a working portion of the broach of FIG. 28A from a different direction.

Referring to FIGS. 28A-28C, a broach 2000 includes a handle 2002, a shaft 2004, and a working portion 2006. The handle 2002 and the working portion 2006 are arranged at opposite ends of the shaft 2004, which is straight in this example. The working portion 2006 includes a body 2008 with a first surface 2010 and an opposite bone-facing surface 2012. The bone-facing surface 2012 may match the bone-facing surface 106, 206, 306, 406, 506, 706 of one of the glenoid components. The body 2008 is oriented at an obtuse angle relative to the shaft 2004. The obtuse angle is greater than ninety degrees and less than one hundred eighty degrees. The working portion 2006 includes at least one anchoring element 2014 which protrudes outwardly from the bone-facing surface. The example shown includes anchoring elements 2014, 2016, 2018. Each anchoring element includes a dowel 2020 and a triangular reinforcement plate 2022, as described above for the glenoid components. The dowel 2020 and/or reinforcement plate 2022 may include bone removal features 1924, which may be teeth, serrations, ridges and grooves, knurling, a sandpaper texture, or the like, so that the broach 2000 may be used to form a complementary bone socket to receive a glenoid component. In the example shown, the bone removal features 1924 are on the reinforcement plates 2022, and include alternating ridges or teeth 1926 and grooves 1928. The body 2008 may include at least one aperture to provide a visualization window for the user to judge when the bone-facing surface makes contact with bone; the example shows two apertures 1930, 1932. The body 2008 may resemble one of the previously-described glenoid components, as illustrated in FIGS. 28A-28C. Alternatively, the body 2008 may include only enough material to form or surround the surfaces, hole(s), and/or protrusion described above.

Referring now to FIGS. 29-41, methods of using the instruments to prepare an implantation site for the glenoid components will now be described. One of skill in the art will appreciate that there are many methods for preparing a glenoid to receive the disclosed glenoid components, and that the methods shown below represent a few examples of the methods available. Other methods contemplated may include the use of a saw, such as a reciprocating or oscillating saw; a burr, which may be motorized; a punch; an osteotome; and/or a curette, used alone or in combination with one or more drills, guides, and/or cutting jigs. These tools may be used to prepare the glenoid to receive one or more dowels and/or reinforcement plates. Furthermore, while the illustrated method and corresponding instruments include three anchoring elements, in other examples of the technology, the method and corresponding instruments include one or more anchoring elements corresponding to the number and location of the anchoring elements that are present on the selected glenoid prosthetic component.

Figure 29:
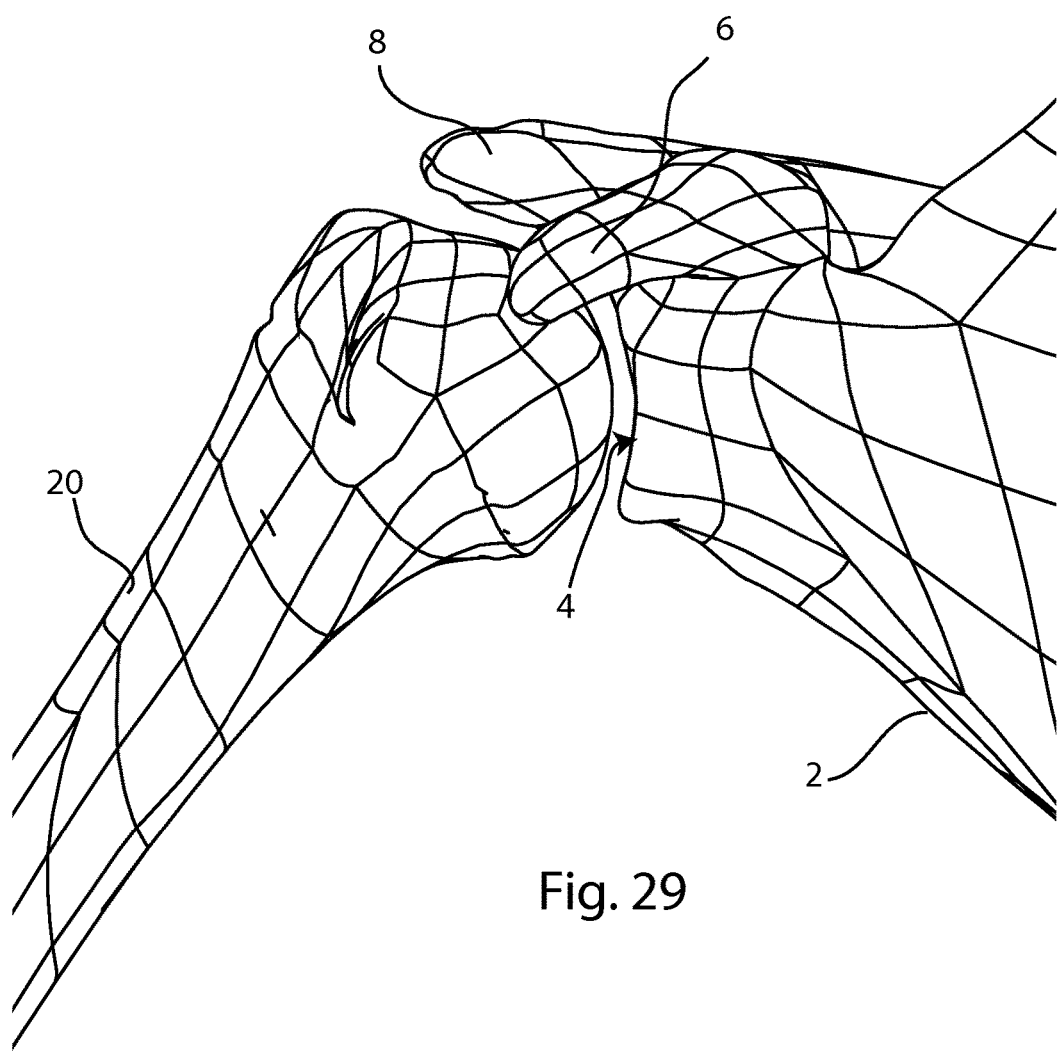
FIG. 29 is an anterior view of a right shoulder joint with a scapula and a humerus.

FIG. 29 illustrates a normal intact right shoulder joint including a scapula 2 and a humerus 20. The scapula includes a glenoid fossa 4, a coracoid process 6, and an acromion process 8.

Figure 30:
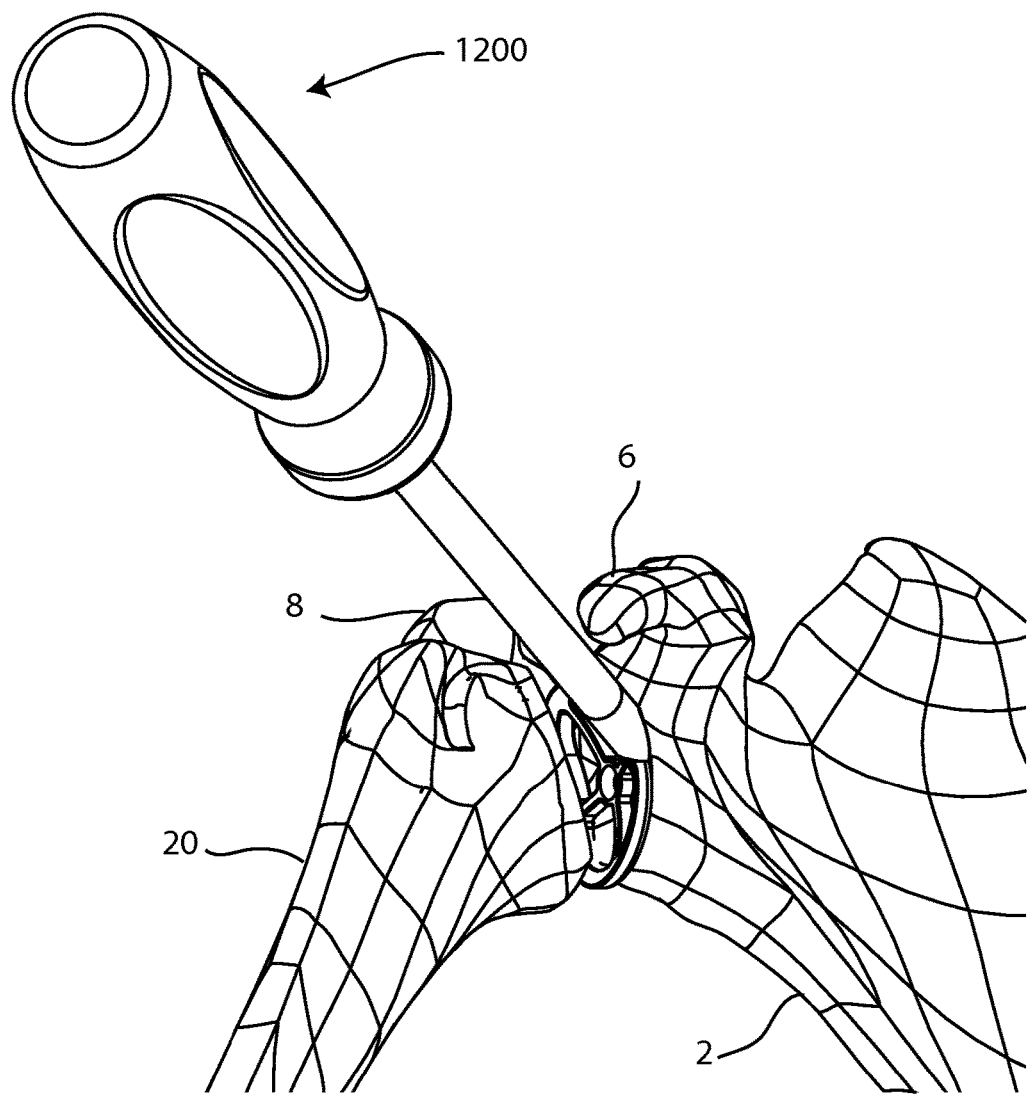
FIG. 30 is an isometric view of the shoulder joint of FIG. 29 with the size template of FIG. 20A.
Figure 31:
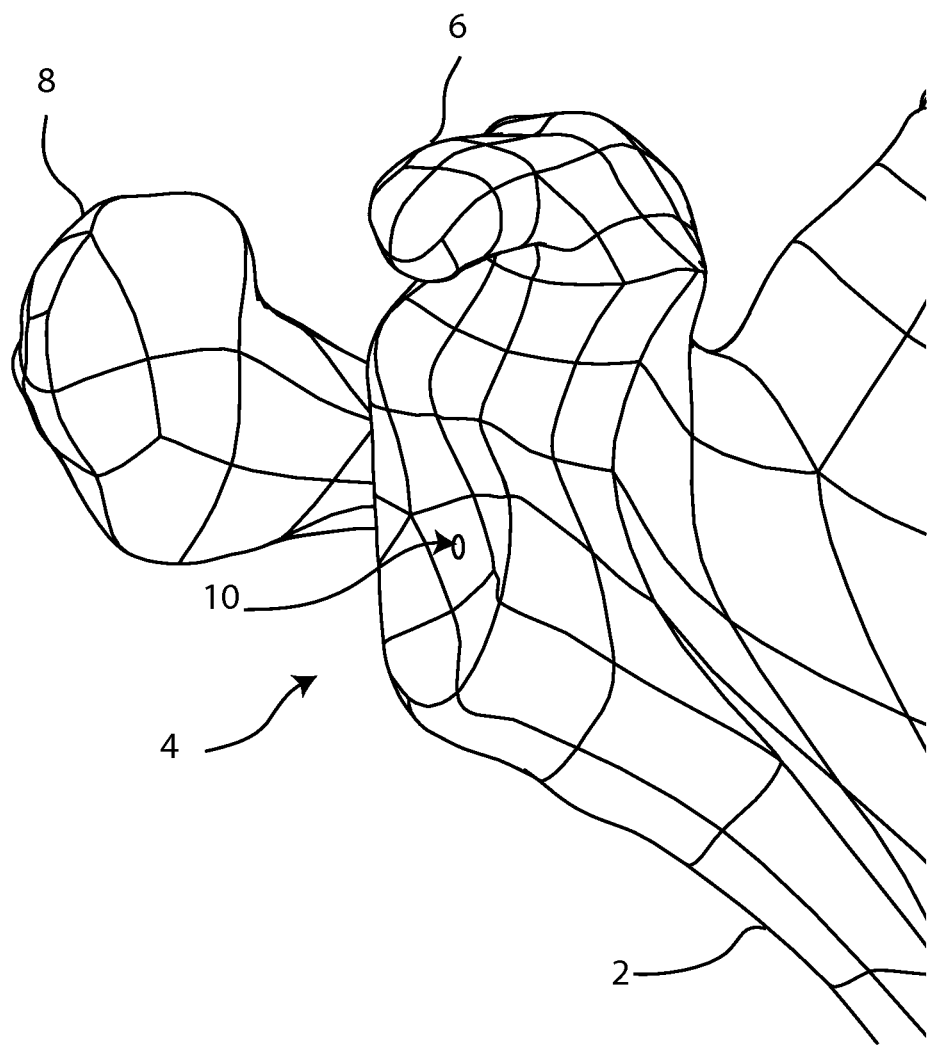
FIG. 31 is an isometric view of the scapula of FIG. 29 after sizing.

FIG. 30 illustrates the step of inserting the sizing template 1200 between the humeral head and the glenoid fossa 2. A drill, Beath pin, or K-wire may be inserted through the central hole 1216 to form a pilot hole 10 in the glenoid fossa, as can be seen in FIG. 31. A small drill or reamer (not shown) may be used freehand at this point to expand the pilot hole 10.

Figure 32:
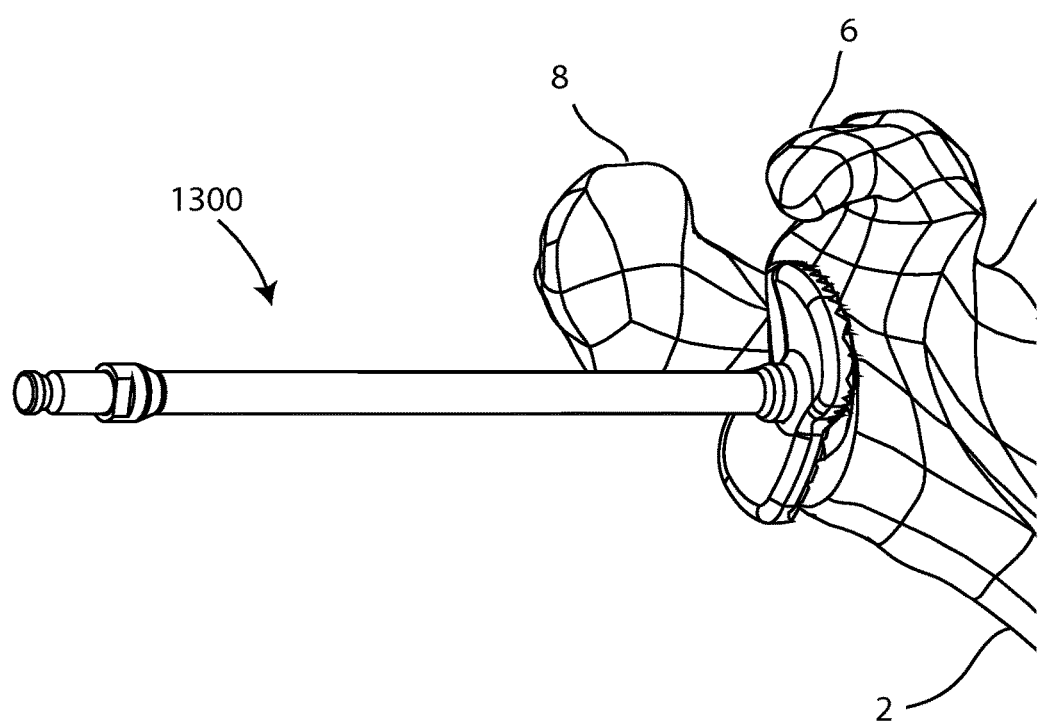
FIG. 32 is an isometric view of the scapula of FIG. 29 with the reamer of FIG. 21A.
Figure 33:
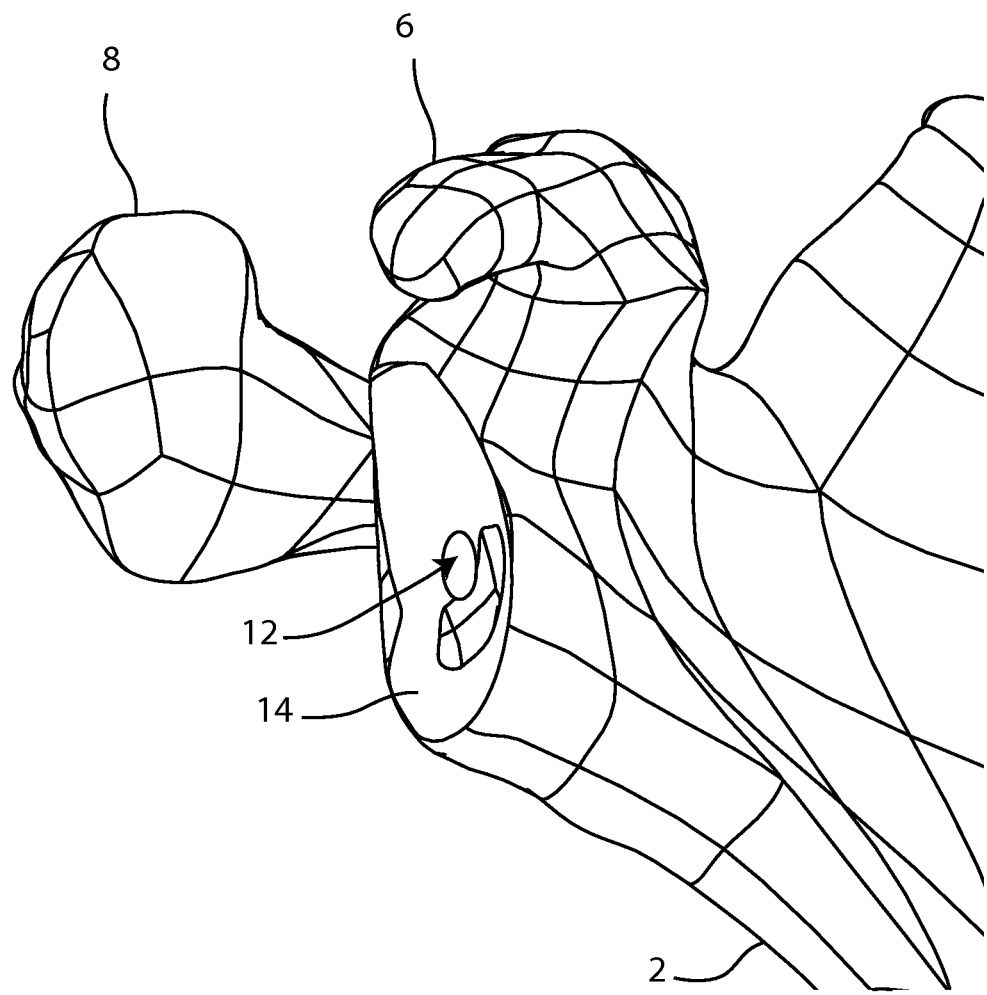
FIG. 33 is an isometric view of the scapula of FIG. 29 after reaming.

FIG. 32 illustrates the step of reaming the glenoid fossa. The reamer 1300 may be insinuated between the humeral head and the glenoid fossa 2 by first engaging the drill tip 1332 in the pilot hole 10 with one of the indentations 1318, 1320 cradling the humeral head. The reamer shaft 1304 may be inclined at an acute angle with respect to the glenoid fossa at this point. With the drill tip 1332 in the pilot hole, there is sufficient leverage to push the humeral head posteriorly with the reamer 1300. The reamer shaft 1304 may end up perpendicular to the glenoid fossa at this point. Once the reamer shaft 1304 is properly aligned with the glenoid fossa 4 and the scapula 2, the reamer 1300 may be spun to prepare a reamed surface 14 in the glenoid fossa 4. At the same time, the drill tip 1332 and drill feature 1334, if present, prepare hole 12 in the former location of the pilot hole 10. FIG. 33 shows the scapula 2 after the reaming step.

Figure 34A:
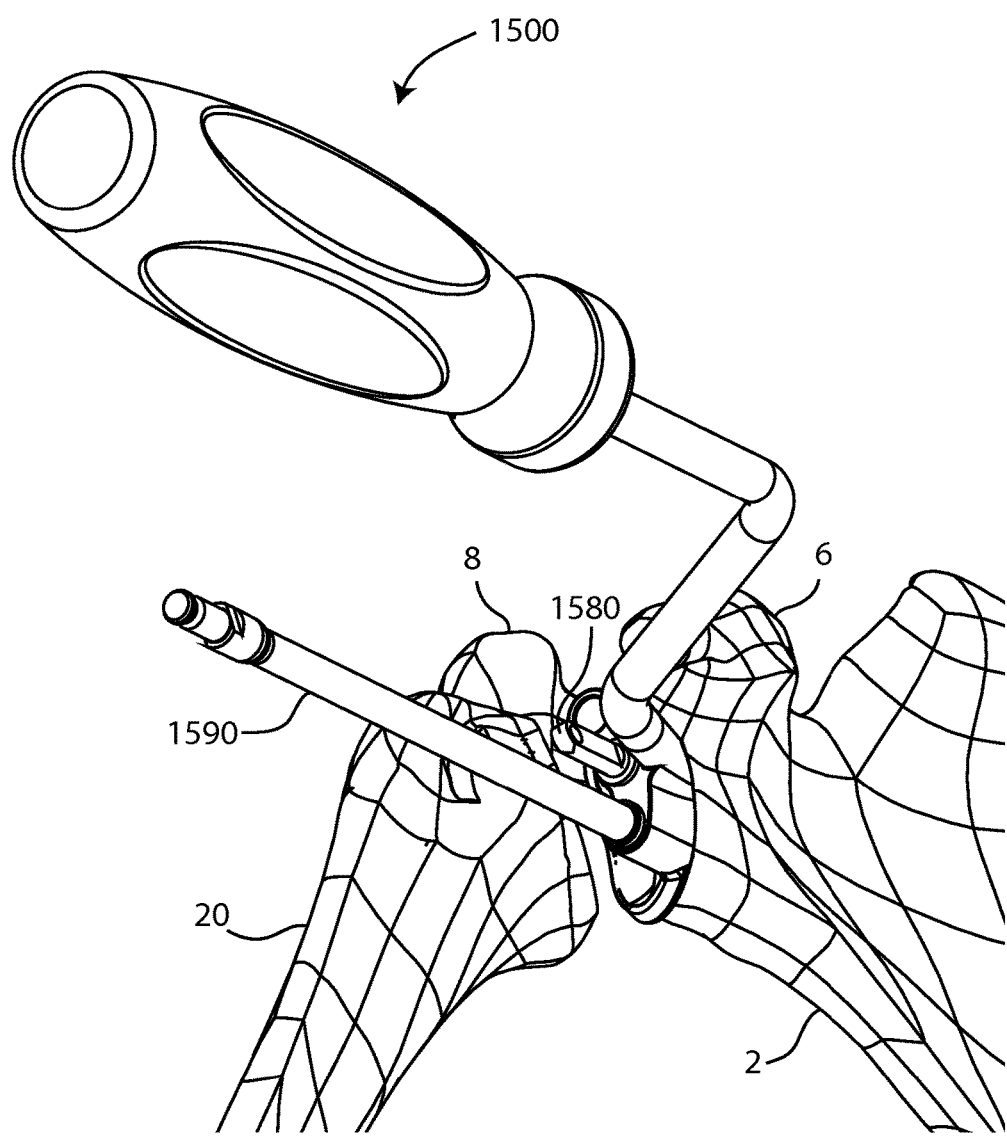
FIG. 34A is an isometric view of the shoulder joint of FIG. 29 with the drill guide, drill, and keel position tamp of FIG. 23A.
Figure 34B:
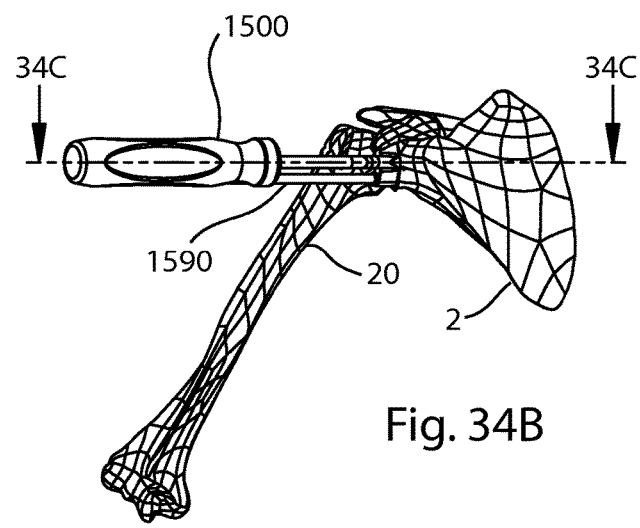
FIG. 34B is an anterior view of the shoulder joint, drill guide, drill, and keel position tamp of FIG. 34A.
Figure 34C:
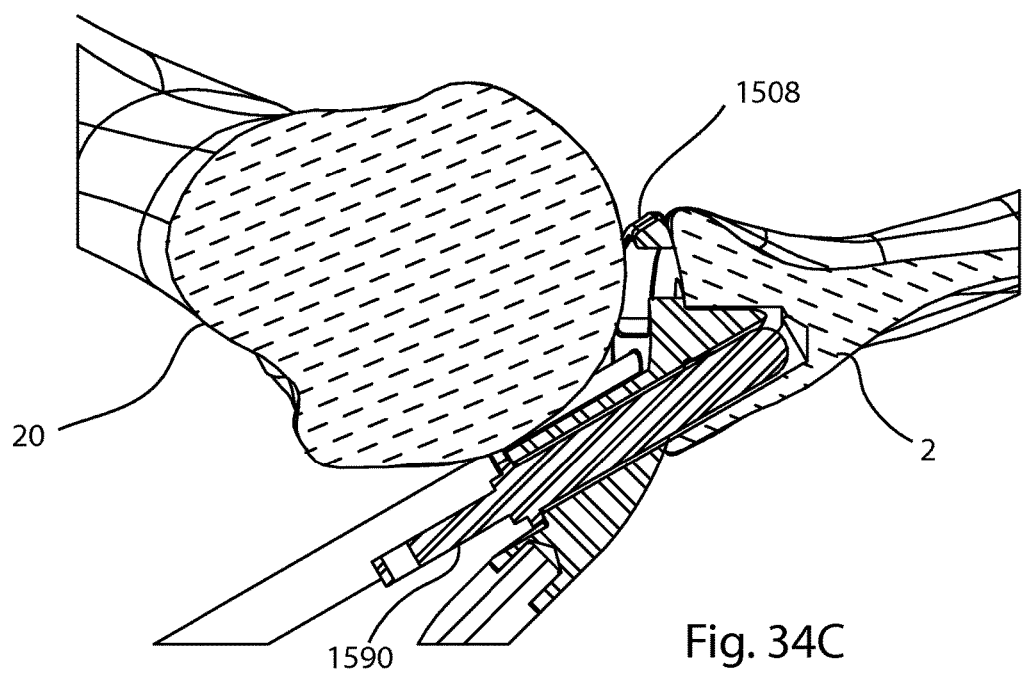
FIG. 34C is a cross sectional view of the shoulder joint, drill guide, drill, and keel position tamp of FIG. 34A, taken along section line 34C-34C of FIG. 34B.
Figure 35:
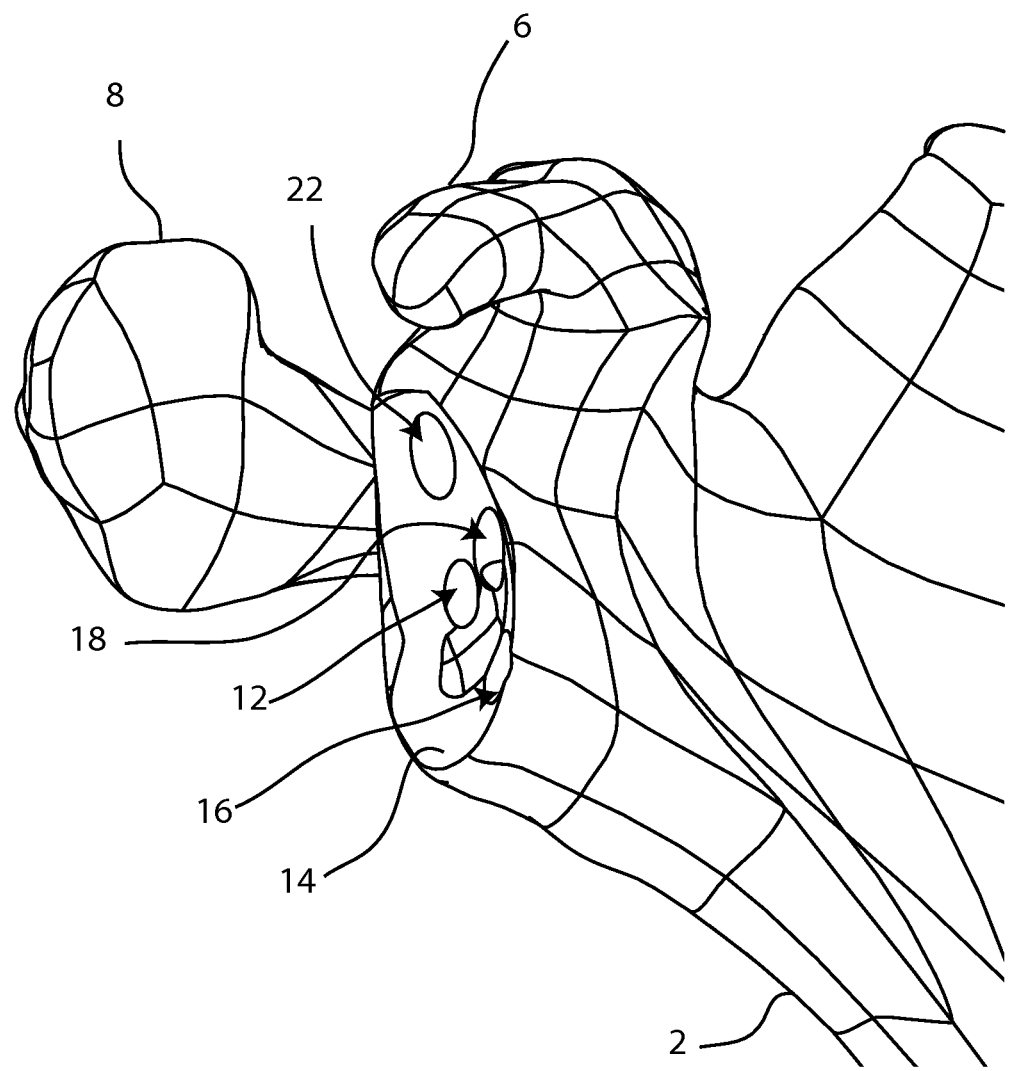
FIG. 35 is an isometric view of the scapula of FIG. 29 after a first drilling step.

FIGS. 34A-34C illustrate the step of drilling dowel holes. The drill guide 1500 is inserted between the humeral head and the glenoid fossa 4 so that the central peg 1526 is received in hole 12. The drill guide 1500 is then rotated about the central peg 1526 until the body 1508 is rotationally aligned as desired with the glenoid fossa 4. The drill guide 1500 is manually stabilized while drill 1590 is actuated through one of the holes 1514, 1516, 1518, for example, hole 1516, thus creating dowel hole 18 in the glenoid fossa 4. The drill 1590 is removed, and the keel position tamp 1580 is inserted through holes 1516, 18 to rotationally stabilize the drill guide 1500. Drill 1590 is then actuated through the remaining two holes 1514, 1518 to create dowel holes 16, 22, respectively. FIG. 35 shows the scapula 2 after the first drilling step. The drill guide 1400 may be substituted for the drill guide 1500 in this step by using a peg or screw in central hole 1426 and hole 12.

Figure 36:
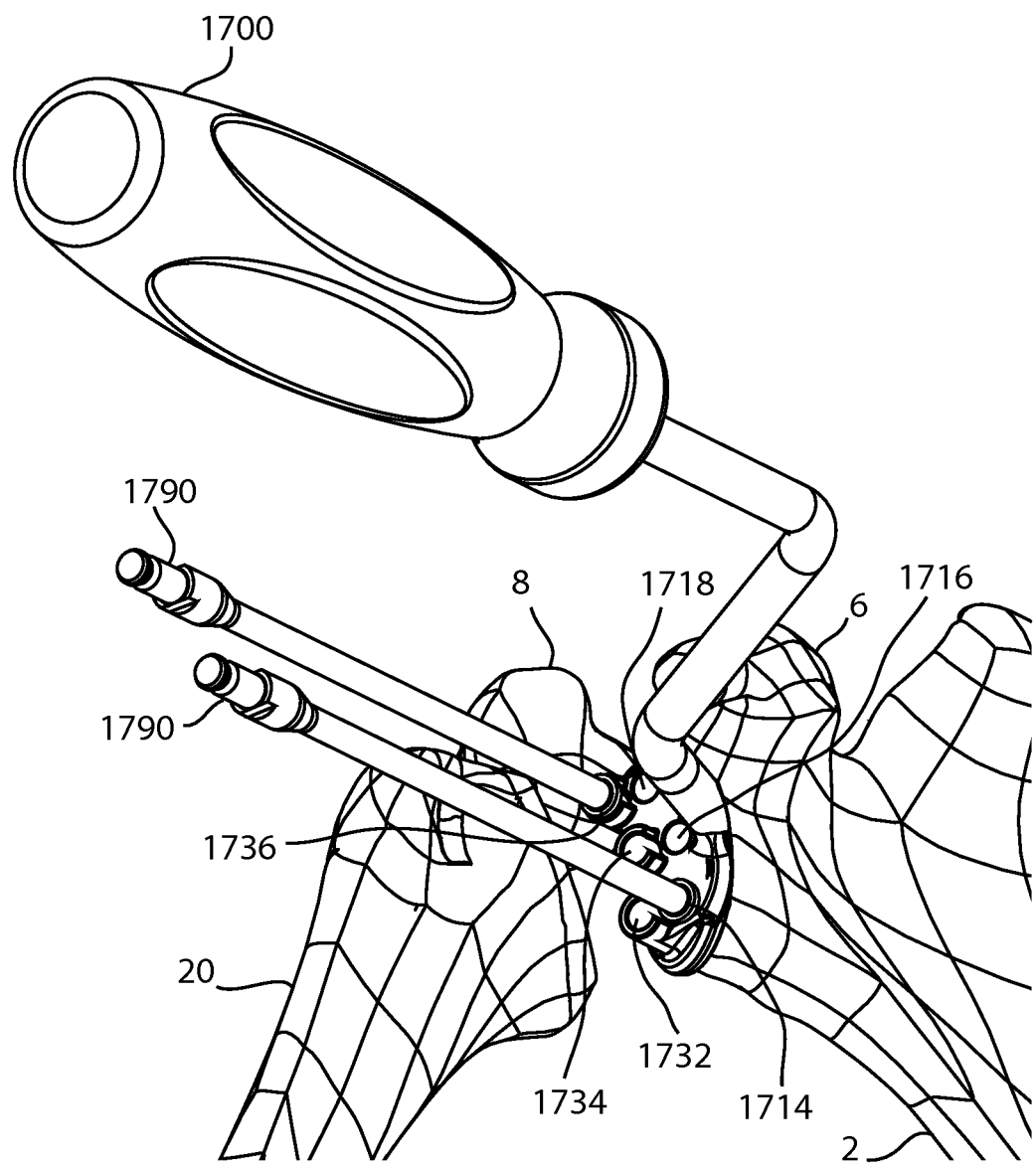
FIG. 36 is an isometric view of the shoulder joint of FIG. 29 with the drill guide and drills of FIG. 25A.
Figure 37:
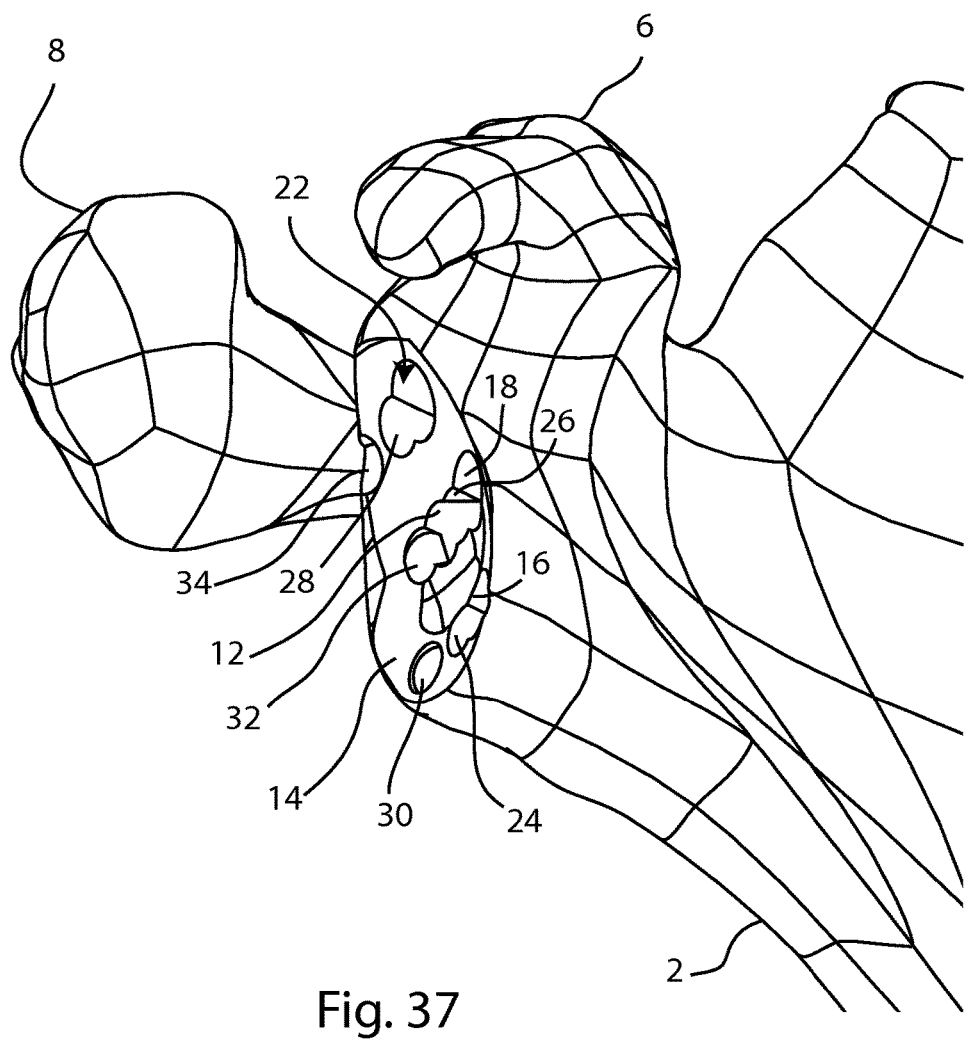
FIG. 37 is an isometric view of the scapula of FIG. 29 after a second drilling step.

FIG. 36 illustrates the step of drilling a first and second set of plate holes. The drill guide 1700 is inserted between the humeral head and the glenoid fossa 4 so that the pegs 1744, 1746, 1748 are received in holes 16, 18, 22, respectively. The drill 1790 is actuated through each one of holes 1714, 1716, 1718, 1732, 1734, 1736 to form plate holes 24, 26, 28, 30, 32, 34, respectively. FIG. 37 shows the scapula 2 after the second drilling step.

Figure 38:
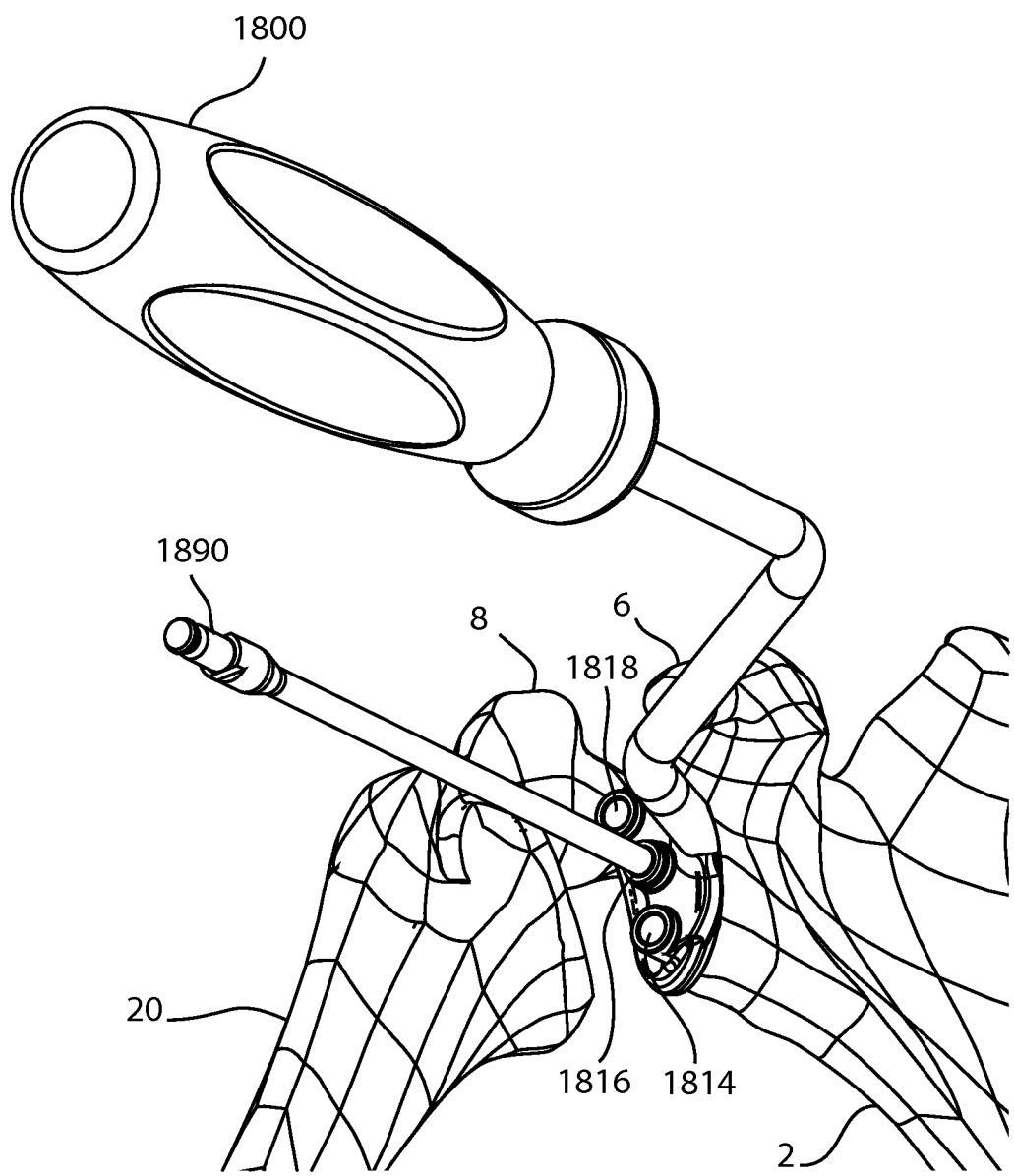
FIG. 38 is an isometric view of the shoulder joint of FIG. 29 with the drill guide and drills of FIG. 26A.
Figure 39:
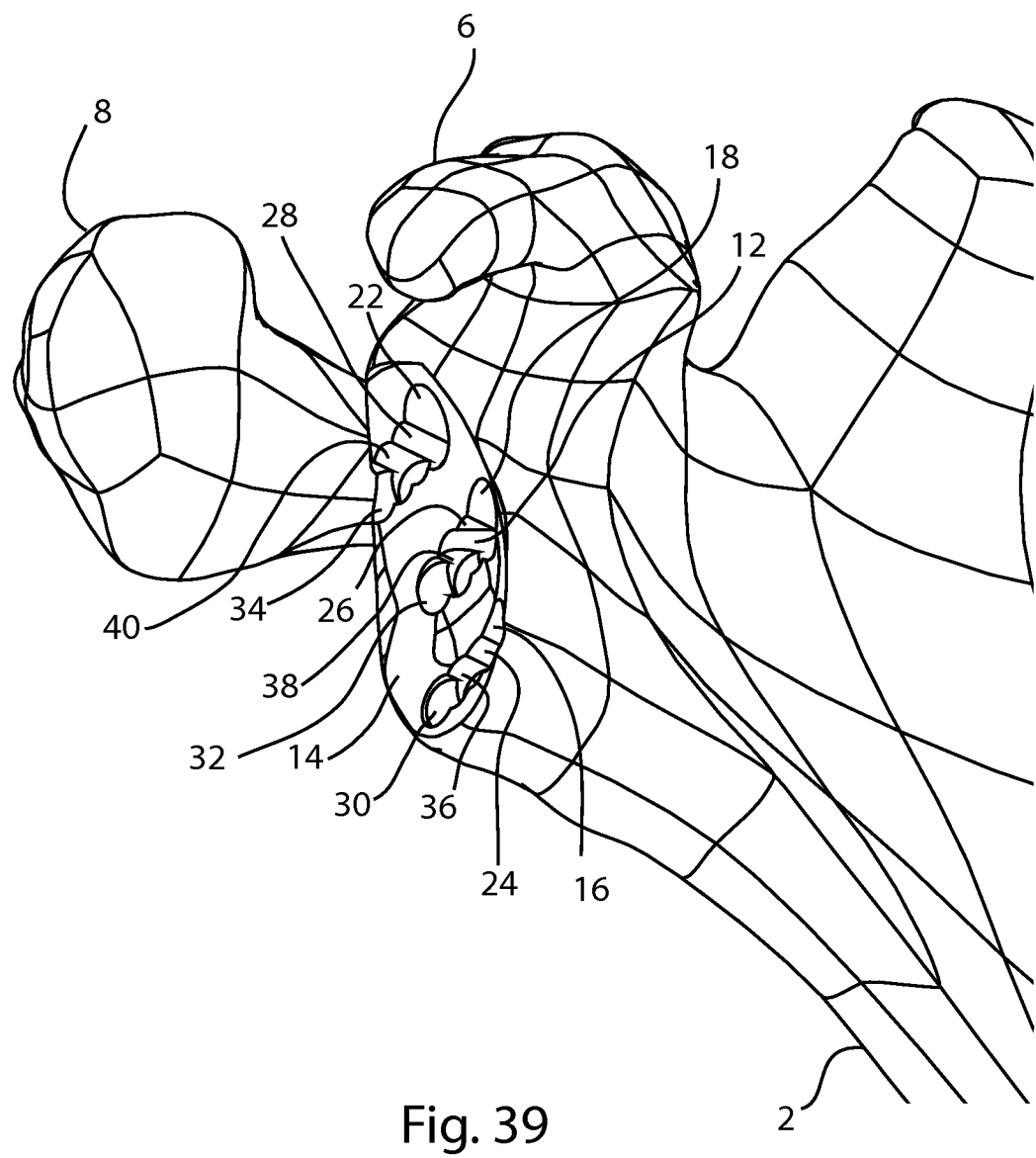
FIG. 39 is an isometric view of the scapula of FIG. 29 after a third drilling step.

FIG. 38 illustrates the step of drilling a third set of plate holes. The drill guide 1800 is inserted between the humeral head and the glenoid fossa 4 so that the pegs 1844, 1846, 1848 are received in holes 16, 18, 22, respectively. The drill 1890 is actuated through each one of holes 1814, 1816, 1818 to form plate holes 36, 38, 40, respectively. FIG. 39 shows the scapula 2 after the third drilling step.

Instead of performing the steps illustrated in FIGS. 36-39, all three sets of plate holes may be drilled in a single step using the drill guide 1600 and a suitably sized drill.

Figure 40A:
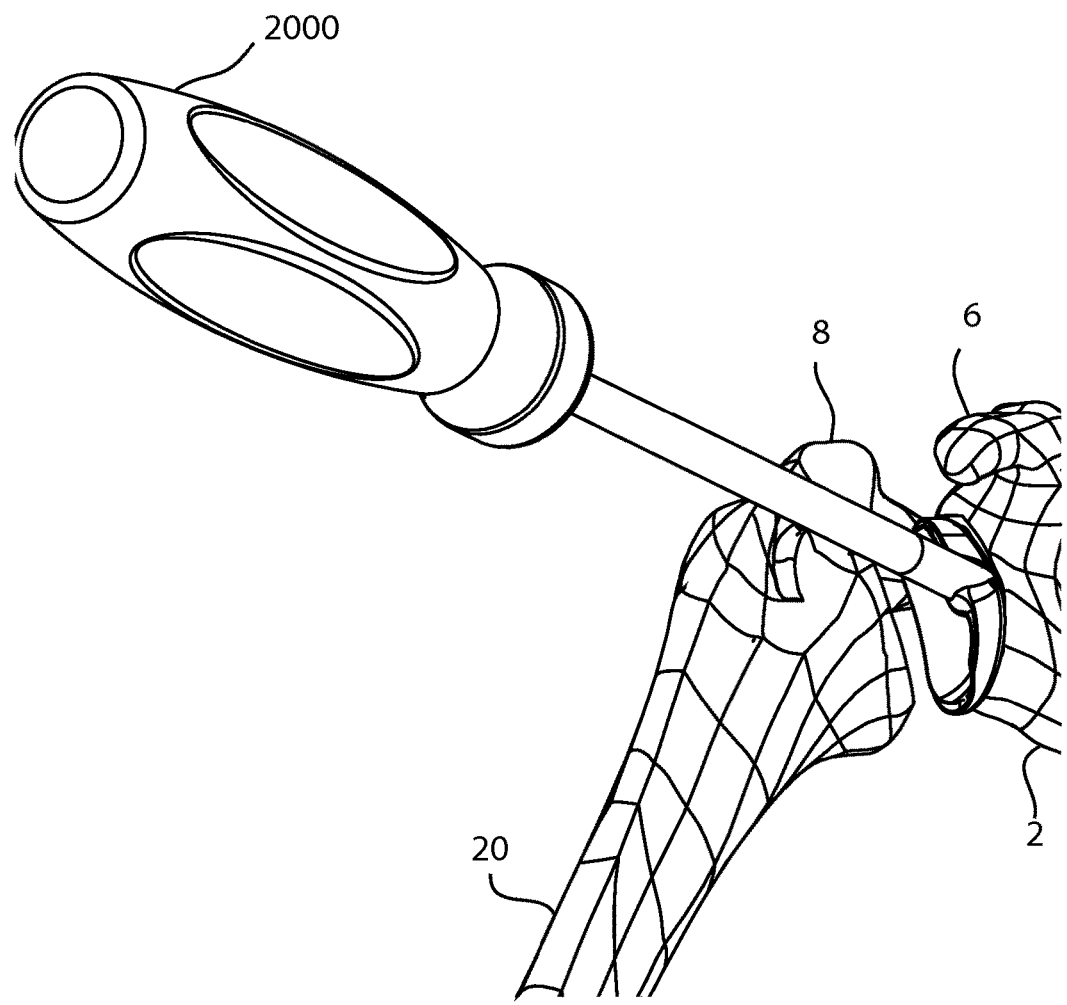
FIG. 40A is an isometric view of the shoulder joint of FIG. 29 with the broach of FIG. 28A.
Figure 40B:
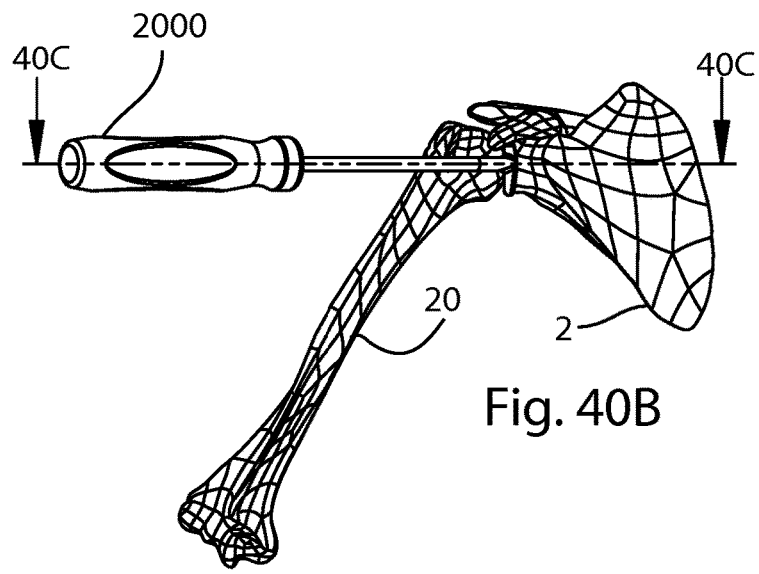
FIG. 40B is an anterior view of the shoulder joint and broach of FIG. 40A.
Figure 40C:
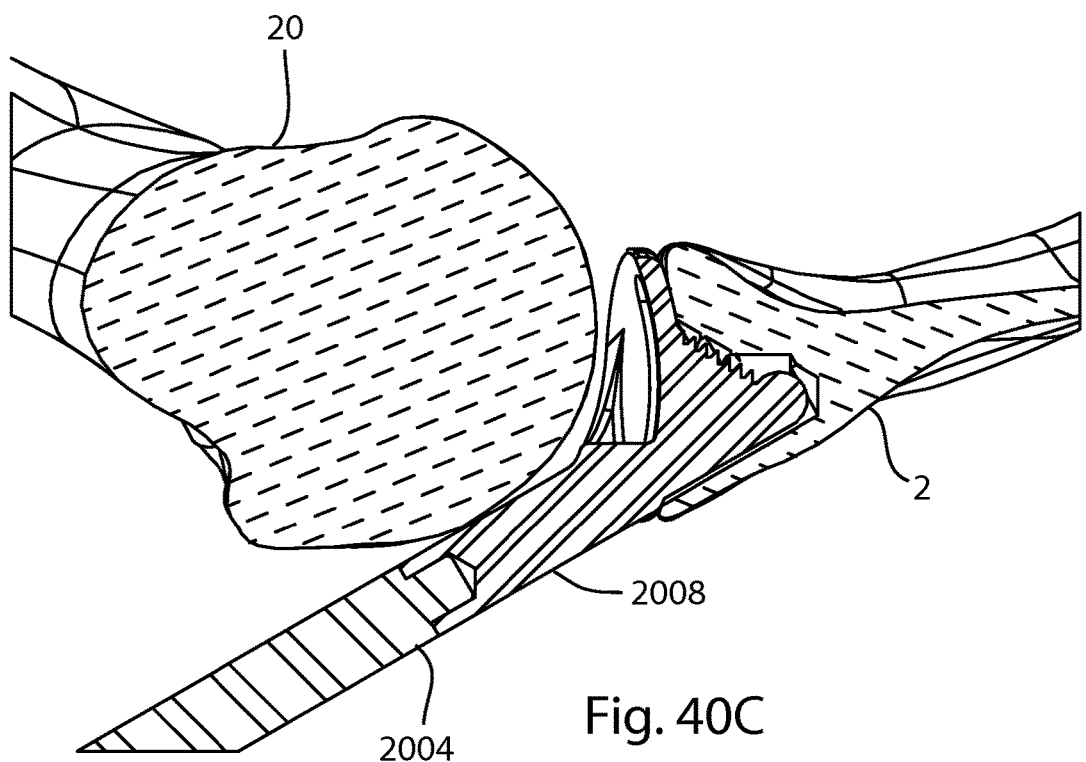
FIG. 40C is a cross sectional view of the shoulder joint and broach of FIG. 40A, taken along section line 40C-40C of FIG. 40B.
Figure 41:
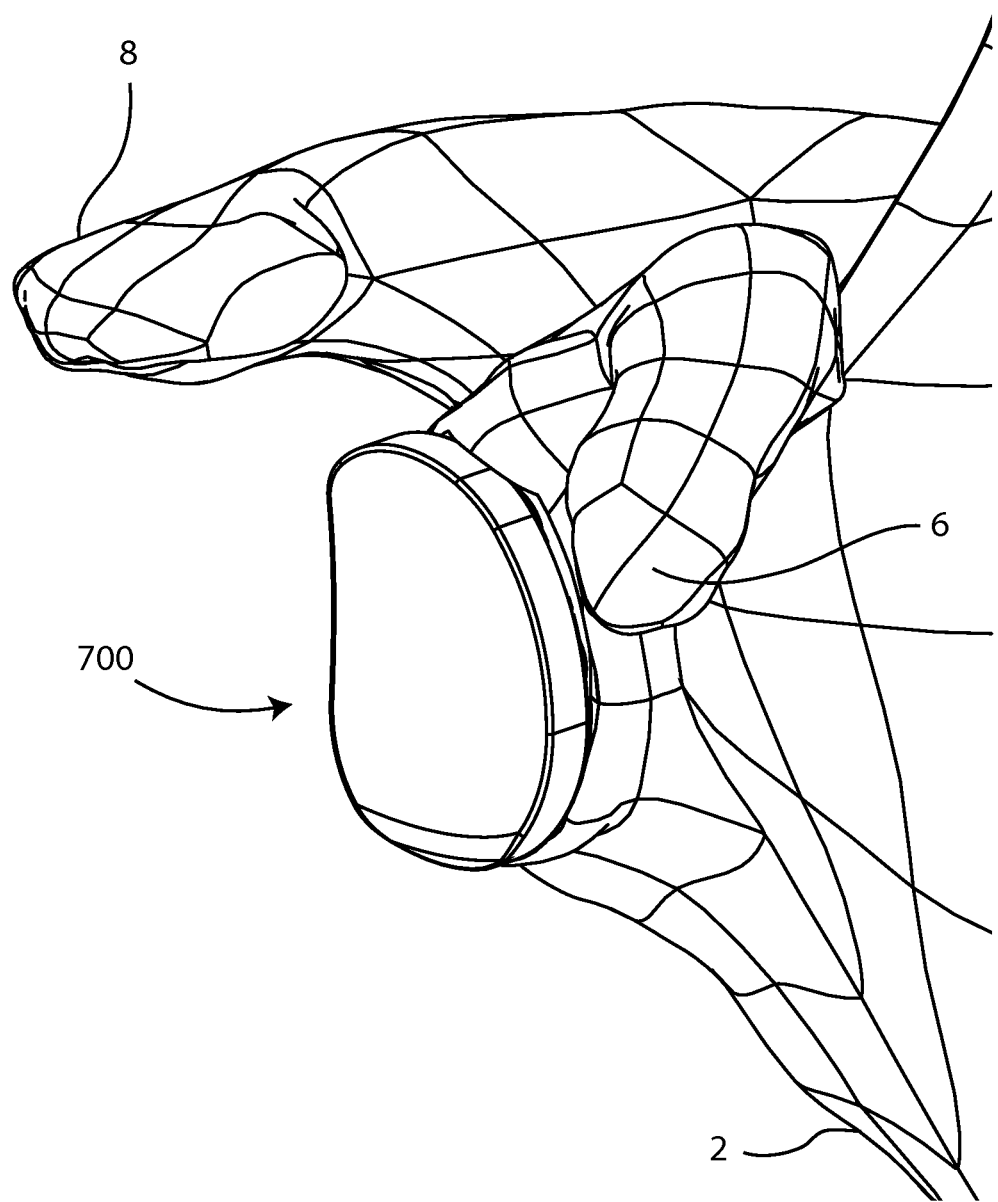
FIG. 41 is an isometric view of the scapula of FIG. 29 and the glenoid component of FIG. 19A.

FIG. 40A-40C illustrate the step of broaching a bone socket to receive a glenoid component. This step may be a fine-tuning step if performed after the steps illustrated in FIGS. 29-39; this step may optionally be performed instead of some or all of the steps illustrated in FIGS. 29-39. The broach 2000 is inserted between the humeral head and the glenoid fossa 4 so that the anchoring elements 2014, 2016, 2018 are received in the prepared bone holes, with the dowels 2020 in the dowel holes 16, 18, 22 and the plates 2022 in the overlapping plate holes. The broach 2000 may be tapped into full engagement with the glenoid fossa 2 while monitoring progress through the apertures 1930, 1932. In another technique, the broach 2000 may be reciprocally advanced and withdrawn. The broach 2000 forms a bone socket (not shown) which is complementary to the glenoid component. The bone socket may be larger all over than the glenoid component in order to provide clearance for an even mantle of bone cement around the anchoring elements of the glenoid component. The punch 1900 may be used instead of the broach 2000 in this step. The punch 1900 may also be used after the broach, and after the introduction of freshly mixed bone cement into the bone socket, to press the bone cement into the bony interstices before the final step, insertion of the prosthetic glenoid component. FIG. 41 illustrates the scapula 2 after implantation of a glenoid component 700.

The components disclosed herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, ultra high molecular weight polyethylene (UHMWPE), biocompatible materials, and biodegradable materials, among others. Different materials may be used for different parts. Coatings may be present. Different materials may be used within a single part. Any component disclosed herein may be colored, coded or otherwise marked to make it easier for a user to identify the type and size of the component, the setting, the function(s) of the component, and the like.

It should be understood that the present systems, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term or in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several examples for the purpose of streamlining the disclosure. This method of disclosure is not to be interpreted as reflecting an intention that the examples of the invention require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

The invention claimed is:

1. An arthroplasty system comprising:
  a first arthroplasty prosthesis comprising a body and an anchoring element, wherein the body comprises an articular surface and a bone-facing surface opposite the articular surface, wherein the body comprises a length dimension and a width dimension perpendicular to the length dimension, wherein the length dimension is greater than the width dimension, wherein a plane extends parallel to the width dimension and normal to the articular surface, wherein the anchoring element comprises a dowel and a triangular reinforcement plate, wherein the dowel projects from the bone-facing surface at an acute first angle, wherein the dowel terminates in a free end, wherein the reinforcement plate extends between the bone-facing surface and the dowel in the first angle, wherein the reinforcement plate comprises a first side extending along the bone-facing surface, a second side extending along the dowel, and a third side extending from the free end of the dowel to the bone-facing surface, wherein the third side forms a second angle with the bone-facing surface, wherein, when the bone-facing surface is viewed parallel to the plane, the anchoring element is parallel to the plane, wherein the first arthroplasty prosthesis is adapted for a surgical approach parallel to the plane along a trajectory extending along the dowel.

2. The system of claim 1, wherein a peripheral wall extends around the body between the articular surface and the bone-facing surface, wherein a chamfer extends between the articular surface and the peripheral wall, wherein the peripheral wall has a uniform height around the body except at the chamfer, wherein the height of the peripheral wall is reduced by the chamfer.

3. The system of claim 1, wherein the articular surface comprises a first radius of curvature in a first plane normal to the articular surface, wherein the articular surface comprises a second radius of curvature in a second plane normal to the articular surface, wherein the second radius of curvature is dimensionally different from the first radius of curvature, wherein the second plane intersects the first plane.

4. The system of claim 1, wherein the dowel projects from a peripheral portion of the bone-facing surface, wherein the free end of the dowel is medially located.

5. The system of claim 1, wherein the anchoring element comprises a pedestal which enlarges at least a portion of the anchoring element at the bone-facing surface.

6. The system of claim 1, comprising:
a second arthroplasty prosthesis comprising a body, wherein the body of the second arthroplasty prosthesis comprises an articular surface and a bone-facing surface opposite the articular surface, wherein the articular surface of the second arthroplasty prosthesis articulates with the articular surface of the first arthroplasty prosthesis.

7. The system of claim 6, wherein the first arthroplasty prosthesis is a shoulder arthroplasty glenoid component and the second arthroplasty prosthesis is a shoulder arthroplasty humeral component.

8. An arthroplasty system comprising:
a first arthroplasty prosthesis comprising a body and an anchoring element, the body comprising an articular surface and a bone-facing surface opposite the articular surface, the bone-facing surface comprising a length dimension and a width dimension perpendicular to the length dimension, wherein the length dimension is greater than the width dimension, wherein a plane extends parallel to the width dimension and normal to the articular surface, the anchoring element comprising a plate and a dowel, wherein the plate projects from the bone-facing surface, wherein the plate comprises first, second, and third sides which form a triangular shape, wherein the first side of the plate forms a first angle with the bone-facing surface, wherein the second side of the plate forms a second angle with the bone-facing surface, wherein the third side of the plate is formed by the bone-facing surface, wherein the dowel projects from the bone-facing surface to form the first side of the plate, wherein the second angle opens toward the first angle, wherein the first and second angles are each greater than zero degrees and less than ninety degrees, wherein, when the bone-facing surface is viewed parallel to the plane, the anchoring element is parallel to the plane, wherein the first arthroplasty prosthesis is adapted for a surgical approach parallel to the plane along a trajectory extending along the dowel.

9. The system of claim 8, wherein the third side of the plate is reinforced at the bone-facing surface.

10. The system of claim 8, wherein a lengthwise channel extends along the second side of the plate.

11. The system of claim 8, wherein a peripheral wall extends around the body between the articular surface and the bone-facing surface, wherein a chamfer extends between the articular surface and the peripheral wall, wherein the peripheral wall has a uniform height around the body except at the chamfer, wherein the height of the peripheral wall is reduced by the chamfer.

12. The system of claim 11, wherein the articular surface comprises a first radius of curvature in a first plane normal to the articular surface, wherein the articular surface comprises a second radius of curvature in a second plane normal to the articular surface, wherein the second radius of curvature is dimensionally different from the first radius of curvature, wherein the second plane intersects the first plane.

13. The system of claim 12, wherein the first arthroplasty prosthesis is a shoulder arthroplasty glenoid component, wherein the first plane is a coronal plane, wherein the second plane is a transverse plane, wherein the first radius is larger than the second radius.

14. The system of claim 13, comprising a second arthroplasty prosthesis, wherein the second arthroplasty prosthesis is a shoulder arthroplasty humeral component.

15. An arthroplasty system comprising:
a first arthroplasty prosthesis comprising:
a body comprising an articular surface and a bone-facing surface opposite the articular surface, wherein the articular surface comprises a length dimension and a width dimension perpendicular to the length dimension, wherein the length dimension is greater than the width dimension, wherein a plane extends parallel to the width dimension and normal to the articular surface; and
an anchoring element comprising a dowel and a triangular plate, wherein the dowel projects at a first angle from the bone-facing surface and terminates in a free end, wherein the triangular plate projects from the bone-facing surface to fill the first angle, wherein a first side of the triangular plate lies along the bone-facing surface, a second side of the triangular plate lies along the dowel, and a third side of the triangular plate extends between the free end of the dowel and the bone-facing surface to form a second angle with the bone-facing surface, wherein the second angle faces the first angle, wherein the first and second angles are each greater than zero degrees and less than ninety degrees, wherein, when the bone-facing surface is viewed parallel to the plane, the anchoring element is parallel to the plane, wherein the first arthroplasty prosthesis is adapted for a surgical approach parallel to the plane along a trajectory extending along the dowel.

16. The system of claim 15, wherein a peripheral wall extends around the body between the articular surface and the bone-facing surface, wherein a chamfer extends between the articular surface and the peripheral wall, wherein the peripheral wall has a uniform height around the body except at the chamfer, wherein the height of the peripheral wall is reduced by the chamfer.

17. The system of claim 15, wherein the articular surface comprises a first radius of curvature in a first plane normal to the articular surface, wherein the articular surface comprises a second radius of curvature in a second plane normal to the articular surface, wherein the second radius of curvature is dimensionally different from the first radius of curvature, wherein the second plane intersects the first plane.

18. The system of claim 15, wherein the dowel projects from a peripheral portion of the bone-facing surface, wherein the free end of the dowel is medially located.

19. The system of claim 15, wherein the anchoring element comprises a pedestal which enlarges at least a portion of the anchoring element at the bone-facing surface.

20. The system of claim 15, comprising:
a second arthroplasty prosthesis comprising a body, wherein the body of the second arthroplasty prosthesis comprises an articular surface and a bone-facing surface opposite the articular surface, wherein the articular surface of the second arthroplasty prosthesis articulates with the articular surface of the first arthroplasty prosthesis.

* * * * *